United States Patent [19]

Macor et al.

[11] Patent Number: 5,607,951
[45] Date of Patent: Mar. 4, 1997

[54] INDOLE DERIVATIVES

[75] Inventors: John E. Macor; Martin J. Wythes, both of New York, N.Y.

[73] Assignee: Pfizer Inc, New York, N.Y.

[21] Appl. No.: 470,392

[22] Filed: Jun. 6, 1995

Related U.S. Application Data

[63] Continuation-in-part of Ser. No. 401,647, Mar. 10, 1995, abandoned, which is a continuation of Ser. No. 53,930, Apr. 27, 1993, abandoned, which is a continuation-in-part of Ser. No. 39,244, filed as PCT/US91/01794 Oct. 8, 1991, abandoned, which is a continuation-in-part of Ser. No. 597,928, Oct. 15, 1990, abandoned.

[51] Int. Cl.$^6$ .................. A61K 31/40; C07D 401/06; C07D 403/06
[52] U.S. Cl. .................. 514/323; 514/414; 546/201; 548/468
[58] Field of Search .................. 514/323, 414; 546/201; 548/468

[56] References Cited

U.S. PATENT DOCUMENTS

| | | | |
|---|---|---|---|
| 2,773,875 | 12/1956 | Finkelstein | 548/466 |
| 3,037,031 | 5/1962 | Lewis et al. | 548/466 |
| 4,252,803 | 2/1981 | Webb | 424/248.5 |
| 4,803,218 | 2/1989 | Stanley et al. | 548/466 |
| 4,855,314 | 8/1989 | Oxford et al. | 514/415 |
| 5,208,248 | 5/1993 | Baker et al. | 514/364 |
| 5,348,968 | 9/1994 | Lavielle | 548/468 X |
| 5,409,941 | 4/1925 | Nowakowski | 514/33 |

FOREIGN PATENT DOCUMENTS

| | | |
|---|---|---|
| 465398 | 1/1992 | European Pat. Off. |
| 497512 | 8/1992 | European Pat. Off. |
| 74527 | 4/1954 | Netherlands. |
| 74786 | 5/1954 | Netherlands. |
| 851780 | 10/1960 | United Kingdom. |
| 886684 | 1/1962 | United Kingdom. |
| 893707 | 4/1962 | United Kingdom. |
| 966562 | 8/1964 | United Kingdom. |
| 2081717 | 2/1982 | United Kingdom. |
| 9206973 | 4/1992 | WIPO. |
| 9311106 | 6/1993 | WIPO. |
| 9314087 | 7/1993 | WIPO. |
| 9318032 | 9/1993 | WIPO. |
| 9320073 | 10/1993 | WIPO. |
| 9321177 | 10/1993 | WIPO. |
| 9321180 | 10/1993 | WIPO. |
| 9321178 | 10/1993 | WIPO. |
| 9323396 | 11/1993 | WIPO. |
| 9424127 | 10/1994 | WIPO. |
| 9425023 | 11/1994 | WIPO. |
| 9506636 | 3/1995 | WIPO. |

OTHER PUBLICATIONS

Gray, *J. Org. Chem.*, 23, 1453–1454 (1958).
Moore, et al., *J. Org. Chem.*, 29, 2860–2864 (1964).
Cain, et al., *J. Am. Chem. Soc.*, 105 908, 911, 912 (1983).
Markowitz, et al. *J. Neurosci.*, 7 (12) 4736 (1987).
Lee, et al., *Brain Res.*, 626, 303–305 (1993).
P. P. A. Humphrey, et al., *Br. J. Pharmacol.*, 94, 1128 (1988).
W. Fernik, et al., *Br. J. Pharmacol.*, 96, 83 (1989).
Reggent for Org. Syn, 1, 112 (1967).
Mohr, et al., *Tetrahedron*, 38(1), 147–152 (1982).
Friderichs, et al., *Chem. Ab.*, 83, 28056 (1975).
Kiyooka, et al., *J. Org. Chem.*, 5409 (1989).
Hamada, et al. *Chem. Pharm. Bull.*, 1921 (1982).
Lee, et al., *Soc. Neurosci* Nov. 1993 Meeting 19 (Part 2), #565.6.
Moskowitz, *7th World Congress on Pain* Aug. 1993, #667.
Leonard, et al., *Neuropharm.*, 11, 373–384 (1972).

*Primary Examiner*—Fiona T. Powers
*Attorney, Agent, or Firm*—Peter C. Richardson; Paul H. Ginsburg; Grover F. Fuller, Jr.

[57] ABSTRACT

Compounds of the formula

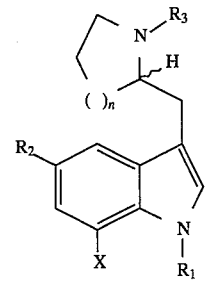

wherein the substituents are as defined in the description and the pharmaceutically acceptable salts thereof are new. These compounds are useful psychotherapeutics and are potent serotonin (5-HT$_1$) agonists and may be used in the treatment of depression, anxiety, eating disorders, obesity, drug abuse, cluster headache, migraine, pain, chronic paroxysmal hemicrania and headache associated with vascular disorders, and other disorders arising from deficient serotonergic neurotransmission. The compounds can also be used as centrally acting antihypertensives and vasodilators. A process for forming indoles by transition metal catalyzed cyclization of a dihalogenated intermediate.

18 Claims, No Drawings

INDOLE DERIVATIVES

This is a continuation-in-part of application Ser. No. 08/401,647, filed Mar. 10, 1995, now abandoned, which, in turn, was a continuation of application Ser. No. 08/053,930, filed as PCT/US91/01794 Oct. 8, 1991, now abandoned which, in turn, was continuation-in-part of application Ser. No. 08/039244, filed on Apr. 27, 1993, now abandoned, the national phase of PCT Ser. No. PCT/US91/01794, filed Oct. 8, 1991, which, in turn, was a continuation-in-part of U.S. Ser. No. 07/597,928, filed Oct. 15, 1990, now abandoned.

BACKGROUND OF THE INVENTION

The present invention relates to indole derivatives, to processes and intermediates for their preparation, to pharmaceutical compositions containing them and to their medicinal use. The active compounds of the present invention are useful in treating migraine and other disorders.

U.S. Pat. No. 4,839,377 and 4,855,314 and European Patent Application Publication Number 313397 refer to 5-substituted 3-aminoalkyl indoles. The compounds are said to be useful for the treatment of migraine.

British Patent Application 040279 refers to 3-aminoalkyl-1H-indole-5-thioamides and carboxamides. The compounds are said to be useful in treating hypertension, Raymond's disease and migraine.

European Patent Application Publication Number 303506 refers to 3-poly:hydro-pyridyl-5-substituted-1H-indoles. The compounds are said to have 5HT1-receptor agonist and vasoconstrictor activity and to be useful in treating migraine.

European Patent Application Publication Number 354777 refers to N-piperidinyl:indolyl:ethyl-alkane sulfonamide derivatives. The compounds are said to have 5HT1-receptor agonist and vasoconstrictor activity and to be useful in treating cephalic pain.

SUMMARY OF THE INVENTION

The present invention relates to compounds of the formula

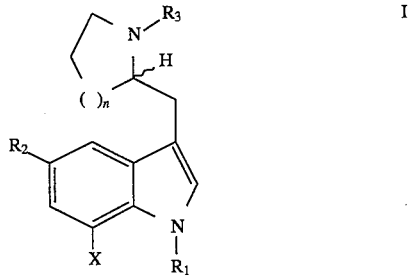

I wherein n is O, or 2; X is hydrogen, chlorine, bromine, or iodine; $R_1$ is hydrogen; $R_2$ is selected from hydrogen, halogen (e.g., fluorine, chlorine, bromine or iodine), cyano, —$OR_4$, —$(CH_2)_m$-(C=O)$NR_5R_6$, —$(CH_2)_m$—$SO_2NR_5R_6$, —$(CH_2)_m$—$NR_7$(C=O)$R_8$, —$(CH_2)_m$—$NR_7SO_2R_8$, —$(CH_2)_m$—$S(O)_xR_8$, —$(CH_2)_m$—$NR_7$(C=O)$NR_5R_6$, —$(CH_2)_m$—$NR_7$(C=O)$OR_9$, and —CH=CH$(CH_2)_yR_{10}$; $R_3$ is selected from hydrogen and $C_1$ to $C_6$ linear and branched alkyl; $R_4$ is selected from hydrogen, $C_1$ to $C_6$ alkyl, and aryl; $R_5$ and $R_6$ are independently selected from hydrogen, $C_1$ to $C_6$ alkyl, aryl, and $C_1$ to $C_3$ alkyl-aryl or $R_5$ and $R_6$ taken together to form a 4, 5, or 6 membered ring; $R_7$ and $R_8$ are independently selected from hydrogen, $C_1$ to $C_6$ alkyl, aryl, and $C_1$ to $C_3$ alkyl-aryl; $R_9$ is selected from hydrogen, $C_1$ to $C_6$ alkyl, aryl, and $C_1$ to $C_3$ alkyl-aryl; $R_{10}$ is selected from —(C=O)$NR_5R_6$ and —$SO_2NR_5R_6$, wherein $R_5$ and $R_6$ are defined as above, and —$NR_7$(C=O)$R_8$, —$NR_7SO_2R_8$, —$NR_7$(C=O)$NR_5R_6$, —$S(O)_xR_8$ and —$N_7$(C=O)$OR_9$, wherein $R_7$, $R_8$, and $R_9$ are as defined above; m is 0, 1, 2, or 3; y is 0, 1, or 2; x is 1 or 2; and the above aryl groups and the aryl moieties of the above alkylaryl groups are independently selected from phenyl and substituted phenyl, wherein said substituted phenyl may be substituted with one to three groups selected from $C_1$ to $C_4$ alkyl, halogen (e.g., fluorine, chlorine, bromine or iodine), hydroxy, cyano, carboxamido, nitro and $C_1$ to $C_4$ alkoxy, with the proviso that when $R_2$ is hydrogen or —$OR_4$ and $R_4$ is hydrogen, n is 0 or 1, and the pharmaceutically acceptable salts thereof. These compounds are useful in treating migraine and other disorders. Compounds of the formula I wherein $R_2$ is —CH=CH$(CH_2)_yR_{10}$ and compounds of formula I where X is chlorine, bromine, or iodine are also useful as intermediates for preparing other compounds of the formula I.

The compounds of the invention include all optical isomers of formula I (e.g., R and S enantiomers) and their racemic mixtures. The R enantiomers at the designated chiral site in formula I are preferred.

Unless otherwise indicated, the alkyl groups referred to herein, as well as the alkyl moieties of other groups referred to herein (e.g. alkoxy), may be linear or branched, and they may also be cyclic (e.g., cyclopropyl, cyclobutyl, cyclopentyl or cyclohexyl) or be linear or branched and contain cyclic moieties.

Preferred compounds of the invention are compounds of the formula I wherein $R_1$ is hydrogen; $R_2$ is —$(CH_2)_m$—$SO_2NHR_5$, —$(CH_2)_m$—$NHSO_2R_8$, —$(CH_2)_m$—$SO_2R_8$, —$(CH_2)_m$—(C=O)$NHR_5$, or —$(CH_2)_m$—$NH(C=O)R_8$; $R_3$ is hydrogen or methyl; and m, $R_5$ and $R_8$ are as defined above and the pharmaceutically acceptable salts thereof. Of the foregoing preferred compounds, the R enantiomers at the designated chiral site in formula I are more preferred.

The following compounds are preferred:

(R)-5-methoxy-3 - (N-methylpyrrolidin-2-ylmethyl)-1H-indole;

(R)-5-bromo-3-(N-methylpyrrolidin-2-ylmethyl)-1H-indole;

(R)-5-(2-ethylsulfonylethyl)-3-(N-methylpyrrolidin-2-ylmethyl)-1H-indole;

(R)-5-(2-methylaminosulfonylethyl)-3-(N-methylpyrrolidin-2-ylmethyl)-1H-indole;

(R)-5-(2-methylaminosulfonylethyl)-3-(pyrrolidin-2-ylmethyl)-1H -indole;

(R)-5-carboxamido-3-(N-methylpyrrolidin-2-ylmethyl)-1H-indole;

(R)-5-(2-methylsulfonylethyl)-3-(N-methylpyrrolidin-2-yl-methyl)-1H-indole;

(R)-5-(2-aminosulphonylethenyl)-3-(N-methylpyrrolidin-2-ylmethyl)-1H-indole;

(R)-5-(2-aminosulphonylethyl)-3-(N-methylpyrrolidin-2-ylmethyl)-1H-indole;

(R)-5-(2-N,N-dimethylaminosulphonylethyl)-3-(N-methylpyrrolidin-2-ylmethyl)-1H-indole;

(R)-5-(2-phenylsulphonylethyl)-3-(N-methylpyrrolidin-2-ylmethyl)-1H-indole [also known as (R)-5-(2-benzenesulphonylethyl)-3-(N-methyl-pyrrolidin-2-ylmethyl)-1H-indole];

(R)-5-(2-phenylsulphonylethyl)-3-(N-methylpyrrolidin-2-ylmethyl)-1H-indole hemisuccinate [also known as (R)-5-(2benzenesulphonylethyl)-3-(N-methyl-pyrrolidin-2-ylmethyl)-1H-indole hemisuccinate];

(R)-5-(2-phenylsulphonylethyl)-3-(N-methylpyrrolidin-2-ylmethyl)-1H-indole hydrobromide;

(R)-5-(2-ethylsulphonylethyl)-3-(N-methylpyrrolidin-2-ylmethyl)-1H-indole hemisuccinate;

(R)-5-(3-benzenecarbonylaminoprop-1-enyl)-3-(N-methylpyrrolidin-2-ylmethyl)-1H-indole;

(R)-5-(2-(4-methylphenylsulphonyl)ethyl)-3-(N-methylpyrrolidin-2-ylmethyl-1H-indole;

(R)-5-(3-methylsulphonylaminoprop-1-enyl)-3-(N-methylpyrrolidin-2-ylmethyl)-1H-indole;

(R)-5-(2-ethylsulphonylethyl)-3-(N-2-propylpyrrolidin-2-ylmethyl)-1H-indole;

(R)-5-(2-ethylsulphonylethyl)-3-(pyrrolidin-2-ylmethyl)-1H-indole;

(R)-5-(2-(4-methylphenylsulphonyl)ethenyl)-3-(N-methylpyrrolidin-2-ylmethyl)-1H-indole;

(R)-5-(2-methylsulfonamidoethyl)-3-(N-methylpyrrolidin-2-ylmethyl)-1H-indole;

(R)-5-(2-methylsulfonamidomethyl)-3-(N-methylpyrrolidin-2-ylmethyl)-1H-indole;

(R)-5-(methylaminosulfonylmethyl)-3-(N-methyl-pyrrolidin-2-ylmethyl)-1H-indole;

(R)-5-(methylaminosulfonylmethyl)-3-(N-methyl-pyrrolidin-2-ylmethyl)-1H-indole fumarate;

(R)-5-(methylaminosulfonylmethyl)-3-(pyrrolidin-2-ylmethyl)-1H-indole;

(R)-5-(aminosulphonylmethyl)-3-(N-methylpyrrolidin-2-ylmethyl)-1H-indole;

(R)-5-aminosulfonyl-3-(N-methylpyrrolidin-2-ylmethyl)-1H-indole; and (R)-7-Bromo-5-(methylaminosulfonylmethyl)-3-(N-methylpyrrolidin-2-ylmethyl)-1H-indole.

The following compounds are particularly preferred:

(R)-5-(2-phenylsulphonylethyl)-3-(N-methylpyrrolidin-2-ylmethyl)-1H-indole;

(R)-5-(methylaminosulfonylmethyl)-3-(N-methyl-pyrrolidin-2-ylmethyl)-1H-indole;

(R)-5-(aminosulfonylmethyl)-3-(N-methylpyrrolidin-2-ylmethyl)-1H-indole;

(R)-5-(methylaminosulfonylmethyl)-3-(pyrrolidin-2-ylmethyl)-1H-indole;

(R)-5-(methylaminosulfonylmethyl)-3-(N-methyl-pyrrolidin-2-ylmethyl)-1H-indole fumarate; and (R)-5-(2-phenylsulphonylethyl)-3-(N-methylpyrrolidin-2-ylmethyl)-1H-indole hydrobromide.

The following are other specific compounds of the present invention:

(R)-3-(N-methylpyrrolidin-2-ylmethyl)-1H-indole;

(R)-5-fluoro-3-(N-methylpyrrolidin-2-ylmethyl)-1H-indole;

(R)-5-acetylamino-3-(N-methylpyrrolidin-2-ylmethyl)-1H-indole;

(R)-5-benzyloxycarbonylamino-3-(N-methylpyrrolidin-2-ylmethyl)-1H-indole;

(R)-5-(2-aminocarbonylethyl)-3-(N-methylpyrrolidin-2-ylmethyl)-1H-indole;

(R)-5-aminocarbonylmethyl-3-(N-methylpyrrolidin-2-ylmethyl)-1H-indole;

(R)-5-methylsulfonamido-3-(N-methylpyrrolidin-2-ylmethyl)-1H-indole; and (R)-5-(aminosulfonylmethyl)-3-(pyrrolidin-2-ylmethyl)-1H-indole.

The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound of the formula I or a pharmaceutically acceptable salt thereof effective in treating such condition and a pharmaceutically acceptable carrier.

The present invention also relates to a pharmaceutical composition for treating disorders arising from deficient serotonergic neurotransmission (e.g., depression, anxiety, eating disorders, obesity, drug abuse, cluster headache, migraine, pain, and chronic paroxysmal hemicrania and headache associated with vascular disorders) comprising an amount of a compound of the formula I or a pharmaceutically acceptable salt thereof effective in treating such condition and a pharmaceutically acceptable carrier.

The present invention also relates to a method for treating a condition selected from hypertension, depression, anxiety, eating disorders, obesity, drug abuse, cluster headache, migraine, pain and chronic paroxysmal hemicrania and headache associated with vascular disorders comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The contemplated range for both pharmaceutical compositions and methods of use of the compound (R)-5-(methylaminosulfonylmethyl)-3-(N-methylpyrrolidin-2-ylmethyl)-1H-indole is from 0.1 µg to 200 mg.

The contemplated range for both pharmaceutical compositions and methods of use of the compound (R)-5-(aminosulfonylmethyl)-3-(N-methylpyrrolidin-2-ylmethyl)-1H-indole is from 0.1 µg to 200 mg.

The contemplated range for both pharmaceutical compositions and methods of use of the compound (R)-5-(methylaminosulfonylmethyl)-3-(pyrrolidin-2-ylmethyl)-1H-indole is from 0.01 µg to 200 mg.

The present invention also relates to a compound of the formula

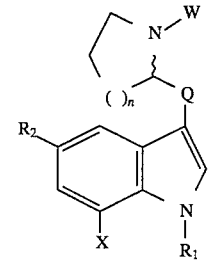

V wherein X is hydrogen, bromine, chlorine, or iodine; W is —$CO_2R_{11}$ or $R_3$; Q is $CH_2$ or C=O; n, $R_1$, $R_2$ and $R_3$ are as defined for formula I; and $R_{11}$ is selected from $C_1$ to $C_6$ alkyl, benzyl and aryl, wherein aryl is as defined above, with the proviso that when W is $R_3$, Q is C=O, and with the proviso that when X is bromine, chlorine, or iodine, W is —CO₂R₁₁ and Q is CH₂. The compounds of formula V are useful as intermediates in preparing compounds of the formula I.

Accordingly, one group of the foregoing intermediates comprises compounds of the formula

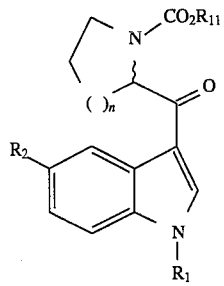                                II wherein n, R₁, R₂ and R₁₁ are as defined above and a second group of the foregoing intermediates comprises compounds of the formula

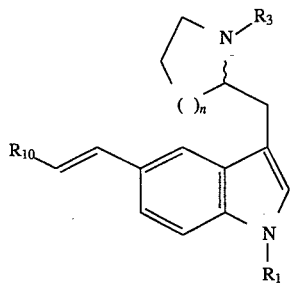                                III wherein n, R₁, R₃ and R₁₀ are as defined above.

The present invention also relates to a process for preparing a compound of the formula

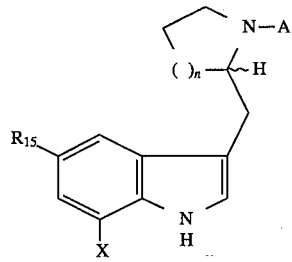                                (XVI)

wherein X is chlorine, bromine, or iodine; A is a first suitable nitrogen protecting group; R₁₅ is hydrogen, halogen, cyano, —OR₁₆, —(CH₂)ₘ—(C=O)NR₁₇R₁₈, —(CH₂)ₘ—SO₂NR₁₇R₁₈, —(CH₂)ₘ—NR₁₉(C=O)R₂₀, —(CH₂)ₘ—NR₁₉SO₂R₂₀, —(CH₂)ₘ—S(O)ₓR₂₀, —(CH₂)ₘ—NR₁₉(C=O)NR₁₇R₁₈, —(CH₂)ₘ—NR₁₉(C=O) OR₂₁, —CH=CH(CH₂)ᵧR₂₂, —(CH₂)ₘ—T, and a substituent of the formula

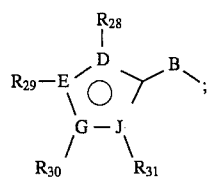

B represents a direct bond, C₁–C₄ alkyl, or C₁–C₄ alkenyl; D, E, G, and J are each independently oxygen, sulfur, nitrogen or carbon, provided that at least one of D, E, G, and J is nitrogen; R₂₈, R₂₉, R₃₀, and R₃₁ are each independently hydrogen, C₁–C₆ alkyl, aryl, C₁–C₃ alkylaryl, C₁–C₃ alkylheteroaryl, halogen, cyano, trifluoromethyl, nitro, —OR₃₂, —NR₃₂R₃₃, —(CH₂ₘ)OR₃₂, —SR₃₂, —SO₂NR₃₂R₃₃, —NR₃₂SO₂R₃₃, —NR₃₂CO₂R₃₃, —CONR₃₂R₃₃, or —CO₂R₃₂; one of R₂₈ and R₂₉, R₂₉ and R₃₀, or R₃₀ and R₃₁ may be taken together to form a five- to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O, or S; R₃₂ and R₃₃ are each independently hydrogen, C₁ to C₆ alkyl, —(CH₂)qR₃₄, C₁ to C₃ alkylaryl, or aryl; R₃₂ and R₃₃ may be taken together to form a C₄–C₇ alkyl ring; R₃₄ is cyano, trifluoromethyl, or C₁–C₄ alkoxy; R₁₆ is hydrogen, C₁, to C₆ alkyl, or aryl; T is

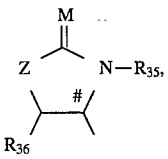                                (i)

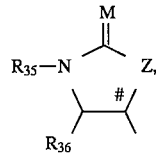                                (ii)

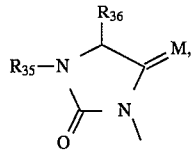                                (iii)

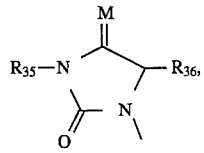                                (iv)

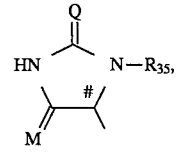                                (v)

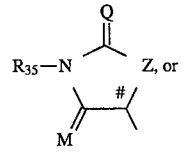                                (vi)

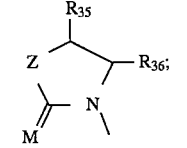                                (vii)

M and Q are each independently oxygen or sulfur; Z is —O—, —S—, —NH, or —CH₂; R₃₅ and R₃₆ are each independently hydrogen, C₁ to C₆ alkyl, aryl, C₁ to C₃ alkylaryl, or C₁ to C₃ alkylheteroaryl; R₂₂ is —(C=O) NR₂₃R₂₄, —SO₂NR₂₃R₂₄, —NR₂₅(C=O)R₂₆, —NR₂₅SO₂R₂₆, —NR₂₅(C=O)NR₂₃R₂₄, —S(O)ₓR₂₆ or —NR₇(C=O) OR₂₇; R₁₇, R₁₈, R₂₃, and R₂₄ are each independently hydrogen, C₁ to C₆ alkyl, aryl, or C₁ to C₃ alkyl-aryl, or R₁₇ and R₁₈ or R₂₃ and R₂₄ maybe taken together to form a four- to six-membered ring; $R_{19}$, $R_{20}$, $R_{21}$, $R_{25}$, $R_{26}$, and $R_{27}$ are each independently hydrogen, $C_1$ to $C_6$ alkyl, aryl, or $C_1$ to $C_3$ alkyl-aryl; y is 0, 1, or 2; x is 1 or 2; m is 0, 1, 2, or 3; n is 0, 1 or 2; q is 1, 2, or 3; and the above aryl groups and the aryl moieties of the above alkylaryl groups are independently selected from phenyl and substituted phenyl, wherein said substituted phenyl may be substituted with one to three groups selected from $C_1$ to $C_4$ alkyl, halogen, hydroxy, cyano, carboxamido, nitro, and $C_1$ to $C_4$ alkoxy, comprising, performing a transition metal catalyzed cyclization on a compound of the formula

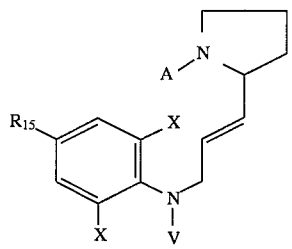

(XVII)

wherein $R_{15}$, A, and X are as defined above and V is a second suitable nitrogen protecting group.

The process is preferable used where X is bromine.

The compounds of formula XVI are useful in preparing the compounds of formula I, as well as preparing the 5-$HT_{1D}$ agonists disclosed in International Application Nos. WO 93/18032 (published Sep. 16, 1993) and WO 93/20073 (published Oct. 14, 1993).

DETAILED DESCRIPTION OF THE INVENTION

Compounds of formula I are prepared by hydride reduction of a compound of the formula

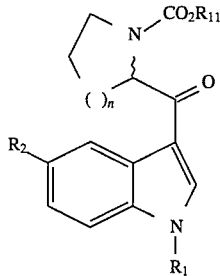

II wherein $R_1$, $R_2$, n and $R_{11}$ are as defined above with a hydride reducing agent in an inert solvent. Suitable hydride reducing agents include lithium aluminum hydride, diborane, lithium borohydride and sodium borohydride. The preferred reagent is lithium aluminum hydride. Suitable solvents include ethers, such as diethyl ether, tetrahydrofuran, 1,4-dioxane and 1,2-dimethoxyethane. The preferred solvent is tetrahydrofuran. The reaction is conducted at a temperature of about 30° C. to about 100° C., preferably about 65° C. to about 70° C.

Compounds of formula I are also prepared by catalytic reduction of a compound of the formula

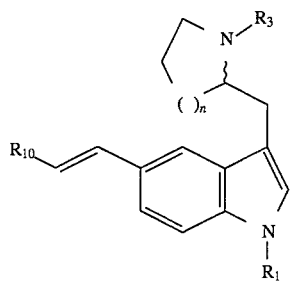

III wherein $R_1$, $R_3$, n and $R_{10}$ are as defined above under an atmosphere of hydrogen, preferably at a pressure of about 1 to about 3 atmospheres, or using a hydrogen source such as ammonium formate or formic acid in an inert solvent. Suitable catalysts include palladium on carbon, Raney nickel, platinum oxide, rhodium, and ruthenium. The preferred catalyst is palladium on carbon. Suitable solvents include $C_1$ to $C_6$ alcohols, N,N-dimethylformamide, ethyl acetate, acetonitrile, and acetone. The preferred solvents are ethanol and acetone. The reaction is conducted at a temperature of about 0° C. to about 60° C., most preferably at about 25° C.

Compounds of formula I are also prepared by alkylation of compounds of formula I where $R_3$=H and $R_2$ and $R_1$, are as defined for formula I with alkyl halides in the presence of a base in an inert solvent. Suitable alkyl halides include alkyl halides of the formula $R^3$—Halide where the halide is chloride, bromide and iodide. The preferred halide is iodide, or bromide in the presence of a suitable iodide source such as sodium iodide. Suitable bases include tertiary amines and inorganic bases. The preferred base is sodium carbonate. Suitable solvents include N,N-dimethylacetamide, N,N-dimethylformamide, dimethoxyethane, tetrahydrofuran, dichloromethane, and acetonitrile. The preferred solvent is N,N-dimethylacetamide. The reaction is conducted at a temperature of about 0° C. to about 150° C., preferably at about 120° C.

Compounds of formula I are also prepared by alkylation of compounds of formula I where $R_3$=H and $R_2$ and $R_l$ are as defined from formula I, with aldehydes and ketones in the presence of a hydride source. Suitable aldehydes are of the formula $R_{37}$CHO where $R_{37}$ is $C_l$ to $C_5$ alkyl. The preferred aldehyde is formaldehyde. Suitable ketones are of the formula $R_{38}$(C=O)$R_{39}$ where $R_{38}$ and $R_{39}$ are each independently $C_1$ to $C_5$ alkyl provided that the total number of carbons in both $R_{38}$ and $R_{39}$ is at most five. Suitable hydride sources include formic acid derivatives, phosphorous acids, and alkali metal borohydrides. The preferred hydride source are formic acid, sodium triacetoxyborohydride, sodium cyanoborohydride and the monosodium salt of phosphorous acid, with the more preferred hydride source being the monosodium salt of phosphorous acid (H. Loibner, Tet. Lett. (1984) p. 2535). The reaction is usually conducted at a temperature of from about ambient temperature (about 27° C.) to about reflux temperature, preferably 60° C. (with preferred solvent of tetrahydrofuran (hereinafter referred to as THF)). Suitable solvents in which the reaction can be run include aqueous THF, aqueous dioxane, water plus one of the lower alcohols (e.g., methanol or ethanol), ethers, esters (ethyl acetate), or halogenated hydrocarbons (dichloromethane or chloroform), or acetonitrile, preferably aqueous THF.

As an alternative to the process in the previous paragraph, compounds of formula can be prepared via a reductive amination using an aldehyde or ketone, of the formulae described in the previous paragraph, along with a transition metal catalyst, and a hydrogen source in an inert solvent. Suitable catalysts include palladium on carbon, Raney nickel, platinum oxide, and palladium hydroxide on carbon. The preferred catalyst is palladium hydroxide on carbon. Suitable hydrogen sources include hydrogen gas, ammonium formate, and formic acid. Hydrogen gas at a pressure of from about one to about three atmospheres is the preferred hydrogen source. Three atmospheres of hydrogen gas is the preferred pressure. Suitable solvents include $C_1$ to $C_4$ alcohols, acetonitrile, N,N-dimethylformamide, and N-methylpyrrolidine. Ethanol is the preferred solvent. The reaction is usually conducted at a temperature of from about 25° C. to about 100° C., preferably about 25° C. to about 50° C.

The compounds of formula II can be prepared by reacting a magnesium salt of an indole derivative of the formula

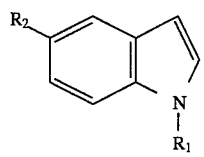

IV wherein $R_1$ and $R_2$ are defined above, with the acid chloride of an N—$CO_2R_{11}$-proline, N—$CO_2R_{11}$-azetidine-2-carboxylic acid, or N—$CO_2R_{11}$-pipecolinic acid (R, S, or racemate), wherein $R_{11}$ is defined as above, in a ratio of from about 1:1 to about 2:1, preferably 2:1 (indole magnesium salt: acid chloride compound). The indole magnesium salt is first prepared from the reaction of an indole of formula IV with an alkyl or aryl magnesium halide, preferably ethylmagnesium bromide. The reaction is generally conducted in an inert solvent at a temperature between about −30° C. and about 65° C., preferably at about 25° C. Suitable solvents include diethyl ether, tetrahydrofuran, and other alkyl ethers and dichloromethane with toluene. The preferred solvents are diethyl ether and dichloromethane with toluene. The acid chloride of proline, azetidine-2-carboxylic acid, or pipecolinic acid is prepared in a separate reaction vessel by reaction of the N—$CO_2R_{11}$-proline, N—$CO_2R_{11}$-azetidine-2-carboxylic acid, or N—$CO_2R_{11}$-pipecolinic acid (R, S, or racemate), with oxalyl chloride in methylene chloride at about −10° C. to about 25° C. (*Helv. Chim. Acta*, 1920 (1976)). Suitable solvents include diethyl ether, tetrahydrofuran, other alkyl ethers, and methylene chloride. The proline, azetidine-2-carboxylic acid, or pipecolinic acid is N-substituted with a protecting group to avoid reaction of the nitrogen with the acid chloride when it is formed. Suitable protecting groups are substituted-aryl or substituted-alkyl carbamates (e.g. benzyloxycarbonyl). Preferably, a solution of the N—$CO_2R_{11}$-proline acid chloride in an inert solvent (e.g., diethyl ether) is added slowly to the solution of the magnesium salt of an indole of formula IV at a temperature of about −30° C. to about 50° C., preferably at about 25° C.

The compounds of formula III can be prepared by reacting a compound of formula

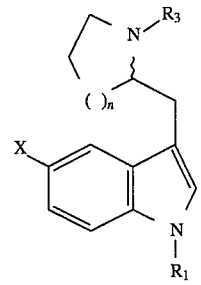

V where in $R_1$, $R_3$ and n are defined as above and X is chlorine, bromine or iodine (preferably bromine), with a compound containing a vinyl group (e.g. ethyl vinyl sulfone or N-methylvinylsulfonamide) in the presence of a palladium catalyst, a triarylphosphine and a base in an inert solvent. Suitable catalysts include palladium (II) salts, preferably palladium (II) acetate. Suitable solvents include acetonitrile, N,N-dimethylformamide, tetrahydrofuran and N,N-dimethylformamide with 1,2-dimethoxyethane. The preferred solvents are acetonitrile and N,N-dimethylformamide. The preferred triarylphosphine is tri-o-tolylphosphine. Suitable bases include trisubstituted amines. The preferred base is triethylamine. The reaction is conducted at a temperature of about 25° C. to 150° C., most preferably at about 80° C.

The reaction in the previous paragraph can also be preformed on the compound of formula V where $R_1$ is a suitable nitrogen protecting group, using those known in the art. The preferred groups are electron withdrawing groups, preferably acetyl. Once the above reaction is complete, the corresponding compound of formula III with the aforementioned protecting group can be isolated by crystallization. The protecting group is then removed using methods known in the art to result in the compound of formula III defined previously on page 11. The procedure described in this paragraph differs from that described in the previous paragraph in that this procedural step eliminates the need to use a column to isolate the desired compound.

Compounds of formula I and intermediates to compounds of formula I can be prepared by hydride reduction of a compound of the formula

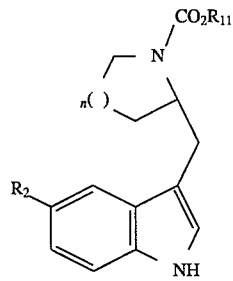

VI wherein $R_2$, n, and $R_{11}$ are as defined above with a hydride reducing agent in an inert solvent. Suitable hydride reducing agents include lithium aluminum hydride, diborane, lithium borohydride, and sodium amide. The preferred reagent is lithium aluminum hydride. Suitable solvents include ethers, such as diethyl ether, tetrahydrofuran, 1,4-dioxane and 1,2-dimethoxyethane. The preferred solvent is tetrahydrofuran. The reduction is conducted at a temperature of about 30° C. to about 100° C., preferably about 65° C. to about 70° C.

Compounds of formula I and intermediates to compounds of formula I can also be prepared by catalytic reduction of a compound of the formula

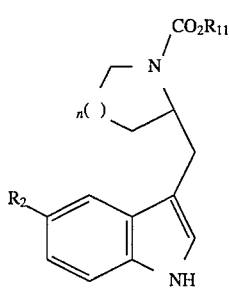

VI wherein $R_2$, n, and $R_{11}$ are as defined above under an atmosphere of hydrogen, preferably at a pressure of about 1 to 3 atmospheres, or using a hydrogen source such as ammonium formate of formic acid in an inert solvent. Suitable catalysts include palladium on carbon, Raney nickel, and platinum oxide. The preferred catalyst is palladium on carbon. Suitable solvents include $C_1$ to $C_6$ alcohols, N,N-dimethylformamide, ethyl acetate, and acetonitrile. The preferred solvent is ethanol. The reaction is conducted at a temperature of about 0° C. to about 60° C., preferably at about 25° C.

Compounds of formula VI can be prepared by the transition metal catalyzed cyclization of a compound of the formula

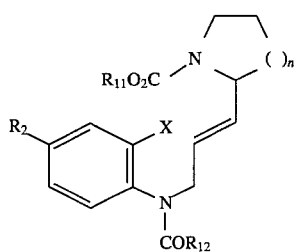

VII wherein $R_2$, n, and $R_{11}$ are as defined above, and X is chlorine, bromine, or iodine (preferably bromine or iodine), and $R_{12}$ is —$OR_{11}$ as defined above or alkyl, aryl, or trifluoromethyl (preferably trifluoromethyl) in a suitable inert solvent with a phase transfer catalyst and a base. Suitable catalysts include palladium salts such as palladium (II) acetate or palladium (II) chloride (preferably palladium acetate) and rhodium salts, such as tris(triphenyl)rhodium (I) chloride. Suitable solvents include N,N-dimethylformamide, N,N-dimethylformamide with dimethoxyethane, acetonitrile, and N-methylpyrrolidine. The preferred solvents are N,N-dimethylformamide and N,N-dimethylformamide with dimethoxyethane. Suitable phase transfer catalysts include tetraalkylammonium halides, preferably tetra-n-butylammonium chloride. Suitable bases include tertiary amines, sodium hydrogen carbonate, and sodium carbonate. The preferred base is triethylamine. The reaction is conducted at a temperature of about 80° C. to about 180° C., preferably about 150° C. to 160° C.

Compounds of formula VI can also be prepared by hydride reduction of a compound of the formula

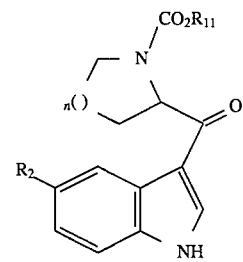

II wherein $R_2$, n, and $R_{11}$ are as defined above with a hydride reducing agent in an inert solvent. Suitable hydride reducing agents include lithium borohydride, sodium borohydride, and sodium cyanoborohydride. The preferred reagent is lithium borohydride. Suitable solvents include ethers, such as diethyl ether, tetrahydrofuran, 1,4-dioxane and 1,2-dimethoxyethane. The preferred solvent is tetrahydrofuran. The reduction is conducted at a temperature of about 30° C. to about 100° C., preferably about 65° C. to about 70° C.

Compounds of formula VII can be prepared by the Mitsunobu coupling reaction of compounds of formulas

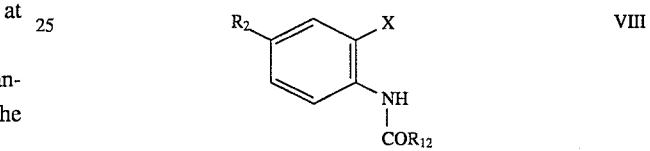

VIII

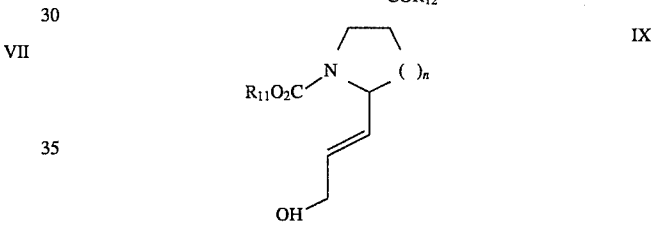

IX wherein $R_2$, n, $R_{11}$, and $R_{12}$ are as defined above using a phosphine and an azodicarboxylate in a suitable solvent. Suitable phosphines include trialkylphosphines and triarylphosphines, preferably triphenylphosphine. Suitable azodicarboxylates include dialkyl azodicarboxylates, preferably diethyl azodicarboxylate. Suitable solvents include methylene chloride, ethers, including tetrahydrofuran, diethyl ether, and 1,4-dioxane, N-N-dimethylformamide and acetonitrile. The preferred solvent is tetrahydrofuran. The reaction is conducted at a temperature of about 0° C. to about 65° C., most preferably at about 25° C.

Compounds of formula VIII, if not available commercially, can be prepared by reacting a compound of formula X

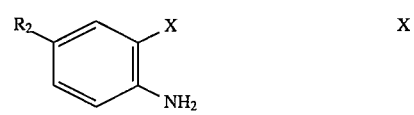

X wherein $R_2$ and X are as defined above with the acid chloride or the symmetrical anhydride of $R_{12}CO_2H$ in a suitable solvent with an suitable base. The preferred acid chloride or anhydride is trifluoroacetic anhydride. Suitable solvents include ethers, including tetrahydrofuran, diethyl ether and 1,4-dioxane, methylene chloride, and chloroform. The preferred solvent is methylene chloride. Suitable bases include triethylamine, pyridine, and sodium hydrogen carbonate.

The preferred base is pyridine. The reaction is conducted at a temperature of about 0° C. to about 65° C., preferably at about 25° C.

Compounds of formula X, if not available commercially, can be prepared by reacting a compound of formula XI

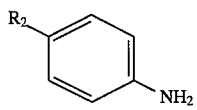   XI wherein $R_2$ is as defined above with either chlorine, bromine, or iodine in a suitable solvent with a suitable base. Reaction with bromine is preferred. Suitable solvents include $C_1$–$C_6$ alcohols, methylene chloride, methanol with methylene chloride, chloroform, or carbon tetrachloride. The preferred solvents are methanol and methanol with methylene chloride. Suitable bases include triethylamine, pyridine, sodium carbonate, and sodium hydrogen carbonate. The preferred base is sodium hydrogen carbonate. The reaction is conducted at a temperature of about 0° C. to about 65° C., preferably at about 25° C.

Compounds of the formula IX can be prepared from hydride reduction of a compound of formula XII

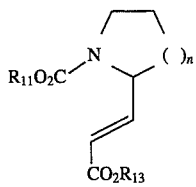   XII wherein $R_{11}$ is defined as above and $R_{13}$ is $C_1$–$C_6$ alkyl, aryl, or alkylaryl with a hydride reducing agent in an inert solvent. Suitable hydride reducing agents include lithium aluminum hydride, lithium borohydride, sodium borohydride, and diisobutylaluminum hydride. The preferred reagent is diisobutylaluminum hydride. Suitable solvents include ethers, such as diethyl ether, tetrahydrofuran, 1,4-dioxane and 1,2-dimethoxyethane. The preferred solvent is tetrahydrofuran. The reduction is conducted at a temperature of about −100° C. to about 0° C., preferably at about −80° C. to about −60° C., more preferably at about −70° C. to about −60° C.

Compounds of the formula XII can be prepared from the Wittig reaction in a suitable solvent involving compounds of the formulas

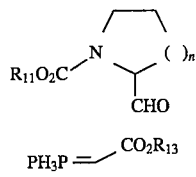   XIII

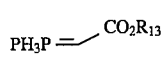   XIV wherein $R_{11}$ and $R_{13}$ are defined as above. Suitable solvents include ethers such as diethyl ether, tetrahydrofuran, and 1,4-dioxane. Tetrahydrofuran is the preferred solvent. The reaction is conducted by adding the reagents at a temperature of about −78° C. to about 30° C. preferably either at about −78° C. to minimize possible racemization, or at about room temperature should racemization not be problematic. The reagent solution is then warmed to room temperature, if necessary, and then heated to the reflux temperature of the solvent (67° C. reflux temperature of preferred solvent THF).

Compounds of the formula XIII can be prepared as outlined in S. Kiyooka, et al., *J. Org. Chem.*, 5409 (1989) and Y. Hamada, et al., *Chem. Pharm. Bull.*, 1921 (1982).

Compounds of the formula XIV are either commercially available or can be prepared as outlined in L. Fieser and M. Fieser, *Reagents for Organic Synthesis*, John Wiley and Sons, New York, Vol. 1, p. 112 (1967).

Compounds of formula I (which include compounds claimed in the present application as well as in international published application nos. WO 93/18032 and WO 93/20073) are also prepared by catalytic reduction of a compound of the formula

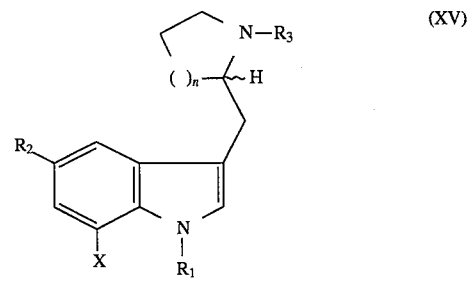   (XV)

wherein $R^3$ is as defined above or is a substituent of the formula —$CO_2$—$R_q$, $R_q$ is benzyl or substituted benzyl, and where $R^1$, $R^2$ and n are as defined above and X is chlorine, bromine or iodine (preferably bromine or iodine) under an atmosphere of hydrogen, preferably at a pressure of about 1 to 4 atmospheres, or using a hydrogen source such as ammonium formate or formic acid in an inert solvent. Suitable catalysts include 20% palladium (II) hydroxide on carbon, palladium on carbon, Raney nickel, platinum oxide, rhodium and ruthenium. The preferred catalyst is 20% palladium (II) hydroxide on carbon. Suitable solvents include $C_1$ to $C_6$ alcohols, N,N-dimethylformamide, ethyl acetate and acetonitrile. The preferred solvent is ethanol. The reaction is generally conducted at a temperature of about 0° C. to about 60° C., most preferably at about 25° C.

Compounds of formula XV are prepared by hydride reduction of a compound of the formula

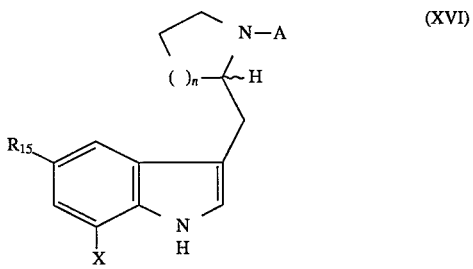   (XVI)

wherein $R_2$, n and A are as defined above and X is chlorine, bromine or iodine (preferably bromine or iodine) with a hydride reducing agent in an inert solvent, as described for the hydride reduction of compounds of formula VI on page 15 and 16 of the specification. Examples of A include t-butoxycarbonyl(BOC) and benzyloxycarbonyl(CBZ), preferably CBZ (See T. W. Green, *Protecting Groups in Organic Synthesis*, John Wiley & Sons (1981) pp 218–287). A side product of this reaction can be a compound of formula I where X is hydrogen and $R_3$ is methyl.

Compounds of formula XVI can be prepared by the transition metal catalyzed cyclization of a compound of the formula

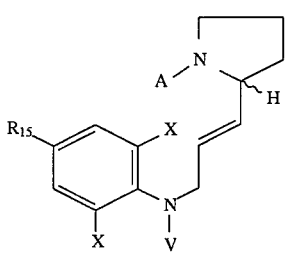

(XVII)

wherein $R_2$, n, A, and V are as defined above, and X is chlorine, bromine or iodine (preferably bromine or iodine) and $R_{12}$ is —$OR_{11}$ as defined above or alkyl, aryl, or trifluoromethyl (preferably trifluoromethyl) in a suitable inert solvent with a phase transfer catalyst, a base and a suitable transition metal catalyst, as described for the transition metal catalyzed cyclization of a compound of formula VII on pages 16 to 17 of the specification. Examples of V include t-butoxycarbonyl(BOC), benzyloxycarbonyl(CBZ), and trifluoroacetyl, preferably trifluoromethylacetyl (See T. W. Green, *Protecting Groups in Organic Synthesis*, John Wiley & Sons (1981) pp 218–287).

Compounds of formula XVII can be prepared by the Mitsunobu coupling reaction of compounds of formulae

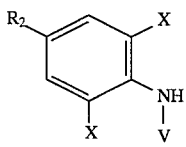

(XVIII)

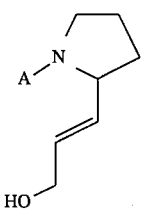

(XIX)

wherein $R_2$, n, $R_{11}$, $R_{12}$ and X are as defined above using a phosphine and an azodicarboxylate in a suitable solvent, as described for the Mitsunobu coupling reaction of compounds of formulas VIII and IX on pages 17 and 18 of the specification.

Compounds of formula XVIII, if not available commercially, can be prepared by reacting a compound of formula

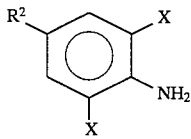

(XX)

wherein $R_2$ and X are as defined above with the acid chloride or the symmetrical carboxylic anhydride of the formula V—O—V, where V is as defined above, in a suitable solvent with a suitable base, as described for the preparation of compounds of formula VIII on pages 18 and 19 of the specification.

Compounds of formula XX, if not available commercially, can be prepared by reacting a compound of formula

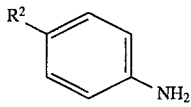

(XXI)

wherein $R_2$ is as defined above with either chlorine, bromine or iodine in a suitable solvent with a suitable base, as described for the preparation of compounds of formula X on page 17 of the specification, except that two equivalents of halogen are required.

Compounds of the formula XXI, if not commercially available, can be prepared as described for the preparation of the compounds of formula XI on page 19 of the specification.

Compounds of formula I are also prepared by reaction of a compound of formula

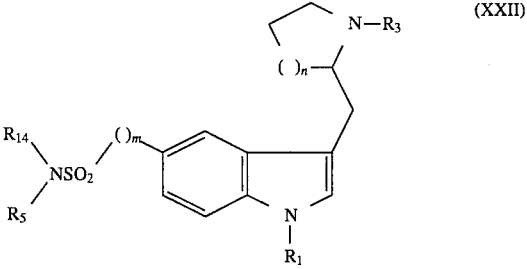

(XXII)

wherein $R_1$, $R_3$, $R_5$, m and n are as defined above and $R_{14}$ is a suitable sulfonamide N protecting group such as t-butyl or benzyl, preferably t-butyl. Suitable conditions for removing such a protecting group are known in the art, for example, when $R_{14}$ is t-butyl, treatment with a strong acid such as trifluoroacetic acid or hydrochloric acid. In the case of trifluoroacetic acid, the acid can be used neat, or in a suitable inert solvent such as diethyl ether or dichloromethane.

Alternatively, protection of the indole ring in situ can be achieved by initial treatment with an indole-N-1 acylating agent, such as acetic anhydride or acetyl chloride, using procedures known in the art. For example where acetic anhydride is used, the acylating agent can be used neat, or in a suitable inert solvent, such as diethyl ether or dichloromethane. This is followed by removal of the sulfonamide N protecting group, $R_{14}$, as outlined above and then hydrolytic removal of the indole-1-acyl protecting group using a suitable hydrolytic agent known in the art, such as a hydroxide or carbonate salt, preferably potassium carbonate in a suitable solvent. Suitable solvents include $C_1$ to $C_6$ alcohols, preferably methanol or ethanol. The above process can be carried out as a one pot procedure to afford compounds of formula I directly from compounds of formula XXII.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. If necessary, upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R_2$ contains a carboxylate, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The preferred salt of (R)-5-(2-phenylsulphonylethyl)-3-(N-methylpyrrolidin-2-ylmethyl)-1H-indole in solid dosage forms is the crystalline, polymorphic α-form of the hydrobromide salt of the compound. The α-form is crystalline, of suitable melting point, non-hygroscopic, compressible and possesses solid-state stability, coupled with acceptable solubility and dissolution behavior. The α-form can be produced using methods know in the art, including, for example, by any of the following three routes. The first route involves treatment of (R)-5-(2-phenylsulphonylethyl)-3-(N-methylpyrrolidin-2-ylmethyl)-1H-indole in a suitable solvent, preferably acetone, at room temperature, with an aqueous solution of hydrogen bromide (e.g., 49%), followed by crystallization of the isolated crude oil from a suitable solvent, preferably 2-propanol, thus affording the α-form. The second route involves first forming the β-form by treatment of (R)-5-(2-phenylsulphonylethyl)-3-(N-methylpyrrolidin-2-ylmethyl)-1H-indole in a suitable solvent, preferably acetone or a ether solvent such as tetrahydrofuran or 1,2-dimethoxyethane, more preferably 1,2-dimethoxyethane, at a temperature of from 0 to 10° C., with an aqueous solution of hydrogen bromide (e.g., 49%), furnishing the β-form. Crystallization of the β-form from a suitable solvent, preferably aqueous acetone, followed by slurrying of the resulting mixture, gives the desired α-form. The third route involves treatment of (R)-5-(2-phenylsulphonylethyl)-3-(N-methylpyrrolidin-2-ylmethyl)-1H-indole in a suitable solvent, preferably acetone, at from 0° to 5° C. with an aqueous solution of hydrogen bromide (e.g., 62%) and then slurrying of the reaction mixture, optionally followed by heating under reflux, cooling and further slurrying, provides the required α-form.

The preferred salt of (R)-5-(methylaminosulfonyl-methyl)-3-(N-methylpyrrolidin-2-ylmethyl)-1H-indole is the fumarate salt thereof, which can be prepared by combining (R)-5-(methylaminosulfonyl-methyl)-3-(N-methylpyrrolidin-2-ylmethyl)-1H-indole with about one equivalent of fumaric acid in methanol. The methanol is then distilled out and replaced with an equal amount of acetonitrile, thus causing crystallization of the salt.

The compounds of the formula I and the pharmaceutically acceptable salts thereof (hereinafter, also referred to as the active compounds of the invention) are useful psychotherapeutics and are potent serotonin (5-HT$_1$) agonists and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators.

The active compounds of the invention are evaluated as anti-migraine agents by testing the extent to which they mimic sumatriptan in contracting the dog isolated saphenous vein strip (P. P. A. Humphrey et al., *Br. J. Pharmacol.*, 94, 1128 (1988)). This effect can be blocked by methiothepin, a known serotonin antagonist. Sumatriptan is known to be useful in the treatment of migraine and produces a selective increase in carotid vascular resistance in the anaesthetized dog. It has been suggested (W. Fenwick et al., *Br. J. Pharmacol.*, 96, 83 (1989)) that this is the basis of its efficacy.

EC$_{50}$'s for the compounds of formula I tested for contracting the dog isolated saphenous vein strip, using the procedure referred to above, were less than $10^{-4}$M.

The active compounds of the present invention are also evaluated via the inhibition of plasma protein extravasation response within the dura mater of guinea pigs following unilateral electrical trigeminal ganglion stimulation. The extent to which they mimic sumatriptan, in terms of both potency and efficacy, is determined in this assay. The procedure is performed on male Hartley guinea pigs (200–250 g, Charles River Laboratories, Wilmington, Mass., U.S.A.) as described in Markowitz et al., *J. Neurosci.*, 7 (12), 4129–4136 (1987) and also in Lee, et al., Brain Research, 626, 303–305 (1993). The procedure briefly consists of placing pentobarbitone-anesthetized animals in a stereotaxic frame. $^{125}$I-BSA (bovine serum albumin) (50 µCi/kg$^{-1}$) is first injected into the femoral vein, followed 5 minutes later by drug or vehicle. Bipolar electrodes are then lowered into the trigeminal ganglia, and the right ganglion is stimulated for 5 minutes (1.2 mA, 5 Hz, 5 msec). The animal is then perfused with saline through the left cardiac ventricle and sacrificed, and the dura mater is dissected, weighed, and counted for radioactivity. Cpm/mg wet weight values are determined for the right vs left dura mater, and a ratio for the stimulated vs unstimulated sides is generated for each animal. Unpaired student's t-test is used to statistically compare these ratio values in respective groups treated with vehicle or drug. The M.E.D. (minimally effective dose) for a given compound is the lowest dose for which the mean value of this ratio is significantly lower than that obtained for the vehicle-treated group. The effect of the drugs in these assays can be partially blocked by metergoline, a known serotonin antagonist.

A similar procedure to the one described above can be performed on rats, as described in Matsubara, et al., *Br. J. Pharmacol.*, 104, 3 (1991).

The active compounds of the invention may also be useful in the treatment of headache associated with meningeal irritation, including bacterial, fungal, viral, parasitic, and chemical meningitis, acquired immune deficiency syndrome (AIDS) meningovascular inflammation, and subarachnoid hemorrhage. [See W. S. Lee, et al., Evidence Using Conformationally Restricted Sumatriptan Analogues, CP-122, 288 and CP-122,638, that 5-HT$_{1D}$ Receptors Do Not Mediate Blockade of Neurogenic Inflammation, 23rd Annual Meeting of the Society for Neuroscience, Washington, D.C., Nov. 7–12, 1993, Abstract #565.6; K. Nozaki, et al., CP-93, 129, Sumatriptan, Di-hydroergotamine Block c-fos Expression Within Rat Trigeminal Nucleus Caudalis Caused by Chemical Stimulation of The Meninges, *Br. J. Pharmacol.* (1992), 106, 409; and Lee, et al, *Brain Research,* 626, 303–305 (1993).]

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

The compounds of the present invention may be useful in the treatment of a considerable number of diseases. These include dermatological disorders, including psoriasis; eczema and atopic eczematous dermatitis; intractable itch (pruritus), including itch associated with liver cirrhosis, cancer and haemodialysis; burns and scalds; sunburn; insect bites, urticaria and sweat gland abnormalities. Other dermatological disorders include bullous penphgoid, photo dermatoses, skin blisters, adult acne, chicken pox and dermatitis herpetifunus.

Other diseases which may be treated with the compounds of the present invention are peripheral neurophathies including postherpetic neuralgia, diabetic neuropathies such as peripheral polyneuropathy and radiculopathy; causalgia and reflex sympathetic dystrophy; post-mastectomy neuralgia; post-surgical neuralgia and pain; vulvar vestibulitis; phantom limb pain; thalamic syndrome (central post-stroke pain); temporo mandibular joint syndrome; metarsalgia (Morton's neuralgia); and neurogenic pain from nerve compression caused, for example, by a prolapsed intervertebral disc or carpal and tarsal tunnel syndromes.

The above-mentioned compounds may also be useful in alleviating arthritis, including osteoarthritis, rheumatoid arthritis, systemic lupus erythrematosus, fibromyalgia, ankylosing spondilitis and tendinitis. They are also effective against gastrointestinal and urogenital diseases including cystitis, gastroesophargeal reflux, gastritis, urge continence, inflammatory bowel disease and irritable bowel syndrome; they are effective in regulatory gastrointestinal tract motility.

The compounds may also be used in the treatment of headache associated with substances or their withdrawal (e.g. drug withdrawal), tension headache, pediatric migraine and prophylaxis of migraine and post-traumatic dysautonomic cephalgia.

They may also be used for treating orofacial pain (for example toothache and pain of dental origin, earache, TMJ pain, sinus pain, myofacial pain, non-arthritic and non-musculoskeletal cervical pain), mouth ulcers, Meniere's disease and atypical facial neuralgia, and also allergic and chronic obstructive airways diseases such as rhinitis, conjunctivitis, bronchial oedema, bronchial asthma, neurological pulmonary oedema (adult respiratory disease syndrome), anaphylaxis and angioedema. The compounds are also efficacious in treating ocular pressure or glaucoma and ocular inflammation.

It is believed that the compounds of formula I and their salts are efficacious against emesis caused by several factors not associated with migraine, including emesis induced by anaesthesia, cancer chemotherapy and by motion (seasickness, space and airsickness).

The activity of the compounds as anti-emetics may be demonstrated by the method of Tatersall et al and Bountra et al (*European Journal of Pharmacology,* 250 (1993) R5 and 249 (1993) R3-R4). In this method the extent to which they reduce the latency or the number of retches and/or vomits induced by emetogins in the conscious ferret compared to vehicle - treated animals is measured. It is found that the compounds are effective against emesis caused by a wide range of emetogeny, extending from local irritants to anti-cancer radiation treatment.

Compounds of formula I described above but for the fact that one or more hydrogen, oxygen, or nitrogen atoms are replaced by radioactive isotopes thereof. Such radiolabelled compounds are useful as research or diagnostic tools in metabolism pharmacokinetic studies and in binding assays. Specific applications could include the discovery of novel receptors involved in the pathogenesis of neurogenic inflammation, leading to diseases such as migraine. Isotopes included among the radiolabelled forms of these compounds are the $^3$H and $^{14}$C isotopes thereof (e.g. the 7-$^2$H, 7-$^3$H, and N-($^3$H$_3$)-methyl[i.e., having CT$_3$ on the pyrrolidinyl nitrogen]), for example, (R)-N-methyl-3-(1-methyl-2-pyrrolidinylmethyl)-1H-[7-$^2$H]-indol-5-yl]methanesulfonamide, (R)-N-methyl-[3-(1-methyl-2-pyrrolidinylmethyl)-1H-[7-$^3$H]-indol-5-yl]methanesulfonamide, and (R)-N-methyl-[3-(1-($^3$$_3$H)methyl-2-pyrrolidinylmethyl)-1H-indol-5-yl]methanesulphonamide. The 7-$^2$H and 7-$^3$H derivatives of the invention can be prepared by the deuteration or tritiation of the corresponding 7-bromo-derivative, preferably in the presence of pre-reduced Pearlman's catalyst in an organic solvent such as ethanol. The $^3$H$_3$ (i.e., tri-tritiated derivative) can be prepared by the reaction of the corresponding compound having no substitution on the pyrrolidinyl nitrogen, preferably as a salt such as the hydrobromide with $^3$H$_3$ methyl iodide, preferably in the presence of a base such as potassium carbonate.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the compound (R)-5-(methylaminosulfonylmethyl)-3-(N-methylpyrrolidin-2-ylmethyl)-1H-indole for oral, parenteral or buccal administration to the average adult human for the treatment of the conditions referred to above (e.g., migraine) is 0.1 µg to 200 mg of the active ingredient per unit dose which could be administered, for example, 1 to 4 times per day. In one embodiment, the pharmaceutical composition includes 0.1 µg to less than 0.1 mg of the active ingredient per unit dose, and in another embodiment, the pharmaceutical composition includes 0.1 µg to 0.09 mg of the active ingredient per unit dose.

A proposed dose of the compound (R)-5-(aminosulfonylmethyl)-3-(N-methylpyrrolidin-2-ylmethyl)-1H-indole for oral, parenteral or buccal administration to the average adult human for the treatment of the conditions referred to above (e.g., migraine) is 0.1 µg to 200 mg of the active ingredient per unit dose which could be administered, for example, 1 to 4 times per day. In one embodiment, the pharmaceutical composition includes 0.1 µg to less than 0.1 mg of the active ingredient per unit dose, and in another embodiment, the pharmaceutical composition includes 0.1 µg to 0.09 mg of the active ingredient per unit dose.

A proposed dose of the compound (R)-5-(methylaminosulfonylmethyl)-3-(pyrrolidin-2-ylmethyl)-1H-indole for oral, parenteral or buccal administration to the average adult human for the treatment of the conditions referred to above (e.g., migraine) is 0.01 µg to 200 mg of the active ingredient per unit dose which could be administered, for example, 1 to 4 times per day. In one embodiment, the pharmaceutical composition includes 0.01 µg to less than 0.1 mg of the active ingredient per unit dose, and in another embodiment, the pharmaceutical composition includes 0.01 µg to 0.09 mg of the active ingredient per unit dose.

A proposed dose for the other active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 0.01 µg to 1000 µg of the compounds (R)-5-(methylaminosulfonylmethyl)-3-(N-methyl-pyrrolidin-2-ylmethyl)-1H-indole, (R)-5-(aminosulfonylmethyl)-3-(N-methylpyrrolidin-2-ylmethyl)-1H-indole or (R)-5-(methylaminosulfonylmethyl)-3-(pyrrolidin-2-ylmethyl)-1H-indole. In one embodiment, each metered dose or "puff" of aerosol contains 0.01 µg to less than 20 µg of the active ingredient, and in another embodiment, each metered dose or "puff" of aerosol contains 0.01 µg to 19 µg of the active ingredient. The overall daily dose with an aerosol will be within the range 0.05 µg to 10 mg. In one embodiment, the overall daily dose with an aerosol will be within the range 0.05 µg to less than 100 µg of the active ingredient, and in another embodiment, the overall daily dose with an aerosol will be within the range 0.05 µg to 99 µg of the active ingredient. Administration may be several times daily, for example 2, 3, 4 or 8 times, giving for example, 1, 2 or 3 doses each time.

Aerosol formulations for treatment of the conditions referred to above (e.g., migraine) in the average adult human are preferably arranged so that each metered dose or "puff" of aerosol contains 20 µg to 1000 µg of the other compounds of the invention. The overall daily dose with an aerosol will be within the range 100 µg to 10 mg. Administration may be several times daily, for example 2, 3, 4 or 8 times, giving for example, 1, 2 or 3 doses each time.

The above-cited ranges will generally be those most desirably employed in the administration of the active compounds. Nevertheless, variations may still occur depending on the age, weight, the patient's individual response to the compound being administered, as well as the severity of the condition for which he, or she, is being treated and the type of pharmaceutical formulation chosen and time period and interval at which such administration is carried out. In some instances, dosage levels below the lower limit of the aforesaid ranges may be more than adequate, while in other cases still larger doses may be employed without causing harmful side effects provided that such higher dose levels are first divided into small doses for administration throughout the day.

The following Examples illustrate the preparation of the compounds of the present invention. Melting points are uncorrected. NMR data are reported in parts per million ($\delta$) and are referenced to the deuterium lock signal from the sample solvent. Specific rotations were measured at room temperature using the sodium D line (589 nm).

Commercial reagents were utilized without further purification. Chromatography refers to column chromatography performed using 32–63 µm silica gel and executed under nitrogen pressure or compressed air pressure (flash chromatography) or gravity conditions. Room temperature refers to 20°–25° C.

EXAMPLE 1

General Procedure for the Reduction of Benzyloxycarbonyl-pyrrolidin-2-ylcarbonyl-1H-indole, N-Benzyloxycarbonyl-azetidin-2-ylcarbonyl-1H-indoles, or N-Benzyloxycarbonyl-piperidin-2-ylcarbonyl-1H-indoles Forming 3-(N-Methyl-pyrrolidin-2-ylmethyl)-1H-indoles, 3-(N-Methylazetidin-2-ylmethyl)-1H-indoles, or 3-(N-Methylpiperidin-2-ylmethyl)-1H-indoles, respectively.

To a stirred solution of (R)- or (S)-(N-benzyloxycarbonylpyrrolidin-2-ylcarbonyl)-1H-indole, (R)-, (S), or (R,S)-

(N-benzyloxycarbonylazetidin-2-ylcarbonyl)-1H-indole, or (R)-, (S)-, or (R,S)-(N-benzyloxycarbonylpiperidin-2-ylcarbonyl)-1H-indole, (5.00 mmol) in anhydrous tetrahydrofuran (20 mL) at room temperature under nitrogen was carefully added lithium aluminum hydride (0.57 g, 15.0 mmol, 3.0 eq) as a powder, and the resulting mixture was stirred at room temperature under nitrogen for 1 hour. The mixture was then heated at reflux (66° C.) under nitrogen for 12 hours. The reaction was then quenched with successive additions of water (0.5 mL), aqueous sodium hydroxide (20%, 0.5 mL), and then additional water (1.0 mL), and the resulting mixture filtered through diatomaceous earth (Celite (trademark)). The solids were then washed with copious amounts of ethyl acetate (50 mL). The combined filtrate was then washed with water (20 mL), dried ($MgSO_4$), and evaporated under reduced pressure. The residue was then column chromatographed using silica gel (50 g) and elution with the appropriate solvent system to afford the 3-(N-methylpyrrolidin-2-ylmethyl)-1H-indole, 3-(N-methylazetidin-2-ylmethyl)-1H-indole, or 3-(N-methylpiperidin-2-ylmethyl)-1H-indole. Following this procedure the following compounds were prepared:

A. (S)-5-Methoxy-3-(N-methylpyrrolidin-2-ylmethyl)-1H-indole (S)-(N-Benzyloxycarbonylpyrrolidin-2-ylcarbonyl)-5-methoxy-1H-indole was used. The chromatographic eluent was 8% triethylamine in ethyl acetate to afford the title compound (yields ranged from 22 to 57%) as an oil: IR ($CHCl_3$) 3475, 1625, 1585, 1480, 1455 $cm^{-1}$; $^1H$ NMR ($CDCl_3$) δ8.13 (br s, 1H), 7.23 (d, J=8.8 Hz, 1H), 7.04 (d, J=2.4 Hz, 1H), 6.97 (d, J=2.2 Hz, 1H), 6.84 (dd, J=2.4 and 8.8 Hz, 1H), 3.86 (s, 3H), 3.17–3.10 (m, 2H), 2.58 (dd, J=9.9 and 13.9 Hz, 1H), 2.50–2.40 (m, 1H), 2.47 (s, 3H), 2.26–2.17 (m, 1H), 1.89–1.72 (m, 2H), 1.70–1.52 (m, 2H); $^{13}C$ NMR ($CDCl_3$) δ153.8, 131.4, 128.2, 122.7, 113.9, 111.8, 111.7, 101.1, 66.6, 57.5, 56.0, 40.8, 31.5, 30.0, 21.9; LRMS, m/z (relative intensity) 244 ($M^+$, 7), 160 (20), 145 (16), 117 (21), 84 (100); HRMS: calculated for $C_{15}H_{20}N_2O$: 244.1573; found: 244.1575; $[α]^{25}_D$=−96° ($CHCl_3$, c=1.0).

B. (R)-5-Methoxy-3-(N-methylpyrrolidin-2-ylmethyl)-1H-indole (R)-(N-Benzyloxycarbonylpyrrolidin-2-ylcarbonyl)-5-methoxy-1H-indole was used. The chromatographic eluent was 8% triethylamine in ethyl acetate to afford the title compound (yields ranged from 13 to 61%) as an oil whose spectral and physical properties were identical with the spectral and physical properties of the title compound of Example 1A with the exception of specific rotation of plane polarized light: $[α]^{25}_D$=+100° ($CHCl_3$, c=1.0). HRMS: calculated for $C_{15}H_{20}N_2O$: 244.1573; found: 244.1547.

C. (R)-5-Dibenzylamino-3-(N-methylpyrrolidin-2-ylmethyl)-1H-indole (R)-3-(N-Benzyloxycarbonylpyrrolidin-2-ylcarbonyl)-5-dibenzylamino-1H-indole was used. Column chromatography using elution with methylene chloride/methanol/ammonium hydroxide [9:1:0.1] afforded the title compound as a pale green foam: $^1H$ NMR ($CDCl_3$) δ7.82 (br s, NH), 7.35–7.19 (m, 10 H), 7.20 (d, J=8.6 Hz, 1H), 6.95 (d, J=2.1 Hz, 1H), 6.85 (dd, J=2.3 and 8.7 Hz, 1H), 6.80 (d, J=2.2 Hz, 1H), 4.65 (s, 4H), 3.25–3.02 (m, 2H), 2.52 (dd, J=9.5 and 13.9 Hz, 1H), 2.39–2.15 (m, 2H), 2.30 (s, 3H), 1.85–1.40 (m, 4H); $^{13}C$ NMR ($CDCl_3$) δ143.2, 139.7, 130.5, 128.5, 128.2, 127.3, 126.8, 122.9, 112.5, 112.2, 111.8, 103.4, 67.0, 57.4, 56.4, 40.6, 31.4, 29.7, 21.9. HRMS: calculated for $C_{28}H_{31}N_3$ 409.2520. Found 409.2475.

D. (R)-5-Methoxy-3-(N-methylpiperid-2-ylmethyl)-1H-indole (R)-3-(N-Benzyloxycarbonylpiperid-2-ylcarbonyl)-5-methoxy-1H-indole was used. Column chromatography using elution with 6% triethylamine in ethyl acetate afforded the title compound as a white foam: $^{13}C$ NMR ($CDCl_3$) δ153.7, 31.4, 128.3, 123.3, 113.2, 111.7, 111.6, 101.2, 64.4, 57.2, 55.9, 43.4, 31.0, 28.8, 25.9, 24.1; $[α]^{25}_D$=+67° ($CDCl_3$, c=1.0); HRMS: calculated for $C_{16}H_{22}N_2O$: 258.1734. Found: 258.1710.

E. (S.)-5-Methoxy-3-(N-methylazetidin-2-ylmethyl)-1H-indole (S)-3-(N-Benzyloxycarbonylazetidinyl-2-ylcarbonyl)-5-methoxy-1H-indole was used. The chromatographic eluent was 8% triethylamine in ethyl acetate to afford the title compound as a white solid: top, 118.0°–120.0° C.; $^{13}C$ NMR ($CDCl_3$) δ153.8, 131.6, 128.0, 122.9, 112.3, 111.9, 111.8, 101.0, 68.5, 56.0, 53.1, 44.7, 32.4, 25.0; $[α]^{25}_D$=−44° ($CHCl_3$, c=1.0). Anal. calcd for $C_{14}H_{18}N_2O$: C, 73.01; H, 7.88, N, 12.16. Found: C, 72.65; H, 7.91; N, 12.06.

F. (R,S)-5-Methoxy-3-(N-methylazetidin-2-ylmethyl)-1H-indole (R,S)-3-(N-Benzyloxycarbonylazetidinyl-2-ylcarbonyl)-5-methoxy-1H-indole was used. The chromatographic eluet was 10% triethylamine in ethyl acetate to afford the title compound as a white solid: mp, 116.0°–119.0° C.; Anal. calcd for $C_{14}H_{18}N_2O$: C, 73.01; H, 7.88; N, 12.16. Found: C, 72.61; H, 7.99; N, 12.10.

EXAMPLE 2

General Method for the Hydrogenation of 5-(2-Sulfonylethenyl)-3-(N-methylpyrrolidin-2-ylmethyl)-1H-indoles to Form 5-(2-Sulfonylethyl)-3-(N-methylpyrrolidin-2-ylmethyl)-1H-indoles A solution of 5-(2-sulfonylethenyl)-3-(N-methylpyrrolidin-2-yl)-1H-indole (0.47 mmol) and 10% Pd/C (0.150 g) in ethanolic hydrogen chloride [prepared from absolute ethanol (10 mL) and acetyl chloride (43 μL)] and N, N-dimethylformamide (7.5 mL) was shaken under a hydrogen atmosphere (15 psi) at room temperature for 20 hours. The resultant reaction mixture was filtered through diatomaceous earth (Celite (trademark)), washed with absolute ethanol, and the combined filtrates were evaporated under reduced pressure. The residue was partitioned between ethyl acetate and water. The organic phase was separated, washed with water (3×), brine (1×), dried ($Na_2SO_4$), and evaporated under reduced pressure to afford a yellow oil. Column chromatography of this oil using silica gel and elution with methylene chloride/absolute ethanol/ammonia (90:10:1) afforded the appropriate 5-(2-Ethylsulfonylethyl)-3-(N-methylpyrrolidin-2-ylmethyl)-1H-indole. Following this procedure, the following compounds were prepared:

A. (R)-5-(2-Ethylsulfonylethyl)-3-(N-methylpyrrolidin-2-ylmethyl)-1H-indole (R)-5-trans-(2-Ethylsulfonylethenyl)-3-(N-methylpyrrolidin-2-ylmethyl)-1H-indole (Example 4A) was reduced as described above. Chromatography afforded the title compound (0.33 mmol, 70%) as a gum: TLC ($CH_2Cl_2$.EtOH:$NH_{3, 90:10:1}$): $R_f$=0.3; $[α]^{25}_D$=+62° (methanol, c=0.10). Anal. Calcd for $C_{18}H_{26}N_2O_2S$ · 0.05 $CH_2Cl_2$: C, 63.21; H, 7.67; N, 8.17; found: c, 63.55; H, 7.61; N, 8.41.

B. (R)-5-(2-Methylaminosulfonylethyl)-3-(N-methylpyrrolidin-2-ylmethyl)-1H- indole (R)-5-trans-(2-Methylaminosulfonylethenyl)-3-(N-methylpyrrolidin-2-ylmethyl)-1H-indole (Example 4B) was reduced as described above. Chromatography afforded the title compound (65%) as a foam. Anal. Calcd for $C_{17}H_{25}N_3O_2S$ · 0.1 $CH_2Cl_2$: C, 59.71; H, 7.39; N, 12.12; found: C, 59.66; H, 7.14; N, 11.90.

EXAMPLE 3

General Synthesis of 3-(N-Benzyloxycarbonylpyrrolidin-2-ylcarbonyl)-1H-indoles 3-(N-Benzyloxycarbonylazetidin-2-ylcarbonyl)-1H-indoles, or 3-(N-Benzyloxycarbonylpiperidin-2-ylcarbonyl)-1H-indoles.

Two solutions containing the reactants were prepared separately as follows. To a stirred solution of N-carbobenzyloxyproline (D or L, 3.10 g, 12.4 mmol, 1 eq) or N-carbobenzyloxyazetidine-2-carboxylic acid (R or S or racemate, 12.4 mmol) or N-carbobenzyloxypipecolinic acid (R or S or racemate, 12.4 mmol) in anhydrous methylene chloride (7 mL) with one drop dimethylformamide was added oxalyl chloride (1.60 mL, 18.4 mmol, 1.5 eq), and the resulting effervescing solution was stirred at room temperature under nitrogen for 1.5 hours. The solution was then evaporated under reduced pressure, and any remaining solvent was removed from the residual oil using high vacuum to afford the N-benzyloxycarbonylproline acid chloride. At the same time, a solution of ethylmagnesium bromide (3.0M in ether, 4.13 mL, 12.4 mmol, 1 eq) was added to a stirred solution of the indole (12.4 mmol) in anhydrous ether (50 mL), and this cloudy solution was heated at reflux under nitrogen for 1.5 hours to form the indolemagnesium bromide salt. The proline acid chloride was then dissolved in methylene chloride or ethyl ether (3 mL), and this solution was added dropwise to the stirred solution of the indolemagnesium bromide salt at room temperature, and the resultant reaction mixture was stirred at room temperature under nitrogen for 1 hour. A saturated solution of sodium hydrogen carbonate (25 mL) and ethyl acetate (50 mL) was then added to the reaction mixture, and this mixture was vigorously stirred for 15 minutes. The resulting mixture was filtered through diatomaceous earth (Celite (trademark)), the solids washed with copious amounts of ethyl acetate, and the ethyl acetate layer was separated from the aqueous layer which was extracted with ethyl acetate (2×25 mL). All ethyl acetate extracts were combined, dried, and evaporated under reduced pressure. The residual oil/solid was flash chromatographed using silica gel (250 g) and eluted with an appropriate solvent system to afford the desired 3-(N-benzyloxycarbonylpyrrolidin-2-ylcarbonyl)indole,3-(N-benzyloxycarbonylazetidin-2-ylcarbonyl)-1H-indole, or 3-(N-benzyloxycarbonylpiperidin-2-ylcarbonyl)-1H-indole.

A. (S)-3-(N-Benzyloxycarbonylpyrrolidin-2-ylcarbonyl)-5-methoxy-1H-indole

N-Carbobenzyloxy-L-proline was used. Chromatography using 40–60% ethyl acetate gradient in hexanes afforded the title compound (yields ranged from 27 to 43%) as a white powder. Recrystallization in ethyl acetate/hexanes afforded an analytical sample as a white crystalline solid: mp, 164.0°–165.0° C.; IR (KBr) 3250, 1695, 1660, 1585, 1520, 1485, 1450, 1425 cm$^{-1}$; $^1$H NMR (CDCl$_3$) [Note: the spectrum of the title compound appears as a 1:3 mixture of diastereomers due to slow inversion of the amide nitrogen on an NMR time scale. Therefore, the $^1$H NMR will be interpreted for each compound separately with the more abundant conformer quoted first] δ [more abundant conformer] 9.83 (br s, 1H), 7.53 (d, J=3.4 Hz, 1H), 7.42–7.30 (m, 6H), 7.00 (d, J=8.9 Hz, 1H), 6.69 (dd, J=2.4 and 9.0 Hz, 1H), 5.25 (d, J=12.9 Hz, 1H), 5.14 (d, J=12.5 Hz, 1H), 5.07–4.99 (m, 1H), 3.74 (s, 3H), 3.78–3.55 (m, 2H), 2.28–1.84 (m, 4H) and δ [less abundant conformer] 9.28 (br s, 1H), 7.90 (d, J=2.3 Hz, 1H), 7.59 (d, J=3.4 Hz, 1H), 7.24 (d, J=9.0 Hz, 1H), 7.06–6.90 (m, 5H), 6.88 (dd, J=2.7 and 9.0 Hz, 1H), 5.07–4.99 (m, 2H), 4.96–4.88 (m, 1H), 3.86 (s, 3H), 3.78–3.55 (m, 2H), 2.28–1.84 (m, 4H); LRMS, m/z (relative intensity) 379 (8), 378 (M$^+$, 33), 204 (31), 174 (64), 160 (41), 146 (10), 91 (100). Analysis: calculated for C$_{22}$H$_{22}$N$_2$O$_4$: C, 69.83; H, 5.86; N, 7.40; found: C, 69.81; H, 5.67; N, 7.40.

B. (R)-3-(N-Benzyloxycarbonylpyrrolidin-2-ylcarbonyl)-5-methoxy-1H-indole

N-Carbobenzyloxy-D-proline was used. Chromatography using 40–60% ethyl acetate gradient in hexanes afforded the title compound (yields ranged from 25 to 36%) as a white powder. Recrystallization in ethyl acetate/hexanes afforded an analytical sample as a white crystalline solid: mp, 165.0°–166.0° C. The spectral and physical data for the title compound were identical in all respects with the spectral and physical data of its enantiomer (the title compound of Example 3A); HRMS: calculated for C$_{22}$H$_{22}$N$_2$O$_4$: 378.1582; found: 378.1573.

C. (R)-3-(N-Benzyloxycarbonylpyrrolidin-2-ylcarbonyl)-5-dibenzylamino-1H-indole

N-Carbobenzyloxy-D-proline was used. Trituration of the extraction residue with diethyl ether afforded the title compound as a solid: mp, 176.0°–177.0° C.; LRMS (m/z, relative intensity) 543 (100, M$^+$), 453 (10), 407 (7), 339 (40), 307 (10), 247 (10), 154 (38); [α]$^{25}_D$=+112° (THF, c=1.0); Anal. calcd for C$_{35}$H$_{33}$N$_3$O$_3$: C, 77.32; H, 6.12; N, 7.73. Found: C, 77.35; H, 6.30; N, 7.66.

D. (R)-3-(N-Benzyloxycarbonylpiperid-2-ylcarbonyl)-5-methoxy-1H-indole

N-Carbobenzyloxy-D-pipecolinic acid was used. Column chromatography using elution with 10% ether in methylene chloride afforded the title compound as a tan foam: LRMS (m/z, relative intensity) 392 (90, M$^+$), 348 (27), 284 (13), 273 (12), 258 (15), 237 (47), 217 (58), 173 (100). Anal. calculated for C$_{35}$H$_{33}$N$_3$O$_2$: C, 69.22; H, 5.53; N, 7.69. Found: C, 69.35; H, 5.33; N, 7.64.

E. (S)-3-(N-Benzyloxycarbonylazetidinyl-2-ylcarbonyl)-5-methoxy-1H-indole (S)-N-Carbobenzyloxyazetidine-2-carboxylic acid was used. Trituration of the extract residue with absolute methanol afforded the title compound as a white solid: mp, 199.0°–200.0° C. Anal. calcd for C$_{21}$H$_{20}$N$_2$O$_4$: C, 69.22; H, 5.53; N, 7.69. Found: C, 69.35; H, 5.33; N, 7.64.

(R,S)-3-(N-Benzyloxycarbonylazetidinyl-2-ylcarbonyl)-5-methoxy-1H-indole (R,S)-N-Carbobenzyloxyazetidine-2-carboxylic acid was used. Trituration of the extract residue with absolute methanol afforded the title compound as a white solid: mp, 199.0°–200.0° C. Anal. calcd for C$_{21}$$_{H20}$N$_2$O$_4$: C, 69.22; H, 5.53; N, 7.69. Found: C, 68.85; H, 5.47; N, 7.57.

EXAMPLE 4

General Method for the Synthesis of 5-trans-(2Sulfonylethenyl)-3-(N-methylpyrrolidin-2-ylmethyl)-1H-indoles A mixture of the appropriate vinyl sulfone (1.17 mmol, 1.4 eq), tri-o-tolylphosphine (0.075 g, 0.25 mmol, 0.33 eq), palladium (II) acetate (0.013 g), triethylamine (0.25 mL, 1.79 mmol, 2 eq), and (R)-5-bromo-3-(N-methylpyrrolidinylmethyl)-1H-indole (0.25 g, 0.85 mmol) in anhydrous acetonitrile (3 mL) was heated at reflux under nitrogen for 17 hours. The resultant reaction mixture was evaporated under reduced pressure, and the residue was column chromatographed using silica gel and elution with methylene chloride/absolute ethanol/ammonia (90:8:1) to afford the title compound.

A. (R)-5-trans-(2-Ethylsulfonylethenyl)-3-(N-methylpyrrolidin-2-ylmethyl)-1H-indole Ethyl vinyl sulfone was used, and chromatography afforded the title compound (65%) as a white foam: TLC ($CH_2Cl_2$/EtOH/$NH_3$, 90:10:1):$R_f$=0.5. Analysis: calculated for $C_{18}H_{24}N_2O_2S \cdot 0.2\ CH_2Cl_2$: C, 62.55; H, 7.04; N, 8.02; found: C, 62.65; H, 6.94; N, 7.92.

B. (R)-5-trans-(2-Methylaminosulphonylethenyl)-3-(N-methyl-pyrrolidin-2-ylmethyl)-1H-indole N-methylvinylsulfonamide was used, and chromatography afforded the title compound (71%) as a white foam. Analysis: calculated for $C_{17}H_{23}N_3O_2S \cdot 0.1\ CH_2Cl_2$: C, 60.06; H, 6.84; N, 12.29; found: C, 59.74; H, 6.77; N, 11.97.

EXAMPLE 5

General Procedure for the Hydride Reduction of 3-(N-Benzyloxycarbonyl-pyrrolidin-2-ylmethyl)-1H-indoles and 3-(N-Benzyloxycarbonylpiperid-2-ylmethyl)-1H-indoles Forming 3-(N-Methylpyrrolidin-2-ylmethyl)-1H-indoles and 3-(N-Methylpiperid-2-ylmethyl)-1H-indoles To a stirred mixture of lithium aluminum hydride (0.152 g, 4.00 mmol, 2 eq) in anhydrous tetrahydrofuran (10 mL) at 0° C. was added rapidly a solution of the 3-(N-benzyloxycarbonylpyrrolidin-2-ylmethyl)-1H-indole or the 3-(N-benzyloxycarbonylpiperid-2-ylmethyl)-1H-indole (2.00 mmol) in anhydrous tetrahydrofuran (5 mL). The resulting mixture is heated at reflux under a nitrogen atmosphere for 3 hours. The reaction mixture is cooled, and water (0.25 mL), 15% aqueous sodium hydroxide (0.25 mL), and then more water (0.75 mL) were added sequentially. The resulting mixture was stirred at 25° C. for 30 minutes, filtered, and the filtrate was evaporated under reduced pressure. The residue was column chromatographed using silica gel (approximately 50 g) and elution with a solution methylene chloride: methanol: ammonium hydroxide [9:1:0.1] or other appropriate solvent system to afford the corresponding 3-(N-methylpyrrolidin-2-ylmethyl)-1H-indole or 3-(N-methylpiperid-2-ylmethyl)-1H-indole.

Following this procedure the following compounds were prepared:

A. (R)-5-(Methylaminosulfonylmethyl)-3-(N-methylpyrrolidin-2-ylmethyl)-1H-indole (R)-3-(N-Benzyloxycarbonylpyrrolidin-2-ylmethyl)-5-(methylaminosulfonylmethyl)-1H-indole was used. The reaction residue after aqueous work-up as described above was triturated with absolute methanol to afford the title compound as a white solid: mp, 213.0°–214.0° C.; $^1$H NMR (DMSO-$d_6$) δ10.9 (br s, indole NH), 7.51 (be d, 1H), 7.31 (d, J=8.3 Hz, 1H), 7.16 (br d, 1H), 7.08 (br dd, J=8.3 Hz, 1H), 6.82 (br q, sulfonamide NH), 4.35 (s, 2H), 3.07–2.95 (m, 2H), 2.54 (d, J=4.7 Hz, 3H), 2.52–2.38 (m, 2H), 2.35 (s, 3H), 2.10 (br, q, J=8.2 Hz, 1H), 1 75–1.40 (m, 4H); $[\alpha]^{25}_D$=+89° (DMSO-$d_6$, c=1.0); Anal. calcd for $C_{16}H_{23}N_3SO_2$: C, 59.79; H, 7.21; N, 13.07. Found: C, 59.66; H, 7.29; N, 12.81. M.E.D. for inhibition of plasma protein extravasation i.v. in guinea pigs, 1.0 pmol per kg.

B. (R)-5-Aminomethyl-3-(N-methylpyrrolidin-2-ylmethyl)-1H-inole (R)-3-(N-Benzyloxycarbonylpyrrolidin-2-ylmethyl)-5-cyano-1H-indole was used. Column chromatography using elution with 9:1:0.1 [methylene chloride:methanol:ammonium hydroxide] afforded the title compound as a white foam: $^{13}$C NMR δ135.6, 132.3, 127.5, 123.0, 122.8, 121.4, 117.1, 112.8, 111.5, 66.8, 57.2, 46.4, 40.5, 31.2, 29.2, 21.5; HRMS: calculated for $C_{15}H_{21}N_3$ 243.1737, found 243.1732.

C. (R,S)-5-(Methylaminosulfonylmethyl)-3-(N-methylpiperid-2-ylmethyl)-1H-indole (R,S)-3-(N-Benzyloxycarbonylpiperidin-2-ylmethyl)-5-(methylaminosulfonylmethyl)-1H-indole was used. Column chromatography using elution with 10% triethylamine in ethyl acetate afforded the title compound as a clear, colorless oil: $^{13}$C NMR (DMSO-$d_6$) δ135.9, 127.7, 124.0, 123.6, 121.0, 119.7, 111.9, 111.1, 63.9, 56.7, 56.3, 43.2, 30.5, 29.0, 27.9, 25 5, 23.7; LRMS (m/z, relative intensity) 336 (1, M$^+$), 241 (5), 143 (31), 142 (13), 99 (34), 98 (100), 70 (16); HRMS calculated for $C_{17}H_{25}N_3O_2S$: 336.1745; found: 336.1756.

EXAMPLE 6

General Procedure for the Catalytic Reduction of 3-(N-Benzyloxycarbonylpyrrolidin-2-ylmethyl)-1H-indoles and 3-(N-Benzyloxycarbonylpiperid-2-ylmethyl)-1H-indoles Forming 3-(Pyrrolidin-2-ylmethyl)-1H-indoles and 3-(Piperid-2-ylmethyl)-1H-indoles A mixture of the 3-(N-benzyloxycarbonylpyrrolidin-2-ylmethyl)-1H-indole or the 3-(N-benzyloxycarbonylpiperid-2-ylmethyl)-1H-indole (2.00 mmol), 10% palladium on carbon (0.20 g), and ammonium formate (1.26 g, 20 mmol, 10 eq) in absolute ethanol (15 mL) was stirred under a nitrogen atmosphere for 4 hours. The resulting reaction mixture was filtered through diatomaceous earth, and the filtrate was evaporated under reduced pressure. The residue was column chromatographed using silica gel (approximately 50 g) and elution with a solution of methylene chloride: methanol: ammonium hydroxide [8:2:0.2] or other appropriate solvent system to afford the corresponding 3-(pyrrolidin-2-ylmethyl)-1H-indole or 3-(piperid-2-ylmethyl)-1H-indole.

Following this procedure the following compounds were prepared:

A. (R)-5-(Methylaminosulfonylmethyl)-3-(pyrrolidin-2-ylmethyl)-1H-indole (R)-3-(N-Benzyloxycarbonylpyrrolidin-2-ylmethyl)-5(methylaminosulfonylmethyl)-1H-indole was used. Column chromatography as described above afforded the title compound as an off-white gum: $^{13}$C NMR (DMSO-$d_6$) δ135.9, 127.5, 123.8, 123.7, 120.9, 119.7, 112.4, 111.1, 59.2, 56.6, 45.7, 31.1, 31.0, 29.0, 24.6; $[\alpha]^{25}_D$=+4° (DMSO-$d_6$, c=1.0); $[\alpha]^{25}_D$=−14° (EtOH/CHCl$_3$[1:1], c=1.0); HRMS: calculated for $[C_{15}H_{21}N_3O_2S.H^+]$: 308.1433; found: 308.1467. M.E.D. for inhibition of plasma protein extravasation i.v. in guinea pigs, 0.1 pmol per kg.

B. (R)-5-Cyano-3-(pyrrolidin-2-ylmethyl)-1H-indole (R)-3-(N-Benzyloxycarbonylpyrrolidin-2-ylmethyl)-5-cyano-1H-indole was used. Column chromatography as described above afforded the title compound as an off-white gum: $^{13}$C NMR (CDCl$_3$/CD$_3$OD) δ138.1, 127.2, 125.0, 124.4, 124.2, 121.0, 113.4, 112.2, 101.5, 59.5, 50.1, 45.7, 31.3, 30.3, 24.7; LRMS (M/z, relative intensity) 225 (M+,3), 179 (3), 155 (10), 70 (100); HRMS: calculated for $C_{14}H_{15}N_3$ 225.1268, found 225.1245.

C. (R)-3-(pyrrolidin-2-ylmethyl)-1H-indole (R)-3-(N-Benzyloxycarbonylpyrrolidin-2-ylmethyl)-1H-indole was used. Evaporation of the filtrate residue directly afforded the title compound as a white foam: $^1$H NMR (CDCl$_3$) δ9.05 (br s, indole NH), 7.50 (d, J=8.6 Hz, 1H), 7.23 (d, J=8.6 Hz, 1H), 7.12–6.98 (m, 2H), 6.90 (s, 1H), 4.0 (br s, amine NH), 3.36–3.24 (m, 1H), 2.95–2.75 (m, 3H), 2.70–2.58 (m, 1H), 1.85–1.50 (m, 3H), 1.45–1.29 (m, 1H); $[\alpha]^{25}_D$=+18° (CHCl$_3$, c=1.0)

D. (R)-5-Methoxy-3-(Pyrrolidin-2-ylmethyl)-1H-indole (R)-3-(N-Benzyloxycarbonylpyrrolidin-2-ylmethyl)-5-methoxy-1H-indole was used. Evaporation of the filtrate residue directly afforded the title compound as a gum: LRMS (m/z, relative intensity) 231 (100, M+), 161 (10), 155 (17), 135 (11), 119 (32); $[\alpha]^{25}_D$=−12° (CHCl$_3$, c=1.0); Anal, calcd for $C_{14}H_{18}N_2O.0.75\ C_2H_4O_2$ [acetic acid salt]: C, 67.61; H, 7.69; N, 10.17. Found: C, 67.74; H, 7.53; N, 9.90.

E. (R,S)-5-(Methylaminosulfonylmethyl)-3-(piperid-2-ylmethyl)-1H-indole (R,S)-3-(N-Benzyloxycarbonylpiperid-2-ylmethyl)-5(methylaminosulfonylmethyl)-1H-indole was used. Column chromatography as described above afforded the title compound as a clear, colorless oil: $^{13}$C NMR (DMSO-d$_6$) δ136.0, 127.5, 124.2, 123.8, 121.0, 119.8, 111.2, 110.9, 56.8, 56.7, 45.8, 31.7, 31.4, 29.0, 25.0, 23.9; LRMS (m/z, relative intensity) 321 (19, M+), 238 (43), 227 (21), 144 (99), 143 (100); HRMS: calculated for $C_{16}H_{23}N_3O_2S$: 321.1513; found: 321.1501.

EXAMPLE 7

General Procedure for the Formulation of 3-(N-Benzyloxycarbonylpyrrolidin-2-ylmethyl)1H-indoles and3-(N-Benzyloxycarbonylpiperid-2-ylmethyl)-1H-indoles Via the Palladium Catalyzed Cyclization of 1-(N-Benzyloxycarbonylpyrrolidin-2-yl)-3-(N-(2-halophenyl)-N-trifluoroacetylamino)propenes and 1-(N-Benzyloxycarbonylpiperid-2-yl)-3-(N-(2-halophenyl)-N-trifluoroacetylamino)propenes A mixture of the 1-(N-benzyloxycarbonylpyrrolidin-2-yl)-3-(N-(2-halophenyl)-N-trifluoroacetylamino) propene or the 1-(N-benzyloxycarbonylpiperid-2-yl)-3-(N-(2halophenyl)-N-trifluoroacetylamino) propene (2.00 mmol), tetrabutylammonium chloride (2.00 mmol), and palladium(II) acetate (0.089 g, 0.40 mmol, 0.2 eq) in a solution of triethylamine (8 mL) and anhydrous N,N-dimethylformamide (4 mL) was heated at reflux under nitrogen for 2 hours. The resulting reaction mixture was evaporated under reduced pressure, and the residue was partitioned between ethyl acetate (25 mL) and water (25 mL). The ethyl acetate layer was removed, and the aqueous layer was extracted with additional ethyl acetate (25 mL). The organic extracts were combined, dried (MgSO$_4$), and evaporated under reduced pressure. The residue was column chromatographed using silica gel (approximately 50 g) and elution with either a diethyl ether gradient in methylene chloride or an acetone gradient in methylene chloride to afford the corresponding 3-(N-benzyloxycarbonylpyrrolidin-2-ylmethyl)-1H-indole or the 3-(N-benzyloxycarbonylpiperid-2-ylmethyl)-1H-indole.

Following this procedure the following compounds were prepared:

A. (R)-3-(N-Benzyloxycarbonylpyrrolidin-2-ylmethyl)-1H-indole (R)-1-(N-Benzyloxycarbonylpyrrolidin-2-yl)-3-(N-(2-iodophenyl)-N-trifluoroacetyl-amino)propene was used. Column chromatography afforded the title compound as a clear, pale brown oil: $^1$H NMR (CDCl$_3$) δ8.05 (br s, indole NH), 7.49–7.34 (m, 7H), 7.17 (br t, 1H), 7.02 (br s, 1H), 6.95 (br s, 1H), 5.24 (s, 2H), 4.28–4.14 (br m, 1H), 3.52–3.41 (m, 2H), 3.28 (br d, 1H), 2.79–2.63 (m, 1H), 1.90–1.70 (m, 4H); LRMS (m/z, relative intensity) 334 (10, M+), 204 (16), 160 (39), 130 (39), 91 (100).

B. (R)-3-(N-Benzyloxycarbonylpyrrolidin-2-ylmethyl)-5-(methylaminosulfonylmethyl)-1H-indole (R)-1-(N-Benzyloxycarbonylpyrrolidin-2-yl)-3-(N-(2-bromo-4-methylaminosulfonylmethylphenyl)-N-trifluoroacetylamino)propene was used. Column chromatography afforded the title compound as an off-white foam: IR (CHCl$_3$) 1673, 1410, 1358, 1324, 1118, 1092 cm$^{-1}$; LRMS (m/z, relative intensity) 441 (9, M+), 237 (29), 204 (77), 160 (97), 143 (73), 91 (100); HRMS: calculated for $C_{13}H_{27}N_3O_4S$: 441.1724; found: 441.1704.

C. (R)-3-(N-Benzyloxycarbonylpyrrolidin-2-ylmethyl-5-cyano-1H-indole (R)-1-(N-Benzyloxycarbonylpyrrolidin-2-yl)-3-(N-(2-bromo-4-cyanophenyl)-N-trifluoroacetylamino)propene was used. Column chromatography afforded the title compound as a white foam: IR (1% solution in CHCl$_3$) 2215, 1687 cm$^{-1}$; $^{13}$C NMR [Note: due to slow nitrogen inversion two conformers of the products are seen by NMR spectroscopy] (CDCl$_3$) δ155.1, 137.9, 137.0, 128.8, 128.5, 128.4, 128.0, 127.8, 124.9, 124.6, 121.0, 114.0, 113.9, 112.1, 102.3, 67.2, 66.7, 58.5, 57.6, 47.0, 46.7, 30.3, 30.0, 29.6, 28.8, 23.6, 22.7. Anal. calcd for $C_{22}H_{21}N_3O_2$.0.25 $C_2H_4O_2$ [acetic acid]: C, 72.17; H, 5.92; N, 11.22. Found: C, 72.28; H, 5.76; N, 10.95.

D. (R,S)-3-(N-Benzyloxycarbonylpiperid-2-ylmethyl)-5-(methylaminosulfonylmethyl-1H-indole (R,S)-1-(N-Benzyloxycarbonylpiperid-2-yl)-3-(N-(2 bromo-4-methylaminosulfonyl-methylphenyl)-N-trifluoroacetylamino)propene was used. Column chromatography afforded the title compound as an off-white foam: $^{13}$C NMR [Note: due to slow nitrogen inverion two conformers of the products are seen by NMR spectroscopy] (CHCl$_3$) δ162.5, 136.9, 136.2, 128.4, 127.6, 124.5, 123.3, 120.8, 120.3, 111.5, 66.8, 57.4, 39.5, 36.5, 31.4, 29.8, 25.8, 25.5, 18.8; LRMS (m/z, relative intensity) 445 (5, M+), 361 (4), 238 (40), 218 (80), 174 (100), 143 (53); HRMS calculated for $C_{24}H_{29}N_3O_4S$: 455.1880; found: 455.1899.

EXAMPLE 8

(R)-3-(N-Benzyloxycarbonylpyrrolidin-2-ylmethyl)-5-methoxy-1H-indole

To a stirred mixture of lithium borohydride (0.092 g, 4.22 mmol, 2 eq) in anhydrous tetrahydrofuran (5 mL) at 0° C. was added a solution of the (R)-3-(N-benzyloxycarbonylpyrrolidin-2-ylcarbonyl)-5-methoxy-1H-indole (0.80 g, 2.11 mmol) in anhydrous tetrahydrofuran (8 mL). The resultant mixture was heated at reflux under nitrogen for 1 hour. The reaction mixture was cooled, and water (1 mL) was added carefully, followed by ethyl acetate (20 mL). The resultant mixture was stirred at room temperature for 30 minutes, dried (MgSO$_4$), filtered through diatomaceous earth, and the filtrate was evaporated under reduced pressure. The residue was column chromatographed using silica gel (approximately 50 g) and elution with ethyl acetate/hexanes [1:1] afforded (R)-3-(N-benzyloxycarbonylpyrrolidin-2-ylmethyl)-5-methoxy-1H-indole as a colorless gum: $^{13}$C NMR [Note: due to slow nitrogen inversion two conformers of the products are seen by NMR spectroscopy] (CDCl$_3$) δ162.5, 136.9, 136.2, 128.4, 127.8, 127.6, 124.5, 123.3, 120.8, 120.3, 111.5, 66.8, 57.4, 39.5, 36.5, 31.4, 29.8, 25.8, 25.5, 18.8; LRMS (m/z, relative intensity) 364 (30, M+), 204 (17), 160 (92), 145 (17), 117 (13), 91 (100). Anal. calcd for $C_{22}H_{24}N_2O_3$.0.5 $H_2O$ : C, 70.76; H, 6.75; N, 7.50. Found: C, 70.70; H, 6.94; N,7.15.

EXAMPLE 9

General Procedure for the Formation of 1-(N-Benzyloxycarbonylpyrrolidin-2-yl)-3-(N-(2-halophenyl)-N-trifluoroacetylamino)propenes and 1-(N-Benzyloxycarbonylpiperid-2-yl)-3-(N-(2-halophenyl)-N-trifluoroacetylamino)propenes from the Mitsunobu Coupling of 2-Halo-N-trifluoroacetylanilines with 1-(N-Benzyloxycarbonylpyrrolidin-2-yl)3-hydroxypro-pene or 1-(N-Benzyloxycarbonylpiperid-2-yl)-3hydroxypropene To a stirred mixture of 1-(N-benzyloxycarbonylpyrrolidin-2-yl)-3-hydroxypropene or 1-(N-benzyloxycarbonylpiperid-2-yl)-3-hydroxy-propene (R, or S, or racemate 2.00 mmol), the 2-halo-N-trifluoroacetylaniline (2.5 mmol, 1.25 eq), and triphenylphosphine (0.655 g, 2.50 mmol, 1.25 eq) in anhydrous tetrahydrofuran at 0° C. under a nitrogen atmosphere was added diethyl azodicarboxylate (0.39 mL, 2.48 mmol, 1.25 eq) dropwise. The reaction solution was slowly warmed to 25° C. over the course of 2 hours, and then stirred at 25° C. under a nitrogen atmosphere for an additional 12 hours. The resulting reaction solution was evaporated under reduced pressure, and the residue was column chromatographed using silica gel (approximately 50 g) and elution with either a diethyl ether gradient in hexanes or an ethyl acetate gradient in hexanes to afford the corresponding 1-(N-benzyloxycarbonylpyrrolidin-2-yl)-3-(N-(2-halophenyl)-N-trifluoroacetylamino)propene or 1-(N-benzyloxycarbonylpiperid-2-yl)-3-(N-(2-halophenyl)-N-trifluoroacetylamino)propene.

Following this procedure the following compounds were prepared:

A. (R)-1-(N-Benzyloxycarbonylpyrrolidin-2-yl)-3-(N-2-iodophenyl)-N-trifluoroacetylamino)propene (R)-1-(N-Benzyloxycarbonylpyrrolidin-2-yl)-3-hydroxypropene and 2-iodo-N-trifluoro-acetylaniline were used. Column chromatography afforded the title compound as a clear, colorless oil: $^1$H NMR (CDCl$_3$) δ7.88 (br d, 1H), 7.43–6.89 (m, 10H), 5.70–5.35 (m, 2H), 5.13 (br s, 2H), 5.00–4.75 (m, 1H), 4.40–4.29 (m, 1H), 3.60–3.42 (m, 3H), 2.05–1.45 (m, 4H); LRMS (FAB, m/z, relative intensity) 559 (100, [MH+]), 515 (52), 451 (15), 244 (7).

B. (R)-1-(N-Benzyloxycarbonylpyrrolidin-2-yl)-3-(N-(2-bromo-4-methylaminosulfonylmethylphenyl)-N-trifluoroacetylamino)propene (R)-1-(N-Benzyloxycarbonylpyrrolidin-2-yl)-3-hydroxypropene and 2-bromo-4-methylaminosulfonylmethyl-N-trifluoroacetylaniline were used. Column chromatography using elution with 4% acetone in methylene chloride afforded the title compound as a white foam (44%): FAB LRMS (m/z, relative intensity) 620 ([MH+ with $^{81}$Br], 618 ([MH+ with $^{79}$Br], 98), 576 (50), 574 (63), 512 (17), 484 (33).

C. (R)-1-(N-Benzyloxycarbonylpyrrolidin-2-yl)-3-(N-(2-bromo-4-cyanophenyl)-N-trifluoroacetylamino)propene (R)-1-(N-Benzyloxycarbonylpyrrolidin-2-yl)-3-hydroxypropene and 2-bromo-4-cyano-N-trifluoroacetylaniline were used. Column chromatography using elution with a gradient of diethyl ether (5%–100%) in methylene chloride afforded the title compound as a clear, colorless oil: IR (CHCl$_3$) 2231, 1702, 1157 cm$^{-1}$; LRMS (m/z, relative intensity) 537 ([MH+ with $^{81}$Br], 13), 535 ([MH+ with $^{79}$Br], 13), 402 (29), 400 (30), 294 (55), 292 (57), 244 (80), 213 (89), 91 (100); Anal. calcd for C$_{24}$BrF$_3$H$_{21}$N$_3$O$_3$.0.2 H$_2$O: C, 53.39; H, 3.99; N, 7.78. Found: C, 53.25; H, 3.95; N, 7.98.

D. (R,S)-1-(N-Benzyloxycarbonylpiperid-2-yl)-3-(N-(2-bromo-4-methylaminosulfonylmethylphenyl)-N-trifluoroacetylamino)propene (R,S)-1-(N-Benzyloxycarbonylpiperid-2-yl)-3-hydroxypropene and 2-bromo-4-methylaminosulfonylmethyl-N-trifluoroacetylaniline were used. Column chromatography using elution with 20% acetonitrile in methylene chloride afforded the title compound as a white foam: FAB LRMS (m/z, relative intensity) 634 ([MH+ with $^{81}$Br], 26), 632 ([MH+ with $^{79}$Br], 22), 590 (35), 588 (43), 401 (33), 327 (48), 281 (75), 207 (90), 147 (100); FAB HRMS: calculated for C$_{26}$H$_{29}$BrF$_3$N$_3$O$_5$S.[H+] 632.1043, found 632.1047 [for $^{79}$Br and $^{32}$S].

EXAMPLE 10

General Synthesis of 2-Halo-N-trifluoroacetylanilines from Reaction of 2-Haloanilines and Trifluoroacetic Anhydride To a stirred solution of the 2-haloaniline (2.00 mmol) and pyridine (0.18 mL, 2.22 mmol, 1.1 eq) in anhydrous methylene chloride (10 mL) at 0° C. under a nitrogen atmosphere was added dropwise trifluoroacetic anhydride (0.31 mL, 2.19 mmol, 1.1 eq). The resultant reaction mixture was stirred at 0° C. under a nitrogen atmosphere for 3 hours. A saturated solution of sodium hydrogen carbonate was added (15 mL), and this aqueous mixture was extracted with ethyl acetate (3×15 mL). The extracts were combined, dried (MgSO$_4$), and evaporated under reduced pressure. The residue was column chromatographed using silica gel (approximately 50 g) and elution with an ethyl acetate gradient in hexanes to afford the corresponding 2-halo-N-trifluoroacetylaniline.

Following this procedure the following compounds were prepared:

A. 2-Iodo-N-trifluoroacetylaniline

2-Iodoaniline was used. Evaporation of the ethyl acetate extracts afforded the title compound directly as a white solid: mp, 105.0°–106.5° C.; FAB LRMS (m/z relative intensity) 316 ([MH+], 8), 155 (80), 135 (26), 119 (100); $^{13}$C NMR (acetone-d$_6$) δ206.2, 140.4, 130.2, 130.1, 128.2.

B. 2-Bromo-4-methylaminosulfonylmethyl-N-trifluoroacetylaniline

2-Bromo-4-methylaminosulfonylmethylaniline was used. Evaporation of the ethyl acetate extracts afforded the title compound directly as a white solid: mp, 164.0–166.0° C. Anal. calcd for C$_{10}$H$_{10}$BrF$_3$N$_2$O$_3$S: C, 32.02; H, 2.69; N, 7.47. Found: C, 32.18; H, 2.67; N, 7.30.

C. 2-Bromo-4-cyano-N-trifluoroacetylaniline

2-Bromo-4-aminocarbonylaniline was used. Dehydration of the carboxamide also occurred in this reaction. Column chromatography using ethyl acetate/hexanes afforded the title compound as a white solid: mp, 125°–130° C.; $^1$H NMR (DMSO-d$_6$) δ11.6 (br s, NH), 8.37 (d, J=1.8 Hz, 1H), 7.96 (dd, J=1.8 and 8.2 Hz, 1H), 7.71 (d, J=8.2 Hz, 1H).

EXAMPLE 11

General Procedure for the Bromination of Anilines to Form 2-Bromoanilines

To a stirred solution of the aniline (2.00 mmol) and sodium hydrogen carbonate (0.21 g, 2.50 mmol, 1.25 eq) in methanol (10 mL) at 0° C. was added dropwise bromine (0.113 mL, 2.19 mmol, 1.1 eq). The resulting reaction mixture was then stirred at 25° C. for 30 minutes. The reaction mixture was then evaporated under reduced pressure, and the residue was placed in a saturated solution of sodium hydrogen carbonate (10 mL). This aqueous mixture was extracted with ethyl acetate (3×15 mL). The extracts were combined, dried (MgSO$_4$), and evaporated under reduced pressure. The residue was column chromatographed using silica gel (approximately 50 g) and elution with an appropriate solvent system to afford the corresponding 2-bromoaniline.

Following this procedure the following compounds were prepared:

A. 2-Bromo-4-methylaminosulfonylmethylaniline

4-Methylaminosulfonylmethylaniline (M. D. Dowle, et al. Eur. Pat. Appl. EP225,726) was used. Column chromatography using elution with 40% ethyl acetate in hexanes afforded the title compound as a white solid: mp, 104.0°–107.0° C. Anal. calcd for C$_8$H$_{11}$BrN$_2$O$_2$S: C, 34.42; H, 3.97; N, 10.04. Found: C, 34.66; H, 3.96; N, 9.96.

B. 4-Aminocarbonyl-2-bromoaniline

4-Aminobenzamide was used. Column Chromatography using elution with a ethyl acetate gradient (25–50%) in methylene chloride afforded the title compound as a white solid: mp, 144.5°–146.0° C.; $^1$H NMR (DMSO-d$_6$) δ7.93 (d, J=2.0 Hz, 1H), 7.70 (br s, amide NH), 7.62 (dd, J=2.0 and 8.5 Hz, 1H), 7.05 (br s, amide NH), 6.77 (d, J=8.5 Hz, 1H), 5.85 (s, aniline NH$_2$).

EXAMPLE 12

1-(N-Benzyloxycarbonylpyrrolidin-2-yl)-3-hydroxypropene or 1-(N-Benzyloxycarbonylpiperid-2-yl)-3hydroxypropene To a stirred solution of either ethyl 3-(N-benzyloxycarbonylpyrrolidin-2-yl)-2-propenoate or ethyl-3-(N-benzyloxycarbonylpiperid-2-yl)-2-propenoate (R, or S, or racemate, 10.00 mmol) in anhydrous tetrahydrofuran (75 mL) at −78° C. under nitrogen was added dropwise a solution of diisobutylaluminium hydride (1.0M in hexanes, 12.0 mL, 22.0 mmol, 2.2 eq). The resulting solution was stirred at −78° C. under nitrogen for 30 minutes. The reaction solution was then allowed to warmed to room temperature over the course of 2 hours. A saturated solution of sodium hydrogen carbonate (50 mL) was added, and the aqueous mixture was extracted with ethyl acetate (3×50 mL). The extracts were combined, dried (MgSO$_4$), and evaporated under reduced pressure. Column chromatography of the residue with diethyl ether/hexanes [1:1] afforded either 1-(N-benzyloxycarbonylpyrrolidin-2-yl)-3-hydroxypropene or 1-(N-benzyloxycarbonyl-piperid-2-yl)-3-hydroxypropene.

Following the procedure the following compounds were prepared:

A.  (R)-1-(N-Benzyloxycarbonylpyrrolidin-2-yl)-3hydroxypropene (R)-Ethyl 3-(N-benzyloxycarbonylpyrrolidin-2-yl)-2-propenoate was used. Chromatography of the extraction residue afforded the title compound as a clear, colorless oil: $^1$H NMR (CDCl$_3$) δ7.40–7.25 (m, 5H), 5.75–5.53 (m, 2H), 5.20–5.00 (m, 2H), 4.38 (br m, 1H), 4.06 (br d, J=13.7 Hz, 2H), 3.45 (br t, J=7.0 Hz, 1H), 2.03–1.68 (m, 4H); [α]$^{25}_D$= +34° (MeOH, c=1.0); HRMS: calculated for C$_{15}$H$_{19}$NO$_3$ 261.1365, found 261.1356.

B.  (R,S)-1-(N-Benzyloxycarbonylpiperid-2-yl)-3-hydroxypropene (R,S)-Ethyl 3-(N-benzyloxycarbonylpiperid-2-yl)-2-propenoate was used. Chromatography of the extraction residue afforded the title compound as a clear, colorless oil: LRMS (m/z, relative intensity) 257 (3), 212 (12), 193 (S), 175 (65), 173 (100), 145 (27), 109 (24), 91 (87); $^1$H NMR (CDCl$_3$) δ7.40–7.20 (m, 5H), 5.70–5.61 (m, 2H), 5.14 (d, J=17.6 Hz, 1H), 5.10 (d, J=17.5 Hz, 1H), 4.88 (br m, 1H), 4.14–4.00 (m, 3H), 2.91 (br t, J=12.7 Hz, 1H), 1.78–1.47 (m, 6H). Anal. calcd for C$_{16}$H$_{21}$NO$_3$.0.1 H$_2$O: C, 69.34; H, 7.71; N, 5.05. Found: 69.38; H, 7.84; N, 5.16.

EXAMPLE 13

Synthesis of Ethyl 3-(N-Benzyloxycarbonylpyrrolidin-2-yl)2-propenoate or Ethyl 3-(N-Benzyloxycarbonylpiperid-2-yl)-2-propenoate To a stirred solution of N-carbobenzyloxypyrrolidine-2-carboxaldehyde or N-carbobenzyloxypiperidine-2-carboxaldehyde (5.00 mmol) [S. Kiyooka, et al., *J. Org. Chem.*, 5409 (1989) and Y. Hamada, et al., *Chem. Pharm. Bull.*, 1921 (1982)] in anhydrous tetrahydrofuran at −78° C. was added (carbethoxymethylene) triphenylphosphorane (2.09 g, 6.00 mmol. 1.2 eq) as a solid portionwise. The resulting reaction mixture was stirred at room temperature under nitrogen for 2 hours, and then heated at reflux under nitrogen for 1 hour. The reaction mixture was evaporated under reduced pressure and the residue was column chromatographed using silica gel (approximately 100 g) and elution with 20% diethyl ether in hexanes afforded either ethyl 3-(N-benzyloxycarbonylpyrrolidin-2-yl)-2-propenoate or ethyl 3-(N-benzyloxycarbonylpiperid-2-yl)-2-propenoate.

A.  (R)-Ethyl 3-(N-Benzyloxycarbonylpyrrolidin-2-yl)-2-propenoate (R)-N-Carbobenzyloxypyrrolidine-2-carboxaldehyde was used. Chromatography as described above afforded the title compound as a clear, colorless oil: $^1$H NMR (CDCl$_3$-d$_6$) δ7.34–7.25 (m, 5H), 6.89–6.76 (m, 1H), 5.88–5.74 (m, 1H), 5.18–5.05 (m, 2H), 4.60–4.43 (m, 1H), 4.17 (q, J=7.1 Hz, 2H), 3.55–3.40 (m, 2H), 2.11–2.00 (m, 1H), 1.90–1.75 (m, 3H), 1.28 (t, J=7.1 Hz, 3H); $^{13}$C NMR (CDCl$_3$) [Note: due to slow nitrogen inversion two conformers of the products are seen by NMR spectroscopy] δ166.3, 154.7, 147.9, 147.4, 136.6, 128.4, 127.9, 120.9, 66.9, 65.8, 60.4, 58.1, 57.7, 46.8, 46.4, 31.6, 30.8, 23.6, 22.8, 22.6, 15.3, 14.2.

B.  (R,S)-Ethyl 3-(N-Benzyloxycarbonylpiperid-2-yl)-2propenoate (R,S)-N-Carbobenzyloxypiperidine-2-carboxaldehyde was used. Chromatography as described above afforded the title compound as a clear, colorless oil: $^1$H NMR (CDCl$_3$-d$_6$) a 7.36–7.27 (m, 5H), 6.85 (dd, J=4.4 and 16.3 Hz, 1H), 5.80 (dd, J-2.4 and 16.3 Hz, 1H), 5.11 (s, 2H), 5.01 (br m, 1H), 4.17 (q, J=6.7 Hz, 2H), 4.05 (br d, J=12.6 Hz, 1H), 2.87 (br t, 1H), 1.80–1.35 (m, 6H), 1.27 (t, J=6.6 Hz, 3H); FAB LRMS (m/z, relative intensity) 318 ([MH+], 100), 274 (86), 228 (14), 210 (21), 182 (43), 138 (32).

EXAMPLE 14

(R)-5-Amino-3-(N-methylpyrrolidin-2-ylmethyl) indole

A mixture of (R)-5-dibenzylamino-3-(N-methylpyrrolidin-2-ylmethyl) indole (1.08 g, 2.64 mmol) and palladium [II] hydroxide on carbon (0.6 g) in absolute ethanol (25 mL) was shaken under a hydrogen atmosphere (3 atm) at 40° C. for 4 hours. The resulting mixture was filtered through diatomaceous earth, and the filtrate was evaporated under pressure to afford the title compound (0.60 g, 2.62 mmol, 99%) as a white foam: $^1$H NMR (DMSO-d$_6$) δ10.65 (br s, NH), 7.14 (d, J=2.2 Hz, 1H), 7.12 (d, J=8.6 Hz, 1H), 6.85 (d, J=1.6 Hz, 1H), 6.60 (dd, J=2.0 and 8.6 Hz, 1H), 3.63–2.83 (m, 7H), 2.78 (s, 3H), 2.05–1.67 (m, 4H); [α]$^{25}_D$=+9° (MeOH, c=1.0); HRMS: calculated for C$_{14}$H$_{19}$N$_3$: 229.1575; found 229.1593.

EXAMPLE 15

General Synthesis of 5-carbonylamino-3-(N-methylpyrrolidin-2-ylmethyl)-1H-indoles and 5-sulfonylamino-3-(N-methylpyrrolidin-2-ylmethyl)-1H - indoles To a stirred solution of (R)-5-amino-3-(N-methylpyrrolidin-2-ylmethyl)indole (0.229 g, 1.00 mmol) and triethylamine (0.21 mL, 1.5 mmol, 1.5 eq) in anhydrous acetonitrile (3 mL) at 0° C. under nitrogen was added the appropriate carbonyl chloride or sulfonyl chloride (1.5 mmol, 1.5 eq). The resulting reaction mixture was stirred at room temperature for 12 hours. The reaction mixture was then evaporated under reduced pressure, and the residue was column chromatographed using silica gel (approximately 25 g) and elution with an appropriate solvent system afforded the appropriate 5-carbonylamino-3-(N-methylpyrrolidin-2-ylmethyl)-1H-indole or 5-sulfonylamino-3-(N-methylpyrrolidin-2-ylmethyl)-1H-indole.

Following this procedure the following compounds were prepared:

A. (R)-5-Benzyloxycarbonylamino-3-(N-methylpyrrolidin-2-ylmethyl)-1H-indole

Benzyl chloroformate was used. Column chromatography using elution with triethylamine/acetone/ethyl acetate [2:10:88] afforded the title compound as an off-white foam: $^{13}$C NMR (CDCl$_3$) δ163.3, 136.4, 133.6, 129.8, 128.6, 128.2, 127.9, 126.0, 123.2, 113.8, 111.4, 110.1, 66.8, 66.5, 57.5, 40.8, 31.5, 29.8, 21.8; LRMS (m/z, relative intensity) 363 (M+, 12), 279 (7), 184 (7), 171 (33), 108 (100); HRMS: calculated for C$_{22}$H$_{25}$N$_3$O$_2$ 363.1949, found 363.1926. Anal. calcd for C$_{22}$H$_{25}$N$_3$O$_2$.0.4 C$_4$H$_8$O$_4$ [ethyl acetate]: C, 71.09; H, 7.13; N, 10.54. Found: C, 70.82; H, 7.03; N, 10.58.

B. (R)-3-(N-Methylpyrrolidin-2-ylmethyl)-5-methylsulfonamido-1H-indole

Methanesulfonyl chloride was used. Column chromatography using elution with triethylamine/acetone/ ethyl acetate [1:3:6] afforded the title compound as a white foam: $^{13}$C NMR (CDCl$_3$) δ134.9, 128.3, 128.2, 123.6, 119.3, 115.0, 113.9, 112.0, 66.7, 57.3, 40.7, 38.7, 31.3, 29.4, 21.7; HRMS: calculated for C$_{15}$H$_{21}$N$_3$O$_2$S [with $^{32}$S] 307.1356, found 307.1323.

C. (R)-5-Acetylamino-3-(N-methylpyrrolidin-2-ylmethyl)-1H-indole

Acetyl chloride was used. Column chromatography using elution with triethylamine/acetone/ethyl acetate [1:3:6] afforded the title compound as a white foam: $^{13}$C NMR (acetone-d$_6$) δ168.3, 134.4, 132.2, 128.7, 124.1, 115.7, 113.8, 111.6, 110.2, 67.3, 58.0, 40.9, 31.9, 30.5, 24.1, 22.5; LRMS (m/z, relative intensity) 271 (M+, 39), 241 (4), 207 (5), 187 (20), 144 (20), 84 (100); HRMS: calculated for C$_{16}$H$_{21}$N$_3$O 271.1686, found 271.1693. Anal. calcd for C$_{16}$H$_{21}$N$_3$O.1.15 H$_2$O: C, 65.80; H, 8.04; N, 14.39. Found: C, 65.99; H, 7.90; N, 13.99.

D. (R)-5-N,N-Dimethylaminocarbonylamino-3-(N-methylpyrrolidin-2-ylmethyl)-1H-indole Dimethylcarbamyl chloride was used. Column chromatography using elution with methylene chloride/methanol/ammonium hydroxide [9:1:0.1] afforded the title compound as an off white foam: $^1$H NMR (CDCl$_3$) δ8.95 (br s, 1H), 7.49 (br s, 1H), 7.15–7.06 (m, 2H), 6.82 (d, J=1.9 Hz, 1H), 6.44 (br s, 1H), 3.12–3.05 (m, 2H), 3.00 (s, 6H), 2.58–2.40 (m, 2H), 2.40 (s, 3H), 2.18 (br q, J=8.1 Hz, 1H), 1.83–1.47 (m, 4H); $^{13}$C NMR (CDCl$_3$) δ157.2, 133.8, 130.5, 127.7, 123.2, 117.8, 113.0, 112.0, 111.3, 66.5, 57.4, 40.6, 36.4, 31.4, 29.8, 21.7; LRMS (m/z, relative intensity) 300 (M+, 50), 217 (10), 171 (20), 84 (100); HRMS: calculated for C$_{17}$H$_{24}$N$_4$O 300.1952, found 300.1957.

E. (R)-5-Trifluoroacetylamino-3-(N-methylpyrrolidin-2-ylmethyl)-1H-indole

Trifluoroacetic anhydride was used. Column chromatography using elution with methylene chloride/methanol/ammonium hydroxide [9:1:0-.1] afforded the title compound as an off white foam: $^1$H NMR (CDCl$_3$) δ8.99 (br s, 1H) 7.80 (br s, 1H), 7.27–7.19 (m, 2H), 6.95 (d, J=1.4 Hz, 1H0, 3.16–3.08 (m, 2H), 2.58 (dd, J=9.4 and 13.5 Hz, 1H). 2.57–2.43 (m, 1H), 2.43 (m, 1H), 2.43 (s, 3H), 2.22 (dd, J=9.2 and 17.5 Hz, 1H), 1.85–1.46 (m, 4H); $^{13}$C NMR (CDCl$_3$) δ134.5, 127.7, 126.9, 123.8, 116.1, 113.9, 111.9, 111.6, 104.1, 66.6, 57.3, 40.6, 31.3, 29.5, 21.7; HRMS: calculated for C$_{16}$H$_{18}$F$_3$N$_3$O 325.1403, found 325.1378.

EXAMPLE 16

(R)-3-(N-Methylpyrrolidin-2-ylmethyl)-5-(2-methylsulfonamidomethyl)-1H-indole

To a stirred mixture of (R)-5-aminomethyl-3-(N-methylpyrrolidin-2-ylmethyl)-1H-indole (0.113 g, 0.46 mmol) and pyridine (50 μL, 0.93 mmol, 2.0 eq) in a solution of dimethylformamide and acetonitrile (1: 3, respectively, 2 mL total) at 0° C. under nitrogen was added methanesulfonyl chloride dropwise (44 μL, 0.56 mmol, 1.3 eq). The resulting reaction solution was stirred at room temperature under nitrogen for 1 hour, and then it was evaporated under reduced pressure. The residual oil was column chromatographed using silica gel (6 g) and elution with methylene chloride/methanol/ammonium hydroxide [9:1:0.1] afforded the title compound (0.044 g, 0.14 mmol, 30%) as a white foam: $^1$H NMR (CDCl$_3$) δ8.25 (br s, NH), 7.54 (br s, 1H), 7.35 (d, J=8.4 Hz, 1H), 7.17 (dd, J=1.67 and 8.4 Hz, 1H), 7.06 (d, J=1.8 Hz, 1H), 4.78 (br s, NH), 4.42 (s, 2H), 3.20–3.12 (m, 2H), 2.87 (s, 3H), 2.64 (dd, J=9.4 and 13.9 Hz, 1H). 2.54–2.43 (m, 1H), 2.47 (s, 3H), 2.25 (dd, J=9.3 and 17.3, 1H), 1.86–1.52 (m, 4H); $^{13}$C NMR (CDCl$_3$) δ135.8, 127.8, 127.3, 123.0, 122.0, 118.5, 113.7, 111.6, 66.7, 57.4, 47.9, 40.9, 40.7, 31.3, 29.5, 21.7; LRMS (m/z relative intensity) 321 (28), 320 (M+, 26), 237 (51), 157 (100), 143 (64), 129 (78); HRMS: calculated for C$_{16}$H$_{22}$N$_3$O$_2$S 320.1435, found 320.1453.

EXAMPLE 17

General Synthesis of Allylsulphonamides

A. Allylsulphonamide

The title compound was prepared by the method of M. A. Belous and I. Ya. Postouski, *Zhur. Obschei. Khim.*, 1950, 20, 1701.

B. N-Methylallylsulphonamide

The title compound was prepared by an analogous procedure to above by using methylamine instead of ammonia. Anal. Calcd for C$_5$H$_{11}$NO$_2$S: C, 40.25; H, 7.43; N, 9.38. Found: C, 40.51; H, 7.37; N, 9.70.

EXAMPLE 18

Preparation of Ethylallylsulphone

The title compound was prepared by the method of R. J. Palmer and C. J. M. Stirling., *J. Amer. Chem. Soc.*, 1980, 102, 7888.

EXAMPLE 19

General Synthesis of Vinyl Sulphonamides

Where the required vinylsulphonamide was not commercially available, they were prepared by the following procedure based on the procedure described in *Zhur. Obschei. Khim.*, 1959, 29, 1494.

A. N,N-Dimethylvinylsulphonamide

To a stirred solution of chloroethylsulphonyl chloride (25 g, 153 mmol) in dry diethyl ether (150 mL) at −10° C., was added dropwise a solution of dimethylamine (30.5 mL, 460 mmol) in dry diethyl ether (100 mL) over 5 minutes. After stirring for 90 minutes at −10° C. the solution was filtered and evaporated in vacuo. The residue was distilled to give the title compound (9.5 g, 46%): b.p. 120°–122° C. (20 mm Hg). Anal. Calcd for C$_4$N$_9$HO$_2$S: C, 35.54; H, 6.71; N, 10.36%. Found: C, 35.36; H, 6.37; N, 10.19.

B. The following examples were prepared by the general procedure above, using the appropriate amine starting material. Purification was by distillation or column chromatography.

| | | $R_2NSO_2-CH=CH_2$ | | |
|---|---|---|---|---|
| | | Analysis % (Theoretical in brackets) | | |
| $R_2N$ | Isolated Form | C | H | N |
| MENH— | Oil b.p. 93–5° C. (0.05 mm Hg) | Literature compound U.S. Pat. No. 3,761,473 | | |
| ⟨N—⟩ (piperidine) | Oil | 47.97 (47.97 | 7.41 7.48 | 7.81 7.99) |
| ⟨N—⟩ (pyrrolidine) | Oil | 44.73 (44.70 | 6.80 6.88 | 8.62 8.69) |
| $nPr_2N-$ | Oil | 50.37 (50.23 | 8.79 8.96 | 7.68 7.32) |
| nPrNH— | Oil | 40.22 (40.24 | 7.35 7.43 | 9.1 9.39) |
| ⟨N—⟩ (azetidine) | Oil | 40.51 (40.79 | 5.85 6.16 | 9.35 9.52) |
| iPrNH— | Oil | 40.42 (40.25 | 7.33 7.43 | 9.30 9.39) |

EXAMPLE 20

General Synthesis of Vinyl Sulphones

Where the required vinyl sulphone was not commercially available, they were prepared from the corresponding thiols using the procedure described by J. M. Gaillot, Y Gelas-Mialhe and R. Vessiere *Can. J. Chem.*, 1979, 57, 1958. The following examples are representative.

| | | Analysis % (Theoretical In brackets) | |
|---|---|---|---|
| R | Isolated Form | C | H |
| | | $RS-CH_2CH_2-OH$ | |
| nPr | Oil 1/16 EtOAc | 48.68 | 9.79 |
| nBu | Oil 1/5 $H_2O$ | (48.76 | 10.06) |
| T.l.c - Rf. 0.26 (SiO$_2$, Ether/Hexane 1:1) | | | |
| | | $RS-CH_2CH_2-Cl$ | |
| nPr | Oil 1/5 $H_2O$ 1/30 $CH_2Cl_2$ | 41.63 (41.65 | 7.60 7.69) |
| nBu | Oil 1.0 $H_2O$ | 42.31 (42.21 | 7.84 8.27) |
| | | $RSO_2-CH_2CH_2Cl$ | |
| nPr | Oil | 34.75 (35.19 | 6.68 6.50) |
| nBu | Oil 1/15 $CH_2Cl_2$ | 38.41 (38.27 | 7.01 6.95) |
| | | $RSO_2-CH=CH_2$ | |
| nBu | Oil | 48.95 (48.62 | 8.07 8.16) |

EXAMPLE 21

General Synthesis of indoles with 5-alkenyl substituents

A. (R)-5-trans-(2-N,N-Dimethylaminocarbonylethenyl)-3-(N-methylpyrrolidin-2-ylmethyl)-1H-indole A mixture of N,N-dimethylacrylamide (134 μL, 1.3 mmol), tri-o-tolylphosphine (91 mg, 0.3 mmol), palladium (II) acetate (15 mg, 0.07 mmol), triethylamine (280 μL, 2 mmol) and (R)-5-bromo-3-(N-methylpyrrolidin-2-ylmethyl)-1H-indole was dissolved in anhydrous acetonitrile (5 mL) and refluxed for 24 hours under nitrogen. The reaction was partitioned between ethyl acetate and aqueous sodium carbonate. The dried ($Na_2SO_4$) organic phase was evaporated and the residue purified by column chromatography on silica gel, eluting with $CH_2Cl_2$:MeOH: $NH_4OH$ 96:3.5:0.5 to afford the title compound as a white foam (145 mg, 47%). Anal. Calcd for $C_{19}H_{25}N_3O.⅑\ CH_2Cl_2$: C, 71.56; H, 7.87; N, 13.10%. Found: C, 71.29; H, 8.15; N, 13.05.

B. The following examples were prepared using the above procedure with the appropriate alkene starting material (available commercially, or prepared by routes outlined in this patent).

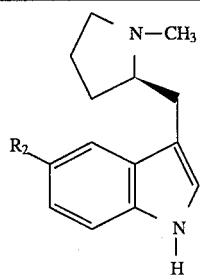

| | | Analysis % (Theoretical in brackets) | | | $[\sigma]^{26}_D$ (c = 0.1 |
|---|---|---|---|---|---|
| $R^2$ | Isolated Form | C | H | N | MeOH) |
| $MeSO_2CH=CH$ | Foam 3/10 $CH_2Cl_2$ | 60.45 (60.42 | 6.43 6.62 | 8.33 8.15) | |
| $PhSOCH=CH$ | Foam 1/10 $CH_2Cl_2$ | 68.04 (68.24 | 6.27 6.27 | 6.99 7.20) | |

-continued

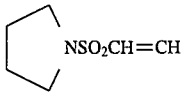

| R² | Isolated Form | C | H | N | $[\alpha]^{26}_D$ (c = 0.1 MeOH) |
|---|---|---|---|---|---|
| | | Analysis % (Theoretical in brackets) | | | |
| NH₂SO₂CH=CH | Foam 1/3 MeOH 1/3 H₂O | 58.56 (58.39 | 6.80 6.85 | 12.19 12.51) | |
| EtSOCH=CH | Foam 1/20 CH₂Cl₂ 1/4 H₂O | 66.70 (66.66 | 7.35 7.62 | 8.64 8.62) | |
| 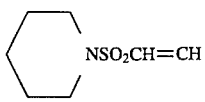NSO₂CH=CH | Foam 1/8 CH₂Cl₂ 1/2 H₂O | 61.74 (61.49 | 6.93 7.22 | 10.53 10.69) | |
| nBuSO₂CH=CH | Foam 1/4 CH₂Cl₂ 1/10 EtOH | 63.56 (63.59 | 7.77 7.57 | 7.22 7.25) | |
| Me₂NSO₂CH=CH | Foam 1/3 H₂O | 61.14 (61.19 | 7.06 7.27 | 11.57 11.89) | |
| 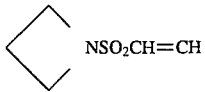NSO₂CH=CH | Foam 1/2 CH₂Cl₂ 1/4 H₂O | 59.64 (59.43 | 6.82 7.07 | 9.83 9.67) | |
| nPr₂NSO₂CH=CH | Foam 1.0 H₂O 1/10 CH₂Cl₂ | 61.48 (61.72 | 7.76 8.25 | 9.69 9.77) | |
| nPrNHSO₂CH=CH | Foam 1/10 CH₂Cl₂ 1/3 H₂O | 61.07 (61.01 | 7.12 7.49 | 10.91 11.18) | |
| ▽NSO₂CH=CH | Foam 1/3 CH₂Cl₂ 1 H₂O | 56.83 (56.39 | 6.40 6.87 | 10.36 10.36) | +34° |
| IPrNHSO₂CH=CH | Foam 1/6 CH₂Cl₂ | 61.03 (61.27 | 7.42 7.33 | 11.17 11.19) | +30° |
| PhSO₂CH₂CH=CH | Foam 1/6 CH₂Cl₂ | 68.21 (68.27 | 6.81 6.50 | 7.15 6.87) | |
| Me₂NSO₂CH₂CH=CH | Foam 1/20 CH₂Cl₂ | 62.54 (62.55 | 7.50 7.46 | 11.21 11.48) | |
| NH₂SO₂CH₂CH=CH | Foam 0.1 CH₂Cl₂ 1.0 MeOH | 58.50 (58.13 | 6.93 7.30 | 11.22 11.24) | |
| EtSO₂CH₂CH=CH | Foam | 65.56 (65.86 | 7.47 7.56 | 8.00 8.08) | |
| PhCONHCH₂CH=CH | Foam 0.1 CH₂Cl₂ | 75.69 (75.78 | 6.97 7.18 | 10.76 11.00) | +70° |
| MeSO₂NHCH₂CH=CH | Foam 0.1 CH₂Cl₂ | 61.05 (61.07 | 7.31 7.14 | 11.12 11.80) | |

C.) The following compounds could be prepared by the procedure a) above but using the corresponding beta-chloroethylsulphone as starting material instead of an alkene. These reactions were preferably carried out in the presence of 3–6 equivalents of triethylamine.

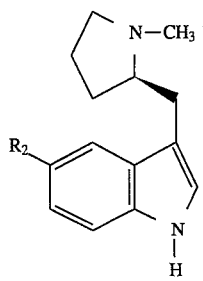

| R² | Isolated Form | Analysis % (Theoretical in brackets) | | | $[\alpha]^{26}_D$ (c = 0.1 MeOH) |
|---|---|---|---|---|---|
| | | C | H | N | |
| nPrSO₂CH=CH | Foam 1/8 CH₂Cl₂ 1/3 H₂O | 62.93 (63.25 | 7.15 7.47 | 7.71 7.71) | |
| Cl-C₆H₄-SO₂CH=CH | Foam 0.15 CH₂Cl₂ | 62.22 (62.20 | 5.37 5.49 | 6.52 6.55) | +48° |

EXAMPLE 22

General Procedure for Hydrogenation of 5-alkenylindoles

A typical procedure is as follows:

A. (R)-5-(2-Aminosulphonylethyl)-3-(N-methylpyrrolidin-2-ylmethyl)-1H-indole (R)-5-(2-Aminosulphonylethenyl)-3-(N-methylpyrrolidin-2-ylmethyl)-1H-indole (157 mg, 0.5 mmol) was dissolved in absolute ethanol (10 mL) and added to a solution of ethanolic hydrogen chloride (25 ml) (prepared from acetyl chloride (38 μL, 0.53 mmol) and absolute ethanol (25 mL)). 10% palladium-on-carbon (125 mg) was added. This solution was hydrogenated under a hydrogen atmosphere (15 p.s.i.) at room temperature for 18 hours. The resultant reaction mixture was filtered through diatomaceous earth (Celite trademark or Arbacell-trademark)) washed with absolute ethanol and the combined filtrates evaporated in vacuo. The residue was purified by column chromatography on silica gel, eluting with a gradient solvent mixture up to CH₂Cl₂: MeOH:NH₄OH 93:7:1 to give the title compound as a colourless oil (80 mg, 51%). Anal. Calcd for C₁₆H₂₃N₃O₂S.¼ MeOH. ⅓ H₂O: C, 58.21; H, 7.36; N, 12.54. Found: C, 58.60; H, 7.40; N, 12.57 $[\alpha]^{25}_D$=+69° (c=0 1, MeOH)

B. The following examples were prepared by an analogous procedure to a) above.

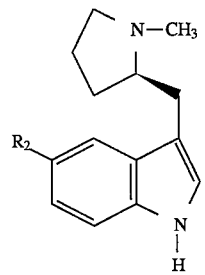

| R² | Isolated Form | Analysis % (Theoretical in brackets) | | | $[\alpha]^{26}_D$ (c = 0.1 MeOH) |
|---|---|---|---|---|---|
| | | C | H | N | |
| Me₂NSO₂CH₂CH₂ | Oil 1/20 CH₂Cl₂ | 61.52 (61.31 | 7.40 7.67 | 11.49 11.89) | +48° |
| Me₂NCOCH₂CH₂ | Oil 1/10 CH₂Cl₂ | 70.96 (71.29 | 8.52 8.46 | 12.84 13.06) | +76.2° |
| MeSO₂CH₂CH₂ | Gum 1/4 H₂O | 62.76 (62.83 | 7.29 7.60 | 8.41 8.62) | +83° |
| EtSOCH₂CH₂ | Oil | 61.39 (61.27 | 7.69 8.03 | 8.16 7.83) | |

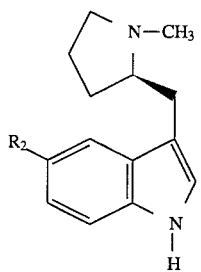

| R[2] | Isolated Form | C | H | N | $[\alpha]^{26}_D$ (c = 0.1 MeOH) |
|---|---|---|---|---|---|
| ⬡NSO$_2$CH$_2$CH$_2$ (cyclohexyl) | Foam 2/3 H$_2$O | 62.73 (62.81 | 7.60 8.11 | 10.64 10.47) | +57° |
| PhSO$_2$CH$_2$CH$_2$CH$_2$ | Oil 2/3 H$_2$O | 67.56 (67.60 | 7.27 7.23 | 6.96 6.85) | |
| NH$_2$SO$_2$CH$_2$CH$_2$CH$_2$ | Foam 0.65 CH$_2$Cl$_2$ | 56.78 (56.26 | 7.16 6.60 | 10.34 10.75) | |
| ⬠NSO$_2$CH$_2$CH$_2$ (pyrrolidinyl) | Foam 1/2 H$_2$O | 62.45 (62.47 | 7.48 7.86 | 10.74 10.93) | |
| Me$_2$NSO$_2$CH$_2$CH$_2$CH$_2$ | Oil 0.1 CH$_2$Cl$_2$ | 62.03 (61.66 | 7.76 7.91 | 10.41 11.16) | |
| $^n$BuSO$_2$CH$_2$CH$_2$ | Oil 1/3 CH$_2$Cl$_2$ | 62.28 (62.48 | 7.50 7.91 | 7.23 7.17) | +48° |
| nPrNHSO$_2$CH$_2$CH$_2$ | Foam 1/4 H$_2$O | 62.07 (62.01 | 7.95 8.08 | 11.17 11.42) | +57° |
| $^n$PrSO$_2$CH$_2$CH$_2$ | Foam 1/20 CH$_2$Cl$_2$ 3/4 H$_2$O | 62.80 (62.47 | 7.72 8.15 | 7.24 7.65) | +50° |
| $^n$Pr$_2$NSO$_2$CH$_2$CH$_2$ | Gum 1.0 H$_2$O | 62.28 (62.37 | 8.38 8.80 | 10.03 9.92) | +40° |
| EtSO$_2$CH$_2$CH$_2$CH$_2$ | Glass 0.5 CH$_2$Cl$_2$ | 59.10 (59.90 | 7.57 7.47 | 7.04 7.16) | |
| ◇NSO$_2$CH$_2$CH$_2$ (cyclobutyl) | Foam 1/3 CH$_2$Cl$_2$ | 59.07 (59.56 | 7.10 7.15 | 10.80 10.78) | +30° |
| IPrNHSO$_2$CH$_2$CH$_2$ | Foam 1/8 CH$_2$Cl$_2$ | 61.59 (61.39 | 7.88 7.88 | 11.16 11.23) | +58° |

EXAMPLE 23

General Synthesis of (R)-5-(2-Ethylsulphonylethyl)-3-(pyrrolidin-2-ylmethyl)-1H-indole A. (R)-3-(N-Benzyloxycarbonylpyrrolidin-2-yl-methyl)-5-bromo-1H-indole (R)-3-(N-Benzyloxycarbonylpyrrolidin-2-yl-carbonyl)-5-bromo-1H-indole(0.67 g, 1.57 mmol) was dissolved in anhydrous tetrahydrofuran (20 mL) and at room temperature under nitrogen was added lithium borohydride (2 molar in tetrahydrofuran) (1.2 mL, 2.4 mmol). The reaction mixture was stirred at room temperature for 3 hours and warmed to reflux for 16 hours. After cooling to room temperature, 2NHCl (10 mL) was added dropwise and the reaction mixture partitioned between ethyl acetate and water. The separated organic phase was washed with saturated aqueous sodium hydrogen carbonate (2×), brine (1×), dried (Na$_2$SO$_4$), and evaporated in vacuo to give a colourless oil. Purification by column chromatography on silica gel, eluting with dichloromethane gave the title compound as an oil (0.32 g). TLC (SiO$_2$.CH$_2$Cl$_2$): R$_f$=0.2.

B. (R)-5-(Ethylsulphonylethenyl)-3-(N-Benzyloxy carbonylpyrrolidin-2-ylmethyl)-1H-indole The compound from procedure a) above was coupled with ethyl vinylsulphone under standard conditions described above, to give the title compound as a foam. Anal. Calcd for C$_{25}$H$_{28}$N$_2$O$_4$S.⅛ CH$_2$Cl$_2$: C, 65.15; H, 6.15; N, 6.05. Found: C, 65.16; H, 6.17; N, 5.97. $[\alpha]^{25}_D$=−50° (0.1, MeOH).

C. (R)-5-(2-Ethylsulphonylethyl)-3(pyrrolidin-2-ylmethyl)-1H-indole

The compound prepared in procedure b) above, was hydrogenated under the standard condition described above, to give the title compound as a foam. Anal. Calcd for C$_{17}$H$_{24}$N$_2$O$_2$S.½ CH$_2$Cl$_2$: C, 63.07; H, 7.48; N, 8.63. Found: C, 62.90; H, 7.25; N, 8.58. $[\alpha]^{25}_D$=−11° (c=0.1, MeOH).

EXAMPLE 24

General Synthesis of (R)-3-(N-alkyl-pyrrolidin-2-ylmethyl)indoles

A. (R)-3-(N-Ethylpyrrolidin-2-ylmethyl)-5-2-ethylsulphonylethyl)-1H-indole

To a solution of (R)-3-(pyrrolidin-2-ylmethyl)-5-(2-ethylsulphonylethyl)-1H-indole (0.27 g, 0.8 mmol) in dimethylformamide (dried over 4A sieves) (5 mls), was added sodium carbonate (90 mgs) and ethyl iodide (0.07 mls, 0.88 mmol) at room temperature. The mixture was heated at 120° C. under nitrogen for 16 hours. After cooling to room temperature the reaction mixture was partitioned between ethyl acetate and water. The separated organic phase was washed with water (3×), dried ($Na_2SO_4$) and evaporated in vacuo to give an oil. Purification by column chromatography on silica gel, eluting with $CH_2Cl_2$: EtOH: $NH_4OH$ (90:10:0.5) gave the title compound as a gum (100 mgs). Anal. Calcd for $C_{19}H_{28}N_2O_2S \cdot ¼ CH_2Cl_2 \cdot ½ H_2O$: C, 61.04; H, 7.85; N, 7.40. Found: C, 60 80; H, 7 69; N, 7.48.$[\alpha]^{25}_D$= +60° (c=0.1, MeOH)

B. The following examples were prepared using the procedure described in a) above but with the appropriate alkyl halide in place of ethyl iodide. The alkyl halide could be iodide or bromide with the optional presence of sodium iodide. Solvents used were either dimethylformamide or dimethylacetamide.

8.18; N, 12.46 Found: C, 75.50; H, 8.51; N, 12.09.$[\alpha]^{25}_D$= +60.2° (c=0.088, $CHCl_3$).

EXAMPLE 26

(R)-3-(N-Benzyloxycarbonylpyrrolidin-2-ylcarbonyl)-5-bromo-1H-indole

Two solutions containing the reactants were prepared separately as follows: To a stirred solution of N-benzyloxycarbonyl-D-proline (1.0 g) in anhydrous dichloromethane (2 ml) and N,N-dimethylformamide (1 drop) was added oxalyl chloride (0.5 mL), and the resulting solution was stirred at room temperature for 1.5 hours. The solution was evaporated under reduced pressure, and remaining solvent was removed under high vacuum to give the N-benzyloxycarbonyl-D-proline acid chloride. At the same time, a solution of ethyl magnesium bromide (1.4 mL of a 3M solution in ether) was added dropwise over 5 minutes to a stirred solution of 5-bromoindole (0.75 g) in dry ether (18 mL). The

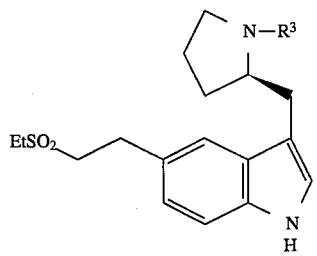

| R³ | Isolated Form | Analysis % (Theoretical in brackets) | | | $[\sigma]^{26}_D$ |
|---|---|---|---|---|---|
| | | C | H | N | c = 0.1 MeOH |
| iPr | Gum 1/10 $CH_2Cl_2$ 1/4 $H_2O$ | 64.18 (64.29 | 8.17 8.24 | 7.55 7.46) | +24° |
| * $CH_3CH(CH_2CH_3)$ (Isomer 1- R.f. 0.40 $SiO_2$, $CH_2Cl_2$: MeOH: $NH_3$ (90:10:1) | Gum 1/2 $CH_2Cl_2$ 1/4 $H_2O$ | 60.68 (60.97 | 7.91 7.97 | 7.08 6.62) | –3° |
| * $CH_3CH(CH_2CH_3)$ (Isomer 2 - R.f. 0.38 $SiO_2$, $CH_2Cl_2$:MeOH:$NH_3$ (90:10:1)) | Gum 1/8 $CH_2Cl_2$ | 65.19 (65.53 | 8.13 8.40 | 7.45 7.24) | +26° |
| nPr | Gum 1/20 $CH_2Cl_2$ 3/5 $H_2O$ | 64.04 (63.77 | 8.19 8.36 | 7.52 7.42) | +62° |
| $(CH_3)_2CHCH_2$ | Gum 1/2 $H_2O$ | 65.32 (65.40 | 8.49 8.63 | 6.87 7.26) | +80° |
| * $CH_3(CH_2CH_2)CHCH_2$ (S-isomer) | Gum 2/3 $H_2O$ | 65.72 (65.63 | 8.82 8.85 | 7.10 6.96) | +65° |

EXAMPLE 25

(R)-3-(N-Methylpyrrolidin-2-ylmethyl)-1H-indole (R)-5-Bromo-3-(N-methylpyrrolidin-2-yl-methyl)-1H-indole (60 mg, 0.2 mmol) was dissolved in ethanol (1 mL) and hydrogenated over 10% palladium on carbon (45 mg) at 60 p.s.i. of hydrogen pressure at room temperature for 16 hours. The reaction mixture was evaporated to dryness, and the residue partitioned between ethyl acetate and 10% aqueous sodium carbonate. The organic phase was dried ($Na_2SO_4$), and evaporated in vacuo. The resulting residue was purified by column chromatography on silica gel (eluting with 89:10:1 $CH_2Cl_2$.MeOH:$NH_4OH$) to give the title compound (28 mg). Anal. Calcd for $C_{14}H_{18}N_2 \cdot \frac{1}{8} CH_2Cl_2$ C, 75.42; H, mixture was stirred at room temperature for 10 minutes, heated under reflux for 2 hours, then cooled to −30° C. A solution of the above N-benzyloxycarbonyl-D-proline acid chloride in dry ether (4 mL) was added dropwise with stirring, and stirring was continued for a further 1 hour. Ether (12.5 mL) and saturated aqueous sodium bicarbonate (6.5 mL) were added, and the temperature was allowed to rise to room temperature. Stirring was continued for a further 10 minutes and the mixture was filtered. The solid was washed well with ethyl acetate, and the combined filtrate and washings were washed with water, brine and dried ($MgSO_4$). Evaporation of the solvent gave an oil which was chromatographed on silica gel. Elution with ethyl acetate gave the title compound as a foam (0.82 g): LRMS m/z (relative intensity) 428 (M+ with $^{81}$Br, 5) 426 (M+ with $^{79}$Br, 5), 224 (19), 222

EXAMPLE 27

(R)-5-Bromo-3-(N-methylpyrrolidin-2-ylmethyl)-1H-indole

A solution of (R)-3-(N-benzyloxycarbonyl-pyrrolidin-2-ylcarbonyl)-5-bromo-1H-indole (1.04 g) in dry tetrahydrofuran (20 mL) was added dropwise to a stirred suspension of lithium aluminium hydride (0.27 g) in dry tetrahydrofuran (15 mL) at room temperature under an atmosphere of dry nitrogen. The mixture was heated under reflux with stirring for 18 hours and then cooled. Additional lithium aluminium hydride (50 mg) was added and refluxing was continued for an additional 3 hours. The mixture was again cooled, lithium aluminium hydride (40 mg) was added, and refluxing was continued for a further 18 hours. The mixture was cooled and water (0.44 mL) was carefully added with stirring, followed by 20% aqueous sodium hydroxide (0.44 mL), followed by more water (1.33 mL). The mixture was diluted with ethyl acetate and filtered through Celite (trademark) filter aid. The filtrate was washed with water, brine and then dried ($Na_2SO_4$). Evaporation of the solvent gave an oil which was chromatographed on silica gel. Elution with dichloromethane/ethanol/concentrated aqueous ammonia (90:10:0.5) gave the title compound as a solid (0.51 g), m.p. 137°–140° C. (from dichloromethane/hexane); IR (KBr) 1620, 1595, 1570, 1480, 1450, 1435 $cm^{-1}$; $^1H$ NMR (DMSO-$d_6$) δ11.05 (br s, 1H), 7.65 (br d, 1H), 7.31 (d, J=8.6 Hz, 1H), 7.21 (br d, 1H), 7.16 (dd, J=1.8 and 8.6 Hz, 1H), 3.03–2.94 (m, 2H), 2.47 (dd, J=9.2 and 14.0 Hz, 1H), 2.36–2.26 (m, 1H), 2.33 (s, 3H), 2.09 (dd, J=8.7 and 17.3 Hz, 1H), 1.73–1.38 (m,4H); $^{13}C$ NMR (DMSO-$d_6$) δ134.8, 129.5, 124.7, 123.2, 120.7, 113.4, 112.1, 110.9, 66.1, 57.0, 40.5, 30.9, 29.1, 21.6; LRMS, m/z (relative intensity) 294 ($M^+$ with $^{81}Br$, 1) 293 (2) 292 ($M^+$ with $^{79}Br$, 1), 210 (14), 208 (15), 154 (8), 129 (42), 128 (19), 101 (26) 85 (57) 84 (100), 83 (30); $[α]^{25}_D$=+62° (methanol, c=0.10). Anal Calcd for $C_{14}H_{17}N_2Br$. 0.25 $H_2O$: C, 56.48; H, 5.93; N, 9.41. Found: C, 56.65; H, 5.69; N, 9.23.

EXAMPLE 28

(R)-5-(2-Ethylsulphonylethenyl)-3-(N-methylpyrrolidin-2-ylmethyl)-1H-indole

A mixture of (R)-5-bromo-3-(N-methylpyrrolidin-2-ylmethyl)-1H-indole (0.25 g), ethyl vinyl sulphone (0.14 g), tri-o-tolylphosphine (0. 075 g), palladium (II) acetate (0. 013 g), triethylamine (0.25 mL) and acetonitrile (3 mL) was heated under reflux for 17 hours in an atmosphere of nitrogen. The mixture was evaporated and the residue was chromatographed on silica gel. Elution with dichloromethane/ethanol/concentrated aqueous ammonia (90:8:1) gave the title compound as a foam (0.185 g): TLC (dichloromethane/-ethanol/concentrated aqueous ammonia, 90:10:1): $R_f$=0.5. Anal. Calcd for $C_{18}H_{24}N_2O_2S$. 0.2 $CH_2Cl_2$: C, 62.55; H, 7.04; N, 8.02. Found: C, 62.65; H, 6.94; N, 7.92.

EXAMPLE 29

(R)-5-(2-Ethylsulphonylethyl)-3-(N-methylpyrrolidin-2-ylmethyl) 1H-indole (R)-5-(2-Ethylsulphonylethenyl)-3-(N-methylpyrrolidin-2-ylmethyl)-1H-indole (157 mg) was dissolved in a mixture of ethanolic hydrogen chloride [prepared by addition of acetyl chloride (0.043 mL) to ethanol (10 mL)], N,N-dimethylformamide (7.5 mL) and water (0.1 mL) and the solution was shaken under a hydrogen atmosphere (15 psi) at room temperature for 18 hours in the presence of 10% palladium on carbon (150 mg). The mixture was filtered through Arbacel (trade mark) filter aid and the residue was washed well with ethanol. The combined filtrate and washings were evaporated under reduced pressure and the residual oil was partitioned between ethyl acetate and 2M aqueous sodium carbonate solution. The organic layer was separated, washed three times with water followed by brine and then dried ($Na_2SO_4$). Evaporation of the solvent gave an oil which was chromatographed on silica gel. Elution with dichloromethane/methanol/ concentrated aqueous ammonia (90:10:1) gave the title compound as a gum (110 mg): TLC ($CH_2Cl_2/C_2H_5OH/NH_3$; 90:10:1): $R_f$=0.3; $[α]^{25}_D$=+62° (methanol, c=0.10). Anal. Calcd for $C_{18}H_{26}N_2O_2S$. 0.05 $CH_2Cl_2$: C, 63.21; H, 7.67; N, 8.17. Found: C, 63.55; H, 7.61; N, 8.41.

EXAMPLE 30

(R)-5-(2-Ethylsulphonylethyl)-3-(N-methylpyrrolidin-2-ylmethyl)-1H-indole hemisuccinate A solution of succinic acid (69 mg) in hot ethanol (3.5 mL) was added slowly with stirring to a solution of (R)-5-(2-ethylsulphonylethyl)-3-(N-methylpyrrolidin-2-ylmethyl)-1H-indole free base (390 mg) in ethanol (3.5 mL). The solution was evaporated and the residue was triturated first with ether and then with ethyl acetate to give the title compound as a solid (375 mg): mp 59°–62° C.: $[α]^{25}_D$=+36° (methanol, c=0.10). Anal Calcd for $C_{18}H_{26}N_2O_2S$. 0.5 $C_4H_6O_4$. 0.25 $CH_3CO_2C_2H_5$. 0.5 $H_2O$: C, 59.00; H, 7.42; H, 6.68. Found: C, 59.17; H, 7.37; N, 6.73.

EXAMPLE 31

(R)-5-(2-Benzenesulphonylethenyl)-3-(N-methylpyrrolidin-2-ylmethyl)-1H-indole hydrobromide A mixture of (R)-5-bromo-3-(N-methylpyrrolidin-2-ylmethyl)-1H-indole (0.25 g), phenylvinylsulphone (0.19 g), tri-o-tolylphosphine (0. 075 g), palladium (II) acetate (0. 0125 g), triethylamine (0.25 mL) and acetonitrile (2.5 mL) was heated under reflux for 42 hours in an atmosphere of nitrogen. The solvent was evaporated and the residue was chromatographed on silica gel. Elution with dichloromethane/methanol/concentrated aqueous ammonia (90:10:1) gave the title compound as a foam (0.24 g): Anal. Calcd for $C_{22}H_{24}N_2O_2S$. HBr. ⅓ $CH_2Cl_2$: C, 54.77; H, 5.29; N, 5.72. Found: C, 55.00; H, 4.85; N, 5.58.

EXAMPLE 32

(R)-5-(2-Benzenesulphonylethyl)-3-(M-methylpyrrolidin-2-ylmethyl)-1H-indole

A solution of (R)-5-(2-benzenesulphonylethenyl)-3-N-methylpyrrolidin-2-ylmethyl)-1H-indole hydrobromide (0.214 g) and 10% palladium on carbon (0.15 g) in a mixture of absolute ethanol (10 mL), N,N-dimethylformamide (1 mL) and water (2 drops) was shaken under a hydrogen atmosphere (15 psi) at room temperature for 18 hours. The mixture was filtered through Celite (trademark) filter aid and the residue was washed well with ethanol. The combined filtrate and washings were evaporated under reduced pressure and the residue was partitioned between ethyl acetate and 2M aqueous sodium carbonate solution. The organic layer was separated, washed three times with water, followed by brine and dried ($Na_2SO_4$). Evaporation of the solvent gave a gum which was chromatographed on silica gel. Elution with dichloromethane/methanol/concentrated aqueous ammonia (90:10:0.5) gave the title compound as a foam (0.096 g). Anal. Calcd for $C_{22}H_{26}N_2O_2 \cdot H_2O$: C, 65.97; H, 7.05; N, 7.00. Found: C, 65.51; H, 6.77; N, 7.45.

EXAMPLE 33

(R)-5-(2-Benzenesulphonylethyl)-3-(N-methylpyrrolidin-2-ylmethyl)-1H-indole hemisuccinate A solution of succinic acid (95 mg) in ethanol (5 mL) was added to a solution of (R)-5-(2-benzenesulphonylethyl)-3-(N-methylpyrrolidin-2-ylmethyl)-1H-indole free base (620 mg) in ethanol (5 mL). The solution was evaporated to give the title compound as a foam (680 mg): $[\alpha]^{25}_D=+29°$ (methanol, c=0.10). Anal. Calcd for $C_{22}H_{26}N_2O_2S \cdot 0.5 C_4H_6O_4 \cdot 0.33 C_2H_5OH \cdot 0.5 H_2O$; C, 63.59; H, 6.92; N, 6.01. Found: C, 63.52; H, 6.91; N, 6.12.

EXAMPLE 34

(R)-5-[2-(4-Methylphenylsulphonyl)ethenyl]-3-(N-methylpyrrolidin-2-ylmethyl)-1H-indole A mixture of (R)-5-bromo-3-(N-methylpyrrolidin-2-ylmethyl)-1H-indole (0.40 g), 4-methylphenylvinylsulphone (0.273 g), tri-o-tolylphosphine (0.085 g), palladium (II) acetate (0.031 g), triethylamine (0.42 g), and acetonitrile (20 mL) was heated under reflux for 16 hours in an atmosphere of nitrogen. The mixture was cooled and partitioned between ethyl acetate and 10% aqueous sodium bicarbonate solution. The organic layer was washed with brine, dried ($Na_2SO_4$) and evaporated. The residual orange oil was chromatographed on silica gel. Elution was commenced with dichloromethane/methanol (90:10), followed by dichloromethane/methanol/concentrated aqueous ammonia (90:10:0.25), gradually increasing the concentration of concentrated aqueous ammonia to 1%. The later product-containing fractions were evaporated to give the title compound as a foam (226 mg): $[\alpha]^{25}_D=+71°$ (methanol, c =0.10). Anal. Calcd for $C_{23}H_{26}N_2O_2S \cdot 0.15 CH_2Cl_2$: C, 68.27; H, 6.51; N, 6.88. Found: C, 68.26; H, 6.54; N, 6.99.

EXAMPLE 35

(R)-5-[2-(4-Methylphenylsulphonyl)ethyl-3-(N,-methylpyrrolidin-2-ylmethyl)-1H-indole A solution of (R)-5-[2-(4-methylphenylsulphonyl)ethenyl]-3-(N-methylpyrrolidin-2-ylmethyl)-1H-indole (0.18 g) and 10% palladium on carbon (0.20 g) in ethanolic hydrogen chloride [prepared from absolute ethanol (25 mL) and acetyl chloride (35 μL)] was shaken under a hydrogen atmosphere (15 psi) at room temperature for 16 hours. The reaction mixture was filtered through Celite (trademark) filter aid and the residue was washed well with ethanol. The combined filtrate and washings were evaporated under reduced pressure and the residue was partitioned between ethyl acetate and 2M aqueous sodium carbonate solution. The organic layer was saturated, washed three times with water, followed by brine and dried ($Na_2SO_4$). Evaporation of the solvent gave a gum which was chromatographed on silica gel. Elution with dichloromethane/methanol/concentrated aqueous ammonia (90:10:0.25) gave the title compound as a foam (108 mg): $[\alpha]^{25}_D=+30°$ (methanol, c=0.10). Anal. Calcd for $C_{23}H_{28}n_2O_2S \cdot 0.05 CH_2Cl_2 \cdot 0.5 H_2O$: C, 67.55; H, 7.15; N, 6.84. Found: C, 67.51; H, 7.04; N, 6.98.

EXAMPLE 36

4-(Nitrophenyl)methanesulphonyl chloride

To a stirred solution of sodium thiosulphate (72.0g, 0.291 mol) in water (75 mL) and methanol (50 mL) was added at room temperature, over 5 minutes, 4-nitrobenzyl chloride (50.0g, 0.291 mol). The resulting reaction mixture was heated to reflux and stirred, at reflux, for a further 2.25 hours. The reaction mixture was then cooled down and evaporated under reduced pressure, azeotroping with toluene to give a white solid (150 g). The white solid was added to a mixture of acetic acid (75 mL), water (100 mL) and ice, the reaction mixture cooled to 0° C. and chlorine gas passed through the system for 1.25 hours, maintaining the reaction temperature below 10° C. throughout. The excess chlorine gas was removed by purging the reaction mixture with nitrogen gas for 1.25 hours. The resulting slurry was filtered, drying the solid thus obtained in air. The title compound thus obtained (60.5 g) was used as such in Example 37 without further purification or characterization,

EXAMPLE 37

4-t-Butylaminosulphonylmethylnitrobenzene

To a cooled (ice bath) solution of t-butylamine (48.45 mL, 461 mmol) in dichloromethane (500 ml) was added dropwise, with stirring, a solution of the product of Example 36 (54.33 g, 231 mmol) in dichloromethane (500 mL). This addition was carried out over 15 minutes with the temperature maintained below 10° C. throughout. The reaction was then allowed to warm to room temperature and stirred for a further 12 hours. The reaction was then diluted with water (200 mL), the organic layer separated, washed sequentially with water and brine, dried ($MgSO_4$) and evaporated under reduced pressure to give the product as a brown solid. Recrystallization of the brown solid from ethanol gave the title compound as a white solid (49.0 g): mp, 156°–158° C.; TLC (dichloromethane/methanol 30:0.4): Rf=0.66. $^1H$ NMR (CDCl$_3$) δ8.25 (d, 2H), 7.6 (d, 2H), 4.40 (s, 2H), 4.10 (s, 1H), 1.38 (s, 9H). Anal. calcd. for $C_{11}H_{16}N_2O_4S$: C, 48.55; H, 5.97; N, 10.30. Found: C, 48.53; H, 5.92; N, 10.29.

EXAMPLE 38

4-t-Butylaminosulphonylmethylaniline

A solution of the product of Example 37 (1.17 g, 4.29 mmol) in absolute ethanol and 10% palladium on carbon (0.32 g) was stirred under a hydrogen atmosphere (60 psi) at 60° C. for 66 hours. The mixture was filtered through CELITE filter aid and the resulting solution evaporated under reduced pressure to give the product as a solid. Recrystallization from ethanol gave the title compound as a white solid (0.95 g): mp, 137°–138° C.; TLC (dichloromethane/methanol 30:0.4): Rf=0.43. $^1H$ NMR (CDCl$_3$) δ7.20 (d, 2H), 6.65 (d, 2H), 4.15 (s, 2H), 3.95 (br s, 1H), 3.75 (br s, 2H), 1.32 (s, 9H). Anal. calcd. for $C_{11}H_{18}N_2O_2S$: C, 54.51; H, 7.49; N, 11.56. Found: C, 54.76; H, 7.60; N, 11.43.

EXAMPLE 39

4-(t-Butylaminosulphonylmethyl)-2,6-dibromoaniline

To a stirred solution of the product of Example 38 (0.77 g, 3.17 mmol) in dichloromethane (15 mL) and methanol (15 mL) was added sodium bicarbonate (0.80 g, 9.53 mmol) with stirring, at 20° C. Bromine (0.315 mL, 6.11 mmol) was then added dropwise, to the resultant slurry. The resulting mixture was then stirred for 18 hours concentrated in vacuo and taken up in ethyl acetate/water (1:1). The aqueous layer was separated and extracted with ethyl acetate. The combined organic layers were then washed with water, dried (MgSO$_4$) and evaporated under reduced pressure to give the product as a white solid. Recrystallization from hexane/ethyl acetate gave the title compound as a white solid (1.15 g). Mp 140°–142° C.; TLC (dichloromethane/methanol 30:0.4): Rf=0.60. $^1$H NMR (CDCl$_3$) δ7.45 (s, 2H), 4.65 (br s, 2H), 4.05 (s, 2H), 4.00 (s, 1H), 1.40 (s, 9H). Anal. calcd. for C$_{11}$H$_{16}$N$_2$O$_2$SBr$_2$: C, 33.02; H, 4.03; N, 7.00. Found: C, 33.52; H, 4.04; N, 6.92.

EXAMPLE 40

4-t-Butylaminosulphonylmethyl-2,6-dibromo-N-trifluoro-acetylaniline

To a stirred solution of the product of Example 39 (1.01 g, 2.52 mmol) and pyridine (0.26 mL, 3.28 mmol, 1.30 eq) in anhydrous methylene chloride (15 mL) at 0° C. under a nitrogen atmosphere was added dropwise trifluoroacetic anhydride (0.38 ml, 2.68 mmol, 1.1 eq). The resultant reaction mixture was stirred at 0° C., under a nitrogen atmosphere, for 1 hour. The reaction mixture was then diluted with dichloromethane (150 mL), washed with water (2×50 mL) and dried (MgSO$_4$). Evaporation under reduced pressure gave a white solid which was recrystallized from hexane/diethyl ether to give the title compound as a white solid (1.10 g). mp 166°–167° C.; TLC (dichloromethane/methanol 30:0.4): Rf=0.21. $^1$H NMR (CDCl$_3$) δ7.75 (br s, 1H), 7.70 (s, 2H), 4.20 (s, 2H), 4.10 (s, 1H), 1.45 (S, 9H). Anal calcd. for C$_{13}$H$_{15}$N$_2$O$_3$SBr$_2$F$_3$: C, 31.48; H, 3.05; N, 5.65. Found: C, 31.41; H, 3.11, N, 5.55.

EXAMPLE 41

(R)-1-(N-Benzyloxycarbonylpyrrolidin-2-yl)-3-[N-(4-t-butylaminosulphonylmethyl-2,6-dibromophenyl)-N-trifluoro-acetylamino]propene To a stirred solution of the product of Example 40 (28.0 g, 56.0 mmol) and triphenylphosphine (15.0 g, 86.0 mmol, 1.53 eq) in anhydrous tetrahydrofuran (70 mL), under a nitrogen atmosphere, at 10° C. was added dropwise a solution of diethylazodicarboxylate (8.9 mL, 56 mmol) in anhydrous tetrahydrofuran (15 mL). The reaction solution was then warmed to 25° C. and stirred for a further 25 minutes whereupon a solution of the product of Example 12A (14.79 g, 57.0 mmol) in anhydrous tetrahydrofuran (45 mL) was added dropwise, over 10 minutes. The reaction solution was then stirred at 25° C., under a nitrogen atmosphere for 18 hours. The resulting reaction solution was evaporated under reduced pressure, triturated with diethyl ether, filtered and the filtrate evaporated under reduced pressure and the residue was column chromatographed using silica gel (approximately 850 g), eluting with an ethyl acetate gradient in hexanes to afford the title compound as a white foam. TLC (hexane/ethyl acetate 1:1): Rf=0.65. $^1$H NMR (CDCl$_3$) [Note: due to slow nitrogen inversion two conformers of the products are seen by NMR spectroscopy] δ7.50–7.80 (m, 2H), 7.25–7.42 (m, 5H), 5.42–5.65 (m, 2H), 5.30 (s, 0.14H), 5.00–5.20 (m, 2H), 4.02–4.55 (m, 6H), 3.28–3.45 (m, 2H), 1.25–1.90 (m, 13H). Anal calcd for C$_{28}$H$_{32}$N$_3$O$_5$SBr$_2$F$_3$. 7/100 CH$_2$Cl$_2$: C, 45.23; H, 4.34; N, 5.64. Found: C, 45.06; H, 4.44; N, 5.87.

EXAMPLE 42

(R)-3-(N-Benzyloxycarbonylpyrrolidin-2-ylmethyl)-7-bromo-5-(t-butylaminosulphonylmethyl)-1H-indole To a stirred solution of the product of Example 41 (29.90 g, 40.44 mmol) in 1,2-dimethoxyethane (160 mL) under a nitrogen atmosphere, at 20° C. was added palladium (II) acetate (0.97 g, 4.32 mmol) followed by tetrabutylammonium chloride hydrate (11.25 g, 40.48mmol) and triethylamine (22.3 mL, 160 mmol). The reaction solution was stirred for a further hour at 20° C. and then heated at reflux for 18 hours. The reaction solution was then allowed to cool to 20° C., evaporated under reduced pressure, taken up in ethyl acetate (800 mL) and washed with water. The organic layer was separated, dried (MgSO$_4$) and evaporated under reduced pressure to give a dark brown foam. Column chromatography using elution with 10% acetone in dichloromethane failed to provide a more pure title compound. The resulting crude product (21.3 g of an off-white foam) was used as such in the preparation of Example 43.

EXAMPLE 43

(R)-7-Bromo-5-(t-butylaminosulphonylmethyl)-3-(N-methylpyrrolidin-2-methyl)-1H-indole To a stirred suspension of lithium aluminium hydride (7.07 g, 186 mmol) in anhydrous tetrahydrofuran (100 mL), at 0° C., under a nitrogen atmosphere, was added dropwise, over 30 minutes, a solution of the resulting product of Example 42 (21.3 g) in anhydrous tetrahydrofuran (100 mL). The resulting mixture was allowed to warm to room temperature and then stirred for a further 56 hours. The reaction was then cooled to 0° C. and cautiously treated with water (7.0 mL), followed by 15% aqueous sodium hydroxide solution (7.0 mL), and then with more water (21.0 mL). The resulting black precipitate was removed by filtration, washing with ethyl acetate. The filtrate was then washed with water, dried (MgSO$_4$) and evaporated under reduced pressure to give the crude products as a gum. This was column chromatographed using silica gel (50 g) and elution with dichloromethane/methanol (100:5) followed by dichloromethane/methanol/ammonium hydroxide (90:10:1) to afford the title compound (9.9g) as a white foam. TLC (dichloromethane/methanol/ammonium hydroxide 90:10): Rf=0.33. $^1$H NMR (CDCl$_3$) δ8.35 (br s, 1H), 7.52 (s, 1H), 7.40 (s, 1H), 7.12 (s, 1H), 4.30 (s, 2H), 4.00 (s, 1H), 3.12–3.25 (m, 2H), 2.60–2.72 (m, 1H), 2.50–2.10 (m, 1H), 2.49 (s, 3H), 2.22–2.38 (m, 1H), 1.55–1.78 (m, 4H), 1.39 (s, 9H) $[α]^{25}_D$=+47° (CH$_3$OH, c=0.1) Anal. calcd. for C$_{19}$H$_{28}$N$_3$O$_2$SBr: C, 51.59; H, 6.38; N, 9.50. Found: C, 51.84; H, 6.52; N, 9.52.

EXAMPLE 44

(R)-5-(t-Butylaminosulphonylmethyl)-3-(N-methylpyrrolidin-2-ylmethyl)-1H-indole A solution of the product of Example 43 (5.79 g, 13.1 mmol) and 20% palladium hydroxide/carbon (5.7 g) was stirred under a hydrogen atmosphere (60 psi) for 24 hours. The resultant reaction mixture was filtered through a pad of CELITE, washing with absolute ethanol. The combined filtrates were evaporated under reduced pressure. The residue was taken up in a mixture of 2N sodium bicarbonate and dichloromethane. The organic layer was separated, dried (MgSO$_4$) and evaporated under reduced pressure. This was column chromatographed using silica gel (90 g) and elution with dichloromethane/methanol/ammonium hydroxide (90:10:1) to afford the title compound as a white solid (3.0 g). mp 73°–75° C. TLC (dichloromethane/methanol/ammonium hydroxide 90:10:1): Rf=0.36. $^1$H NMR (CDCl$_3$) δ8.25 (br s, 1H), 7.60 (s, 1H). 7.35 (d, 1H), 7.22 (d, 1H), 7.05 (s, 1H), 5.25 (s, 1/5H), 4.35 (s, 2H), 3.90 (s, 1H), 3.10–3.22 (m, 2H), 2.55–2.70 (m, 1H), 2.42–2.55 (m, 1H), 2.45 (s, 3H), 2.18–2.30 (m, 1H), 1.50–1.90 (m, 4H), 1.40 (s, 9H). $[\alpha]^{25}_D=$ 58° (CH$_3$OH, c=0.1). Anal. calcd. for C$_{19}$H$_{29}$N$_3$O$_2$S.$\frac{1}{10}$ CH$_2$Cl$_2$: C, 61.68; H, 7.91; N, 11.29. Found : C, 61.67; H, 8.14; N, 11.30.

EXAMPLE 45

(R)-5-(Aminosulphonylmethyl)-3-(N-methylpyrrolidin-2-ylmethyl)-1H-indole

A solution of the product of Example 44 (5.92 g, 16.3 mmol) and p-toluenesulphonic acid (470 mg, 2.5 mmol) in acetic anhydride (90 mL) was refluxed, under a nitrogen atmosphere, for 6 hours. The reaction mixture was then cooled to 25° C. and evaporated under reduced pressure, azeotroping with toluene and dichloromethane. The resultant dark brown foam was dissolved in trifluoroacetic acid (50.0 mL) and stirred under a nitrogen atmosphere at 25° C. for 18 hours. The reaction mixture was then evaporated under reduced pressure, azeotroping with dichloromethane. A slurry of potassium carbonate (1.86 g) in methanol (85 mL) was added to the resultant gum and the reaction mixture heated to reflux for 30 minutes. The resultant reaction mixture was then cooled to 25° C. and evaporated under reduced pressure to give a black oil. Purification by column chromatography using silica gel and elution with methylene chloride/methanol/ammonium hydroxide (90:10:1) afford the title compound as a white foam (2.6 g). TLC (dichloromethane/methanol/ammonium hydroxide 80:20:1): Rf =0.43. $^1$H NMR (CD$_3$OD) $\delta$7.62 (s, 1H), 7.35 (d, 1H), 7.18 (d, 1H), 7.10 (s, 1H), 5.48 (s, 9/10 H), 4.40 (s, 2H) 3.08–3.30 (m, 2H), 2.55–2.70 (m, 2H), 2.50 (s, 3H), 2.20–2.42 (m 1H) 1.52–1.90 (m,4H). $[\alpha]^{25}_D=65°$ (CH$_3$OH, c=0.1). Anal. calcd. for C$_{15}$H$_{21}$N$_3$SO$_2$ . $\frac{9}{20}$ CH$_2$Cl$_2$: C, 53.69; H, 6.39; N, 12.16. Found: C, 53.58; H, 6.45; N, 11.76.

EXAMPLE 46

4-Methylaminosulfonylmethyl-N-trifluoroacetylaniline

To a chilled solution of pyridine (4 mL) in methylene chloride (100 mL) was added trifluoroacetic anhydride (7.0 mL) followed by 4methylaminosulfonylmethylaniline (9.55 g). After 30 minutes at 0° C., the reaction mixture was filtered to give the title compound (11.6 g) as a light yellow powder. TLC (EtOAc/hexane 2:1) Rf=0.36.

EXAMPLE 47

2-Bromo-4-methylaminosulfonylmethyl-N-trifluoroacetylaniline

To a chilled suspension of 4-methylaminosulfonylmethyl-N-trifluoroacetylaniline(10.9 g) in methanol (100 mL) was added sodium bicarbonate (28 g), followed by bromine (18.3 g) in methylene chloride (30 mL). The reaction mixture was then diluted with methylene chloride (70 mL) and quenched by the addition of sodium sulfite (20 g), filtered through CELITE and concentrated in vacuo to a yellow residual solid. This solid was twice reslurried in methylene chloride (300 mL) then refiltered and the filtrates evaporated in vacuo. The residual materials were combined in 10% acetone/methylene chloride solution and concentrated then purified by column chromatography (eluting with 4% acetone in methylene chloride) to give the title compound (4.10g) mp 170° C.; TLC (methylene chloride/acetone 15:1) Rf=0.36, and the corresponding dibromide (5.56 g) TLC (methylene chloride/acetone 15:1) Rf=0.31.

EXAMPLE 48

2,6-Dibromo-4-methylaminosulfonylmethylaniline

To a stirred solution of 4-methylaminosulfonylmethylaniline (10 g) in a mixture of methylene chloride (100 mL) and methanol (200 mL) was added sodium bicarbonate (12.6 g) followed by bromine (16 g) in methylene chloride (80 mL). Then the reaction mixture was evaporated in vacuo and the residue partitioned between ethyl acetate (200 mL) and water (100 mL). The ethyl acetate phase was washed with water and brine then dried and evaporated to give the title compound as a brown solid (17.1 g). mp 155–157° C. $^1$H NMR (CDCL$_3$) $\delta$7.4 (s, 2H), 4.6 (bs, 2H), 4.1 (m, 3H), 2.75 (d, 3H).

EXAMPLE 49

2,6-Dibromo-4-methylaminosulfonylmethyl-N-trifluoroacetylaniline 2,6-Dibromo-4-methylaminosulfonylmethylaniline(410 g) was stirred in methylene chloride (8 L) containing pyridine (118 g) and treated with trifluoroacetic anhydride (307.5 g) in methylene chloride (300 mL). Upon complete consumption of the aniline the reaction mixture was diluted with methylene chloride (2 L) and with water (5 L) resulting in precipitation of the title compound (281.9 g) which was removed by filtration. mp 179°–180° C. TLC (EtOAc/hexane 1:1): Rf=0.3. Anal calcd. for C$_{10}$H$_9$Br$_2$F$_3$N$_2$O$_3$S: C 26.45; H, 2.00; N, 6.17. Found C 26.46; H, 1.79; N, 6.12.

Further title compound (165 g) was recovered by crystallization from the (water-washed) combined filtrate and washes upon concentration.

EXAMPLE 50

(R)-1-(N-Benzyloxycarbonylpyrrolidin-2-yl)-3-hydroxypropene

To a stirred solution of (R)-ethyl 3-(N-benzyloxycarbonylpyrrolidin-2-yl)-2-propenoate (574 g) in tetrahydrofuran (5.7 L) at about −78° C. was added boron trifluoride etherate (295.4 g) and then diisobutylaluminum hydride (1.5M in toluene, 3.91 L, 3.1 eq) added (over two hours) maintaining the temperature below −62° C. The resulting solution was stirred (between −78° and −62° C.) for three hours and then quenched into aqueous citric acid solution (2 kg citric acid in 5 L water plus 4 L ice) over about 40 minutes. The phases were separated and the aqueous phase extracted with ethyl acetate (2×2.1 L). The combined organic solution was dried (over magnesium sulphate) and evaporated, then the residual oil purified by chromatography through silica gel, eluting with mixed ethyl acetate/hexane (9:1 to 4:1) to give the title compound as an oil (260 g), as produced in Example 12A (as an alternative, the residual oil can be purified by chromatography through silica gel eluting with ethyl acetate:hexane (1:1)).

EXAMPLE 51

(R)-1-(N-Benzyloxycarbonylpyrrolidin-2-yl)-3-[N-(4-methylaminosulfonylmethyl-2,6-dibromophenyl)-N-trifluoroacetylamino]propene Triphenylphosphine (5.71 g) was dissolved in anhydrous tetrahydrofuran (30 mL) and, in an ice bath, diethylazodicarboxylate (3.71 g in 20 mL anhydrous THF) was added dropwise. Having removed the ice-bath, the reaction mixture was diluted with a further 20 mL anhydrous THF, followed by 2,6-dibromo-4-methylaminosulfonylmethyl-trifluoroacetylaniline (6.45 g in 50 mL anhydrous THF), and (R)-1-

(N-Benzyloxycarbonylpyrrolidin-2-yl)-3-hydroxypropene (5.51 g in 30 mL anhydrous THF) added dropwise. When conversion was judged complete the reaction mixture was evaporated in vacuo (onto silica gel—20 g) and purified by column chromatography (SiO2—1.6 kg) eluted with 5% acetone in methylene chloride to give the title compound as a colorless foam (9.13 g). TLC (methylene chloride/acetone 9:1) Rf=0.60; Anal Calcd. for $C_{25}H_{26}Br_2F_3N_3O_5S$ C 43.1; H, 3.7; N, 6.0. Found C, 43.93; H, 3.99; N, 6.00.

Similarly, the reaction may be conducted in 1,2-dimethoxyethane solvent and processed without purification to directly yield the compound of Example 52 under standard Heck coupling conditions (in mixed 1,2-dimethoxyethane with N,N-dimethylformamide).

EXAMPLE 52

(R)-3-(N-Benzyloxycarbonylpyrrolidin-2-ylmethyl)-7-bromo-5-(methylaminosulfonylmethyl)-1H-indole (R)-1-(N-Benzyloxycarbonylpyrrolidin-2-yl)-3-[N-(4-methylaminosulfonylmethyl-2,6-dibromophenyl)-N-trifluoroacetylamino]propene (9.00 g) in triethylamine (70 mL) containing N,N-dimethylformamide (20 mL), tetra-n-butylammonium chloride (3.61 g) and palladium acetate (1.01 g) was heated at 80° C. until conversion was complete. The cooled reaction mixture was filtered through CELITE and washed with methylene chloride. The combined filtrate and washings were then evaporated in vacuo onto silica gel (15 g) then purified by column chromatography (SiO2—1.6 kg) eluted with 4% acetone in chloroform. The product-rich fractions were combined and evaporated then re-purified by crystallization from a mixture of diethyl ether (50 mL) and methylene chloride (10 mL). The title compound was recovered by filtration (washing with hexanes) as a colorless solid (2.40 g). TLC (methylene chloride/acetone 10:1) Rf=0.35; Anal calcd. for $C_{23}H_{26}BrN_3O_4S$: C, 53.1; H, 5.0; N, 8.1. Found C, 53.13; H, 5.0; N, 7.8.

Further title compound (2.03 g) was recovered from the crystallization liquor upon evaporation and purification by silica chromatography (300 g SiO2 eluted with diethyl ether).

EXAMPLE 53

(R)-7-Bromo-5-(methylaminosulfonylmethyl)-3-(N-methylpyrrolidin-2-ylmethyl)-1H-indole To a chilled suspension of lithium aluminium hydride (47.89 g) in tetrahydrofuran (938 mL), (R)-3-(N-benzyloxycarbonylpyrrolidin-2-ylmethyl)-7-bromo-5-(methylaminosulfonylmethyl)-1H-indole (262.7 g) in tetrahydrofuran (1250 mL total) was added slowly dropwise. The reaction mixture was stirred at ambient temperature and then warmed to 40° C. until conversion was complete. Then, the mixture was cooled and quenched by slow addition of industrial methylated spirit (160 mL), followed by 4M aqueous sodium hydroxide solution (45 mL), then water (142 mL). The mixture was then filtered (through Arbacel). The filtered solids were reslurried in hot industrial methylated spirit (1600 mL) then refiltered. The filtered solids were then washed with a further portion of industrial methylated spirit (200 mL) and then again reslurried from hot industrial methylated spirit (1600 mL). The resultant slurry was again refiltered. The combined filtrates and washings were evaporated in vacuo to give a crude oil which was stirred in mixed water (1000 mL) / ethyl acetate (1000 mL). The aqueous phase was separated and washed with ethyl acetate (500 mL)(then the aqueous discarded) and then the ethyl acetate extracts combined and diluted with water (1000 mL) and the whole acidified (by addition of concentrated hydrochloric acid). The aqueous phase was separated and the organic phase washed with water (500 mL). These two aqueous phases were combined and made basic (by addition of 40% aqueous sodium hydroxide solution) and the product re-extracted with ethyl acetate (2×1000 mL), then again at $pH_9$ with further ethyl acetate (500 mL). The combined ethyl acetate extracts were evaporated to an oil then re-evaporated from acetone (250 mL) to give the title compound (200.7 g) as a semi-solid mass. TLC (diethyl ether/ethyl acetate/ methanol/diethyl amine 50:50:5:5): Rf =0.26. $^1$H NMR ($d_6$ DMSO) δ11.05 (s, 1H), 7.5 (s, 1H), 7.3 (s, 1H), 7.2 (s, 1H), 6.85 (q, 1H), 4.35 (s, 2H), 2.95 (m, 2H), 2.55 (d, 3H), 2.5 (m, 1H), 2.35–2.3 (m, 1H and s, 3H), 2.1 (m, 1H), 1.75–1.4 (m, 4H).

EXAMPLE 54

(R)-5-(Methylaminosulfonylmethyl)-3, (N-methylpyrrolidin-2-ylmethyl)-1H-indole

A solution of (R)-7-bromo-5-(methylaminosulfonyl-methyl)-3-(N-methylpyrrolidin-2-ylmethyl)-1H-indole(193 g) in industrial methylated spirit (950 mL) containing Pearlman's catalyst (47.6 g total) was exposed to hydrogen gas (50 psi). The catalyst was then filtered through an Arbacel pad, washing with hot industrial methylated spirit (2×100 mL) and the combined filtrate and washings evaporated in vacuo to an organic residue. The filtered solids (catalyst +filter aid) were then reslurried in 2N hydrochloric acid (500 mL) then re-filtered (through Arbacel)and the filtrand washed with 2N hydrochloric acid (4×250 mL) and water (2×100 mL). The aqueous filtrate and washes were combined with the organic residue and then once washed with ethyl acetate (1000 mL). The aqueous solution was chilled then made basic by addition of 40% aqueous sodium hydroxide solution precipitating the title compound as a pale-yellow solid. This solid was filtered, washed with water (2×100 mL) and dried in vacuo to give the title compound (89.9 g). TLC (methyl iso-butyl ketone/acetic acid/water 2:1:1 Top phase): Rf=0.23. $^1$H NMR ($d_6$ DMSO) δ10.85 (s, 1H), 7.5 (s, 1H), 7.3 (d, 1H), 7.15 (s, 1H), 7.05 (d, 1H), 6.8 (q, 1H), 4.35 (s, 2H), 3.0 (m, 2H), 2.55–2.4 (d, 3H and m, 2H), 2.35 (s, 3H), 2.1 (m, 1H), 1.7–1.4 (m, 4H).

Further title compound (32.4 g) could be recovered from the catalyst solids by repeating the extractions into 2N hydrochloric acid and water and again precipitating solid product by the addition of aqueous sodium hydroxide solution.

EXAMPLE 55

(R)-5-(Methylaminosulfonylmethyl)-3-(N-methylpyrrolidin-2-ylmethyl)-1H-indole (R)-3-(N-Benzyloxycarbonylpyrrolidin-2-ylmethyl)-7-bromo-5-(methylaminosulfonylmethyl)-1H-indole (3.0 g) in ethanol (45 ml) was exposed to hydrogen (15 psi) over Pearlman's catalyst (1.5 g) until complete consumption of the substrate was evident (if necessary a second charge of catalyst can be made after filtration of the original catalyst through Arbacel and washing the filtered solids with ethanol—50 ml). Then the reaction was filtered through Arbacel (washing with ethanol—150 ml) and the combined filtrate and washings evaporated (and re-evaporated from methylene chloride) to an off-white solid (the hydrobromide salt of (R)-5-(methylaminosulfonylmethyl) -3-(pyrrolidin-2-ylmethyl)-1H-indole) which was dissolved in water (100 ml). From this aqueous solution (R)-5-(methylaminosulfonylmethyl)-3-(pyrrolidin-2-ylmethyl)-1H-indole (1.4 g) was extracted into ethyl acetate (ca. 850 ml) after addition of 15% aqueous sodium hydroxide solution to pH 8.

(R)-5-(Methylaminosulfonylmethyl)-3-(pyrrolidin-2-ylmethyl)-1H-indole (1.3 g) in tetrahydrofuran (12 mL) was treated with an aqueous solution (12 mL) of the monosodium salt of phosphorous acid (made from 169 mg sodium hydroxide and 346 mg phosphorous acid). To this mixture was added 37% aqueous formaldehyde (343 mg) and then the reaction mixture was heated to 60° C. until conversion was complete. The organic solvent was removed by atmospheric distillation then made basic by addition of aqueous sodium hydroxide solution (to pH 10). This causes precipitation of the title compound (0.945 g).

Similarly, the hydrobromide salt of (R)-5-(methylaminosulfonylmethyl)-3-(pyrrolidin-2-ylmethyl)-1H-indole may be used directly in the reductive amination process (above) simply by incorporation of an extra molar equivalent of sodium hydroxide in the aqueous solution.

EXAMPLE 56

(R)-3-(N-Benzyloxycarbonylpyrrolidin-2-ylcarbonyl)-5-bromo-1H-indole

Two solutions containing the reactants were prepared separately as follows:

To a stirred solution of N-benzyloxycarbonyl-D-proline (291.93 g) in dichloromethane (291.9 mL) and toluene (370.8 mL) containing N,N-dimethylformamide (1.46 mL) was added oxalyl chloride (102.2 mL) in toluene (291.9 mL) and the resulting solution was stirred at ambient temperature overnight. The solution was then purged by passing a stream of dry nitrogen gas for five hours. This solution of N-benzyloxycarbonyl-D-proline acid chloride was ready for use.

In parallel, a solution of ethyl magnesium bromide (800 mL of a 3M solution in ether) was added dropwise over one hour to a stirred solution of 5-bromoindole (459.15 g) in dichloromethane (4391.4 mL). The mixture was stirred and heated at reflux for 30 minutes then cooled to −20° C. The above solution of N-benzyloxycarbonyl-D-proline acid chloride was added dropwise with stirring (over one hour) and stirring was continued for a further 30 minutes. Then a solution of ammonium chloride (1122.3 g) in water (5855.3 mL) was added at this temperature and the mixture allowed to warm to room temperature. Further ammonium chloride (1452.3 g) in water (2000 mL) was added to allow separation of the phases. The phases were separated and the aqueous phase extracted with dichloromethane (1.95 L) then discarded. The combined organic phases were washed with aqueous sodium bicarbonate solution (2.7 L), then with brine (1 L) before concentration to low volume (about 1 L). This concentrate was diluted with ethyl acetate (1250 mL) and then further diluted with hexane (1250 mL). The resulting slurry was stirred at ambient temperature before collection of the title compound (361.4 g) by filtration (washing with 1:1 ethyl acetate:hexane-2×300 ml) and drying in vacuo. This material is as described in Example 26.

EXAMPLE 57

(R)-1-Acetyl-5-(2-phenylsulfonylethenyl)-3-(N-methylpyrrolidin-2-ylmethyl)-1H-indole A solution of (R)-5-bromo-3-(N-methylpyrrolidin-2-ylmethyl)-1H-indole (50 g) in dimethylformamide (40 mL) containing triethylamine (18.98 g) was treated with acetic anhydride (19.15 g) over ten minutes, then the mixture was heated to 90°–100° C. for two hours then allowed to cool. This solution was added (over ten minutes, washing in with 20 mL of DMF) to a solution of palladium acetate (1.91 g), tri-o-tolylphosphine (5.20 g), phenyl vinyl sulphone (35.86 g) and triethylamine (36.24 g) in dimethylformamide (90 mL) and the mixture was heated to reflux for three hours. The mixture was then cooled and filtered through Arbacel (washing with dimethylformamide—2×50 mL-then with water—2×50 mL). This solution (in two portions) was quenched into dilute aqueous hydrochloric acid (3016 mL total) then the pH of the aqueous solutions adjusted to about 8 (by addition of aqueous sodium hydroxide). The precipitated materials were filtered, washed with water (each twice with 50 mL) then dried in vacuo (to 78.65 g). This material (74.57 g) was reslurried in methanol (500 mL) containing water (250 mL) then refiltered, washing with 2:1 methanol:water mixture (2×50 mL) then dried in vacuo to give the title compound as a beige solid (57.55 g): mp, 86°–90° C.; IR (KBr) 1700, 1605, 1460, 1450, 1385, 1150, 1085, cm$^{-1}$; LRMS (TSP), m/z 423, 381, 165, 135, 133.

EXAMPLE 58

(R)-5-(2-Phenylsulfonylethenyl)-3-(N-methylpyrrolidin-2-ylmethyl)-1H-indole

A suspension of (R)-1-acetyl-5-(benzenesulfonylethenyl)-3-(N-methyl-pyrrolidin-2-ylmethyl)-1H-indole (220.8 g) in methanol (2.21 L) was treated with potassium carbonate (72.23 g) and stirred at ambient temperature. After about one hour active carbon (22.1 g) was added to the solution then water (660 mL) added slowly. The mixture was filtered and the filtrate heated to reflux and water (660 mL) added dropwise. The mixture was allowed to cool and crystallize, then further water was added slowly (3.31 l). The resulting solid was filtered, washed with 1:2 methanol:water mixture (2×200 mL) then dried in vacuo to give the title compound (149 g): mp, 84°–87° C. IR (KBr) 1600, 1450, 1290, 1145, 1085 cm$^{-1}$; $^1$H NMR (CDCl$_3$) 8.4 (b, 1H), 8.0 (d, 2H), 7.8 (d, 1H), 7.7 (s, 1H), 7.6–7.5 (m, 3H), 7.3 (s, 2H), 7.05 (b, 1H), 6.75 (d, 1H), 3.15 (m, 2H), 2.6 (m, 1H), 2.45 (s, 3H), 2.4 (s, 1H), 2.2 (m, 1H), 2.0–0.5 (m, 4H); LRMS (TSP), m/z 381, 165, 133, 119.

EXAMPLE 59

(R)-5-(2-Phenylsulfonylethyl)-3-(N-methylpyrrolidin-2-ylmethyl)-1H-indole

A stirred solution of (R)-5-(2benzenesulfonylethenyl)-3-(N-methylpyrrolidin-2-ylmethyl)-1H-indole (34.0 g) in acetone (200 mL) was treated with methanesulfonic acid (8.5871 g) then 5% palladium on carbon (50% wet) (34.0 g) added and the mixture exposed to hydrogen (50 psi) at ambient temperature. When conversion was judged to be complete the mixture was filtered (washing with acetone—85 mL and mixed acetone/water—81 mL/4 mL). The combined filtrate and washings were diluted with water (800 mL) and the pH adjusted (with stirring) to about 11 by addition of 40% aqueous sodium hydroxide. After granulation of the precipitate the solids were collected by filtration to give the title compound (25.08 g) as that produced in Example 32).

We claim:
1. A compound of the formula

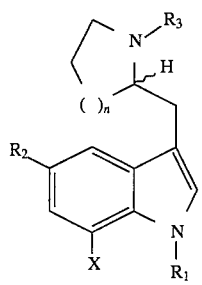

wherein n is 0, 1, or 2; X is hydrogen, chlorine, bromine, or iodine; $R_1$ is hydrogen; $R_2$ is —$(CH_2)_m$—$SO_2NR_5R_6$ $R_3$ is $C_1$ to $C_6$ linear or branched alkyl; $R_5$ is selected from hydrogen, $C_1$ to $C_6$ alkyl, aryl, and $C_1$ to $C_3$ alkyl-aryl, $R_6$ is selected from $C_1$ to $C_6$ alkyl, aryl, and $C_1$ to $C_3$ alkyl-aryl, or $R_5$ and $R_6$ taken together to form a 4, 5, or 6 membered ring; y is 0, 1, or 2; x is 1 or 2; m is 0, 1, 2, or 3; and the above aryl groups and the aryl moieties of the above alkylaryl groups are independently selected from phenyl and substituted phenyl, wherein said substituted phenyl may be substituted with one to three groups selected from $C_1$ to $C_4$ alkyl, halogen, hydroxy, cyano, carboxamido, nitro, and $C_1$ to $C_4$ alkoxy, and the pharmaceutically acceptable salts thereof.

2. The R enantiomer of a compound according to claim 1.
3. A compound according to claim 1 wherein $R_1$ is hydrogen; $R_2$ is —$(CH_2)_m$—$SO_2NHR_5$, $R_3$ is methyl; and m and $R_5$ are as defined in claim 1.
4. A compound according to claim 1, said compound being selected from:
   (R)-5-(2-methylaminosulfonylethyl)-3-(N-methylpyrrolidin-2-ylmethyl)-1H-indole;
   (R)-5-(methylaminosulfonylmethyl)-3-(N-methylpyrrolidin-2-ylmethyl)-1H-indole;
   (R)-5-(2-aminosulphonylethyl)-3-(N-methylpyrrolidin-2-ylmethyl)-1H-indole;
   (R-5-(2-N,N-dimethylaminosulphonylethyl)-3-(N-methylpyrrolidin-2-ylmethyl)-1H-indole;
   (R)-7-Bromo-5-(methylaminosulfonylmethyl)-3-(N-methylpyrrolidin-2-ylmethyl)-1H-indole.

5. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

6. A pharmaceutical composition for treating disorders arising from deficient serotonergic neurotransmission comprising an amount of a compound according to claim 1 effective in treating such a disorder and a pharmaceutically acceptable carrier.

7. A method for treating a condition selected from hypertension, depression, anxiety, eating disorders, obesity, drug abuse, cluster headache, migraine, pain and chronic paroxysmal hemicrania and headache associated with vascular disorders comprising administering to a mammal requiring such treatment an amount of a compound according to claim 1 effective in treating such condition.

8. A method for treating disorders arising from deficient serotonergic neurotransmission comprising administering to a mammal requiring such treatment an amount of a compound according to claim 1 effective in treating such a disorder.

9. The compound 5-(methylaminosulfonylmethyl)-3-(N-methylpyrrolidin-2-ylmethyl)-1H-indole or a pharmaceutically acceptable salt thereof.

10. A compound according to claim 9, wherein the compound is (R)-5-(methylaminosulfonylmethyl)-3-(N-methylpyrrolidin-2-ylmethyl)-1H-indole.

11. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 10 ranging from 0.1 μg to 200 mg effective in treating such condition and a pharmaceutically acceptable carrier.

12. A pharmaceutical composition for treating disorders arising from deficient serotonergic neurotransmission comprising an amount of a compound according to claim 10 ranging from 0.1 μg to 200 mg effective in treating such a disorder and a pharmaceutically acceptable carrier.

13. A method for treating a condition selected from hypertension, depression, anxiety, eating disorders, obesity, drug abuse, cluster headache, migraine, pain and chronic paroxysmal hemicrania and headache associated with vascular disorders comprising administering to a mammal requiring such treatment an amount of a compound according to claim 10 ranging from 0.1 μg to 200 mg effective in treating such condition.

14. A method for treating disorders arising from deficient serotonergic neurotransmission comprising administering to a mammal requiring such treatment an amount of a compound according to claim 10 ranging from 0.1 μg to 200 mg effective in treating such a disorder.

15. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 9 ranging from 0.1 μg to 200 mg effective in treating such condition and a pharmaceutically acceptable carrier.

16. A pharmaceutical composition for treating disorders arising from deficient serotonergic neurotransmission comprising an amount of a compound according to claim 9 ranging from 0.1 μg to 200 mg effective in treating such a disorder and a pharmaceutically acceptable carrier.

17. A method for treating a condition selected from hypertension, depression, anxiety, eating disorders, obesity, drug abuse, cluster headache, migraine, pain and chronic paroxysmal hemicrania and headache associated with vascular disorders comprising administering to a mammal requiring such treatment an amount of a compound according to claim 9 ranging from 0.1 μg to 200 mg effective in treating such condition.

18. A method for treating disorders arising from deficient serotonergic neurotransmission comprising administering to a mammal requiring such treatment an amount of a compound according to claim 9 ranging from 0.1 μg to 200 mg effective in treating such a disorder.

* * * * *

UNITED STATES PATENT AND TRADEMARK OFFICE
CERTIFICATE OF CORRECTION

PATENT NO : 5,607,951
DATED : Mar. 4, 1997
INVENTOR(S) : John E. Macor; Martin J. Wythes It is certified that error appears in the above-identified patent and that said Letters Patent are hereby corrected as shown below:

Column 59, line 20, cancel "y is 0, 1, or 2; x is 1 or 2;".

Signed and Sealed this

Tenth Day of April, 2001

Attest:

NICHOLAS P. GODICI

Attesting Officer     Acting Director of the United States Patent and Trademark Office